(12) United States Patent
Coon et al.

(10) Patent No.: US 10,852,306 B2
(45) Date of Patent: Dec. 1, 2020

(54) GAS-PHASE PURIFICATION FOR ACCURATE ISOBARIC TAG-BASED QUANTIFICATION

(71) Applicant: Wisconsin Alumni Research Foundation, Madison, WI (US)

(72) Inventors: Joshua J. Coon, Middleton, WI (US); Michael S. Westphall, Fitchburg, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 30 days.

(21) Appl. No.: 15/611,232

(22) Filed: Jun. 1, 2017

(65) Prior Publication Data
US 2017/0285042 A1    Oct. 5, 2017

Related U.S. Application Data

(62) Division of application No. 13/438,209, filed on Apr. 3, 2012, now Pat. No. 9,698,001.
(Continued)

(51) Int. Cl.
| G01N 33/68 | (2006.01) |
| G01N 33/483 | (2006.01) |
| H01J 49/00 | (2006.01) |
| H01J 49/04 | (2006.01) |
| H01J 49/26 | (2006.01) |

(52) U.S. Cl.
CPC ....... *G01N 33/6848* (2013.01); *G01N 33/483* (2013.01); *H01J 49/0072* (2013.01); *H01J 49/04* (2013.01); *H01J 49/26* (2013.01); *G01N 2458/00* (2013.01); *G01N 2560/00* (2013.01); *Y10T 436/24* (2015.01)

(58) Field of Classification Search
None
See application file for complete search history.

(56) References Cited

U.S. PATENT DOCUMENTS

| 7,749,769 B2 | 7/2010 | Hunt et al. |
| 7,982,070 B2 | 7/2011 | Smith et al. |

(Continued)

FOREIGN PATENT DOCUMENTS

| WO | WO 2007/109292 | 9/2007 |
| WO | WO 2007/131191 A2 | 11/2007 |

(Continued)

OTHER PUBLICATIONS

Amunugama et al. (2004) "Whole Protein Dissociation in a Quadrupole Ion Trap: Identification of an a Priori Unknown Modified Protein," Anal. Chem. 76(3):720-727.
(Continued)

*Primary Examiner* — Xiaoyun R Xu
(74) *Attorney, Agent, or Firm* — Leydig, Voit & Mayer, Ltd.

(57) ABSTRACT

Described herein are mass spectrometry systems and methods which improve the accuracy of isobaric tag-based quantification by alleviating the pervasive problem of precursor interference and co-isolation of impurities through gas-phase purification. During the gas-phase purification, the mass-to-charge ratios of precursor ions within at least a selected range are selectively changed allowing ions having similar unmodified mass-to-charge ratios to be separated before further isolation, fragmentation or analysis.

7 Claims, 29 Drawing Sheets

Related U.S. Application Data

(60) Provisional application No. 61/471,461, filed on Apr. 4, 2011.

(56) References Cited

U.S. PATENT DOCUMENTS

| | | |
|---|---|---|
| 8,278,115 B2 | 10/2012 | Coon et al. |
| 2010/0330680 A1 | 12/2010 | Frey et al. |
| 2011/0297823 A1 | 12/2011 | Coon et al. |
| 2012/0022230 A1 | 1/2012 | Smith et al. |
| 2012/0091330 A1 | 4/2012 | Coon et al. |
| 2012/0261568 A1 | 10/2012 | Coon et al. |

FOREIGN PATENT DOCUMENTS

| | | |
|---|---|---|
| WO | WO 2009/073505 | 6/2009 |
| WO | WO 2010/104981 A2 | 9/2010 |

OTHER PUBLICATIONS

Cargile et al. (2001) "Identification of Bacteriophage MS2 Coat Protein from *E. coli* Lysates via Ion Trap Collisional Activation of Intact Protein Ions," Anal. Chem. 73(6):1277-1285.
Choe et al. (2007) "8-plex Quantitation of Changes in Cerebrospinal Fluid Protein Expression in Subjects Undergoing Intravenous Immunoglobulin Treatment for Alzheimer's Disease," Proteomics 7(20):3651-3660.
Chrisman et al. (2006) "Parallel Ion Parking of Protein Mixtures," Anal. Chem. 78(1):310-316.
Coon et al. (2005) Proc. Natl. Acad. Sci. USA. 102(27):9463-9468.
Cox et al. (2008) "MaxQuant Enables High Peptide Identification Rates, Individualized p.p.b.-Range Mass Accuracies and Proteome-Wide Protein Quantification," Nature Biotechnology 26(12):1367-1372.
Dayon et al. (2008) "Relative Quantification of Proteins in Human Cerebrospinal Fluids by MS/MS Using 6-Plex Isobaric Tags," Anal. Chem. 80(8):2921-2931.
De Godoy et al. (2008) "Comprehensive Mass-Spectrometry-Based Proteome Quantification of Haploid Versus Diploid Yeast," Nature 455:1251-1255.
Ebeling et al. (2000)" Corona Discharge in Charge Reduction Electrospray Mass Spectrometry," Anal. Chem. 72(21):5158-5161.
Elias et al. (2007) "Target-Decoy Search Strategy for Increased Confidence in Large-Scale Protein Identifications by Mass Spectrometry," Nat. Methods 4(3):207-214.
Geer et al. (2004) "Open Mass Spectrometry Search Algorithm," J. Proteome Res. 3(5):958-964.
He et al. (2002) "Dissociation of Multiple Protein Ion Charge States Following a Single Gas-Phase Purification and Concentration Procedure," Anal. Chem. 74:4653-4661.
Jiang et al. (2002) "Quantitative Analysis of the Yeast Proteome by Incorporation of Isotopically Labeled Leucine," J. Proteome Res. 1:345-350.
Karp et al. (2010) "Addressing Accuracy and Precision Issues in iTRAQ Quantitation," Mol Cell Proteomics 9:1885-1897.
Louris et al. (1990) "Ion Isolation and Sequential Stages of Mass Spectrometry in a Quadrupole Ion Trap Mas Spectrometer," Internatl J of Mass Spectrometry and Ion Processes 96:117-137.
Lu et al. (2009) "Systems-Level Dynamic Analyses of Fate Change in Murine Embryonic Stem Cells," Nature 462(7271): 358-364.
Ludwig et al. (2006) "Feeder-Independent Culture of Human Embryonic Stem Cells," Nat. Materials, 3(8):637-646. Correction: Oct. 2006, 3(10):1.
Martin et al. (2000) "Subfemtomole MS and MS/MS Peptide Sequence Analysis Using Nano-HPLC Micro-ESI Fourier Transform Ion Cyclotron Resonance Mass Spectrometry," Anal. Chem. 72(18):4266-4274.
Mcluckey et al. (1998) "Ion/Ion Chemistry of High-Mass Multiply Charged Ions," Mass Spectrom. Rev. 17:369-407.
Mcluckey et al. (1998) "Ion/Ion Proton-Transfer Kinetics: Implications for Analysis of Ions Derived from Electrospray of Protein Mixtures," Anal. Chem. 70(6):1198-1202.
Mcluckey et al. (2000) "Ion Trap Collisional Activation of Protonated Poly(Propylene Imine) Dendrimers: Generations 1-5," Internatl J of Mass Spectrometry 195/196:419-437.
Mcluckey et al. (2002) "Ion Parking during Ion/Ion Reactions in Electrodynamic Ion Traps," Anal. Chem. 74(2):336-346.
Mcluckey et al. (2011) "Ion/neutral, ion/electron, ion/photon, and ion/ion interactions in tandem mass spectrometry: do we need them all? Are they enough?" J. Am. Soc. Mass Spectrom. 22(1):3-12.
Ogorzalek Loo et al. (1992) "A New Approach for the Study of Gas-Phase Ion-Ion Reactions Using Electrospray Ionization," J Am Soc Mass Spectrom 3:695-705.
Ogorzalek Loo et al. (1994) "Proton Transfer Reaction Studies of Multiply Charged Protein in a High Mass-To-Charge Ratio Quadrupole Mass Spectrometer," J Am Soc Mass Spectrometer, 5:1064-1071.
Ogorzalek Loo et al. (1995) "Proton Transfer Reactions of Multiply Charged Peptide and Protein Cations and Anions," J Am Soc Mass Spectrometer, 30:339-347.
Olsen et al. (2010) "Quantitative Phosphoproteomics Reveals Widespread Full Phosphorylation Site Occupancy During Mitosis," Science Signaling 3(104):1-15.
Ong et al. (2002) "Stable Isotope Labeling by Amino Acids in Cell Culture, SILAC, as a Simple and Accurate Approach to Expression Proteomics," Molecular & Cellular Proteomics 1(5):376-386.
Ong et al. (2005) "Mass Spectrometry-Based Proteomics Turns Quantitative,"Nat. Chem. Biol. 1(5):252-262.
Ow et al. (2009) "iTRAQ Underestimation in Simple and Complex Mixtures: 'The Good, the Bad and the Ugly'," Journal of Proteome Research, 8(11):5347-5355.
Phanstiel et al. (2008) "Gas-Phase Concentration, Purification, and Identification of Whole Proteins from Complex Mixtures," J. Am. Soc. Mass Spectrom. 19:1255-1262.
Phanstiel et al. (2009) "Peptide Quantification Using 8-Plex Isobaric Tags and Electron Transfer Dissociation Tandem Mass Spectrometry," Anal Chem 81(4):1693-1698.
Prazeller et al. (2003) "Proton transfer reaction ion trap mass spectrometer," 17:1593-1599.
Reid et al. (2002) "Gas-Phase Concentration, Purification, and Identification of Whole Proteins from Complex Mixtures," J. Am. Chem. Soc. 124:7353-7362.
Reid et al. (2002) "Tandem Mass Spectrometry of Ribonuclease A and B: N-Linked Glycosylation Site Analysis of Whole Protein Ions," Anal. Chem. 74:577-583.
Ross et al. (2004) "Multiplexed Protein Quantitation in *Saccharomyces cerevisiae* Using Amine-Reactive Isobaric Tagging Reagents," Molecular & Cellular Proteomics 3(12):1154-1169.
Scalf et al. (1999) "Controlling Charge States of Large Ions," Science 283:194-197.
Scalf et al. (2000) "Charge Reduction Electrospray Mass Spectrometry," Anal. Chem. 72:52-60.
Smith et al. (2001) "Charge Reduction Electrospray Mass Spectrometry: Controlling Charge States of Large Ions," FASEB Journal, 904.3, 1 page.
Stephenson et al. (1996) "Ion/Ion Proton Transfer Reactions for Protein Mixture Analysis," Anal. Chem. 68:4026-4032.
Stephenson et al. (1996) "Ion/Ion Reactions in the Gas Phase: Proton Transfer Reactions Involving Multiply-Charged Proteins," J. Am. Chem. Soc. 118(31):7390-7397.
Stephenson et al. (1997) "Gaseous Protein Cations Are Amphoteric," J. Am. Chem. Soc. 119(7):1688-1696.
Swaney et al. (2010) "Value of Using Multiple Proteases for Large-Scale Mass Spectrometry-Based Proteomics," Journal of Proteome Research, 9(3):1323-1329.
Thompson et al. (2003) "Tandem Mass Tags: A Novel Quantification Strategy for Comparative Analysis of Complex Protein Mixtures by MS/MS," Anal. Chem. 75(8):1895-1904.
Wenger et al. (2011) "COMPASS: A Suite of Pre- and Post-Search Proteomics Software Tools for OMSSA," Proteomics 11:1064-1074.

(56) References Cited

OTHER PUBLICATIONS

Wenger et al. (2011) "Gas-phase purification enables accurate, multiplexed proteome quantification with isobaric tagging," Nat. Methods. 8(11):933-935.
Zhu et al. (2002) "Amino Acid Residue Specific Stable Isotope Labeling for Quantitative Proteomics," Rapid Communications in Mass Spectrometry 16:2115-2123.
U.S. Appl. No. 11/460,063, 2007/0023621, U.S. Pat. No. 7,408,147.
U.S. Appl. No. 12/130,103, 2009/0321633, U.S. Pat. No. 7,884,324.
U.S. Appl. No. 11/726,307, 2008-0050833, U.S. Pat. No. 7,982,070.
U.S. Appl. No. 12/489,037, 2010/0320372, U.S. Pat. No. 8,274,059.
U.S. Appl. No. 12/323,766, 2009-0173878, U.S. Pat. No. 8,278,115.
U.S. Appl. No. 12/759,950, 2010-0330680.
U.S. Appl. No. 13/086,638, 2011-0297823.
U.S. Appl. No. 13/155,682, 2012-0022230.
U.S. Appl. No. 13/438,301, 2012-0261568.
U.S. Appl. No. 13/484,560, 2012-0305760.
U.S. Appl. No. 13/234,398, 2012-0091330.
U.S. Appl. No. 13/619,164, 2013-0078728.
U.S. Appl. No. 13/625,731.
U.S. Appl. No. 13/660,677.
U.S. Appl. No. 13/418,972.
Deutsches Patent—und Markenamt, Office Action, dated Sep. 29, 2020, corresponding to German Patent Application No. 10 2012 102 874.5, 8 pages.

Ion-Ion Reactions

+ + − → Charged Products → MS analysis reaction types:

Electron Transfer

Proton Transfer

Anion Attachment

A.

B.

A.

B.

*These figures show charge-state distribution for the TMT-labeled mixed organism sample used in the study*

GAS-PHASE PURIFICATION FOR ACCURATE ISOBARIC TAG-BASED QUANTIFICATION

CROSS REFERENCE TO RELATED APPLICATIONS

This application is a divisional of U.S. application Ser. No. 13/438,209, filed Apr. 3, 2012, which claims the benefit of and priority under 35 U.S.C. 119(e) to U.S. Provisional Application 61/471,461 filed on Apr. 4, 2011 entitled "Gas-Phase Purification For Accurate Isobaric Tag-Based Quantification", which is hereby incorporated by reference in its entirety.

STATEMENT REGARDING FEDERALLY SPONSORED RESEARCH OR DEVELOPMENT

This invention was made with government support under GM080148 and GM081629 awarded by the National Institutes of Health. The government has certain rights in the invention.

BACKGROUND

The ability to identify proteins and determine their chemical structures has become central to the life sciences. The amino acid sequence of proteins provides a link between proteins and their coding genes via the genetic code, and, in principle, a link between cell physiology and genetics. The identification of proteins provides a window into complex cellular regulatory networks.

Mass spectrometry (MS), including but not limited to triple quadropole and ion trap mass spectrometers, is among the most widely used platforms for molecular analysis and identification—spanning natural products, pharmaceuticals and biologics. Most mass spectrometer-based experiments begin with the isolation of a group of compounds from a set of samples through some sort of extraction technique, such as extraction of proteins from tissues, cell lysates or fluids followed by proteolytic digestion of those proteins into peptides (i.e., bottom-up proteomics). Frequently, but not necessarily, mass spectrometers are coupled with some form of separation, such as electrophoretic or chromatographic separation systems. Over the course of just a few hours, mass spectral instruments can autonomously interrogate tens of thousands of molecular species via tandem mass spectrometry (MS/MS).

Quantitative analysis in chemistry is the determination of the absolute or relative abundance of one, several, or all particular substance(s) present in a sample. For biological samples, quantitative analysis performed via mass spectrometry can determine the relative abundance of peptides and proteins. The accepted methodology for performing mass spectrometric quantitation is accomplished using a mass spectrometer capable of MS/MS fragmentation (i.e., triple quadropole or ion trap spectrometers). The quantitation process can involve isobaric tagging of peptide precursors, which when combined with post-acquisition software, provides the relative abundance of peptides. However, when a peptide precursor is selected for tandem mass spectrometry, there are often interfering species with similar mass-to-charge ratios that are co-isolated and subjected to activation. These species are often other isobarically tagged peptides with different relative quantitation, which therefore disturb the quantitative measurement of the peptide of interest.

As a result, protein identification technologies have rapidly matured such that constructing catalogs of the thousands of proteins comprised by a cell using mass spectrometry is now relatively straightforward [de Godoy, L. M. F. et al. *Nature* 455, 1251-1255 (2008); Swaney, D. L., Wenger, C. D. & Coon, J. J. *J. Proteome Res.* 9, 1323-1329 (2010)]; however, knowing how the abundance of these molecules change under various circumstances is not [Ong, S. E. & Mann, M. *Nat. Chem. Biol.* 1, 252-262 (2005)]. Stable isotope labeling by amino acids in cell culture (SILAC) provides a means to make binary or ternary comparisons [Jiang, H. & English, A. M. *J. Proteome Res.* 1, 345-350 (2002); Ong, S. E. et al. *Mol. Cell. Proteomics* 1, 376-386 (2002)]. By interlacing these two- or three-way experiments, higher-order comparisons can be obtained [Olsen, J. V. et al. *Sci. Signal.* 3, ra3 (2010)]. Such large-scale multiplexed experiments are invaluable, as they (1) allow measurement of time-course experiments, (2) permit collection of biological replicates, and (3) enable direct comparison of transcriptomic and proteomic data.

Constructing this type of multi-faceted proteomics study, however, is an arduous undertaking and has only been accomplished in a handful of experiments by an even smaller group of researchers. The first impediment is the requirement to grow multiple groups of cells with various labels. This step is actually less limiting than the second major obstacle: each binary or ternary set must be analyzed separately. When combined with the need for extensive pre-MS fractionation and technical replicates, a large-scale experiment via SILAC demands three to six months of constant instrument usage.

Isobaric tagging [Thompson, A. et al. *Anal. Chem.* 75, 1895-1904 (2003); Ross, P. L. et al. *Mol. Cell. Proteomics* 3, 1154-1169 (2004)], is an elegant solution to this problem, allowing relative quantification of up to eight proteomes simultaneously [Choe, L. et al. *Proteomics* 7, 3651-3660 (2007); Dayon, L. et al. *Anal. Chem.* 80, 2921-2931 (2008)]. Further, it is compatible with mammalian tissues and biofluids, unlike metabolic approaches. Despite its potential to enable fast, multiplexed quantitative proteomics, isobaric tagging has not been widely embraced for large-scale studies [Lu, R. et al. *Nature* 462, 358-U126 (2009)]—chiefly because of precursor interference. This problem does not exist for SILAC because abundance measurements are performed with high-resolution MS' analysis in tandem mass spectrometry. Even for very complex samples having tens or hundreds of co-eluting peptides, high-resolving power mass analyzers can easily distinguish the target from neighboring peaks less than 0.01 Th away.

In the isobaric approach, however, the target peptide is isolated at much lower resolution, typically 1-3 Th, and dissociated to produce reporter tags. Therefore, the quantitative signal in the reporter region is compiled from every species in the isolation window [Ow, S. Y. et al. *J. Proteome Res.* 8, 5347-5355 (2009)]. For highly complex mixtures, like those analyzed in large-scale experiments, co-isolation of multiple species is the rule, not the exception (vide infra). This problem erodes quantitative accuracy, as measured ratios tend to be compressed toward the median ratio of 1:1, and thus has restricted isobaric tagging to applications with lower sample complexity.

Isobaric labeling, such as iTRAQ and other types if isobaric tagging reagents, is an important quantitative method as it allows for multiplexing and is directly applicable to clinical samples. A significant source of error, however, occurs when another eluting peptide ion has a m/z value that is very near that of the selected precursor (~50%, in many experiments). The result is the isolation of both species, which are consequently co-dissociated, to produce a composite MS/MS spectrum. The resulting reporter ion ratios do not accurately reflect the relative abundances of either peptide; limiting both the precision and dynamic range of quantitation, as the median peptide ratio is close to 1:1.

The increasing popularity of iTRAQ for quantitative proteomics applications has spurred increased efforts to evaluate its relevance, accuracy, and precision for biological interpretation. Recently, some researchers have begun to assess the accuracy and precision of iTRAQ quantification as well as drawbacks which hinder the applicability and attainable dynamic range of iTRAQ. Some results suggest that crosstalk between interfering factors can result in underestimations. [Ow et al., "iTRAQ Underestimation in Simple and Complex Mixtures: 'The Good, the Bad and the Ugly'", *Journal of Proteome Research*, web publication Sep. 16, 2009]. It is clear that there is tantalizing potential for iTRAQ and other protein labeling methods to provide accurate quantification spanning several orders of magnitude. This potential can be limited, however, by several factors. First, for example, the existence of isotopic impurities often requires correction of mass spectral data to provide accurate quantitation which currently requires the availability of accurate isotopic factors. Second, the interference of mixed MS/MS contribution occurring during precursor selection is a problem that is currently very difficult to minimize.

What is needed is a method of improving the accuracy of mass spectrometry analysis and quantification of samples, particularly samples labeled with isobaric tags.

SUMMARY OF THE INVENTION

The present invention provides systems and methods which utilize gas-phase purification to improve mass spectrometry analysis and quantification. During gas-phase purification, precursor ions are generated from an analyte during a first ionization step, such as the $MS^1$ stage in tandem mass spectrometry. The mass-to-charge ratios of at least a selected range of these precursor ions are manipulated or modified allowing ions having similar unmodified mass-to-charge ratios to be separated before further isolation, fragmentation and/or analysis. Optionally, mass spectrometry data generated from changing the mass-to-charge ratios of the precursor ions is used in conjunction with data generated from analysis of the unmodified precursor ions to provide additional information and identification. In particular, methods and systems described herein improve the accuracy of isobaric tag-based quantification by alleviating the problem of precursor interference and co-isolation of impurities.

In one embodiment, the present invention provides a method of analyzing an analyte using mass spectrometry, where the method comprises:
(a) providing an isobarically labeled analyte;
(b) generating a first distribution of precursor ions from the isobarically labeled analyte;
(c) identifying a range of mass-to-charge ratios of the first distribution of precursor ions;
(d) selectively changing the mass-to-charge ratios of precursor ions in the identified range of mass-to-charge ratios, thereby generating a distribution of mass-to-charge-manipulated precursor ions;
(e) isolating a range of mass-to-charge ratios of the distribution of mass-to-charge-manipulated precursor ions, thereby generating isolated mass-to-charge-manipulated precursor ions;
(f) fragmenting ions corresponding to the isolated mass-to-charge-manipulated precursor ions, thereby generating first product ions; and
(g) measuring the mass-to-charge ratios of the first product ions, thereby generating first product ion mass spectrometry data;

thereby analyzing the analyte using mass spectrometry. In an embodiment, the method further comprises providing an analyte, such as a protein or peptide analyte, and isobarically labeling the analyte so as to generate an isobarically labeled analyte.

In an embodiment, the range of mass-to-charge ratios of the first distribution of precursor ions in step (c) is referred to as the first isolation window and can vary in width. Increased purification will be achieved the narrower this window is around the target mass-to-charge ratio value; however, narrowing the isolation window will also reduce the amount of desired precursor ions that will have their charge or mass manipulated and analyzed leading to less identification. In one embodiment, the identified range of mass-to-charge ratios of the first distribution of precursor ions in step (c) has a width of 3 m/z units or less. In one embodiment, this first isolation window has a width of 0.1 to 10 m/z units, a width of 0.1 to 5 m/z units, a width of 0.5 to 4 m/z units, a width of 1 to 3 m/z units, a width of 1 to 2 m/z units, or a width of 2.5 to 3.5 m/z units centered on the post-manipulation target mass-to-charge ratio value. Wider widths up to about 100 or more mass-to-charge units can be applied. Decreasing the width to a very narrow isolation range (up to about 0.1 mass-to-charge units) provides increased purification In an embodiment, the method further comprises:
(h) generating a second distribution of precursor ions from the isobarically labeled analyte;
(i) identifying a range of mass-to-charge ratios of the second distribution of precursor ions;
(j) fragmenting ions corresponding to the range of mass-to-charge ratios of the second distribution of precursor ions, thereby generating second product ions; and
(k) measuring the mass-to-charge ratios of the second product ions, thereby generating second product ion mass spectrometry data.

In an embodiment, the step of:
(d) selectively changing the mass-to-charge ratios of precursor ions in the identified range of mass-to-charge ratios, thereby generating a distribution of mass-to-charge-manipulated precursor ions; can be performed so that the resulting products have a predictable mass-to-charge ratio change. The mass-to-charge ratio of the precursor ions can be changed by manipulating the mass of the precursor ions within the identified range, or by manipulating the charge of the precursor ions. Charge-transfer reactions, for example, remove charge so that the new mass-to-charge ratio value of the target can be calculated, without need for a separate analysis, so that the step of:
(e) isolating a range of mass-to-charge ratios of the distribution of mass-to-charge-manipulated precursor ions, thereby generating isolated mass-to-charge-manipulated precursor ions;

can be applied immediately following the manipulation step. This second isolation window can vary in width. Increased purification will be achieved the narrower this window is around the post-manipulation target mass-to-charge ratio value; however, narrowing the isolation window will also reduce the amount of desired charge-manipulated precursor ions that will be fragmented and analyzed leading to less identification. In one embodiment, this second isolation window has a width of 0.1 to 10 m/z units, a width of 0.1 to 5 m/z units, a width of 0.5 to 4 m/z units, a width of 1 to 3 m/z units, a width of 1 to 2 m/z units, or a width of 2.5 to 3.5 m/z units centered on the post-manipulation target mass-to-charge ratio value. Wider widths up to about 100 or more mass-to-charge units can be applied. Decreasing the width to a very narrow isolation range (up to about 0.1 mass-to-charge units) provides increased purification.

In an embodiment, the range of mass-to-charge ratios of the second distribution of precursor ions is identified so as not to include mass-to-charge ratios corresponding to reporter ions of the isobarically labeled analyte. In an embodiment, the identified range of mass-to-charge ratios of the second distribution of precursor ions does not include ions having a mass-to-charge ratio less than 400 m/z units. In an embodiment, the identified range of mass-to-charge ratios of the second distribution of precursor ions does not include ions having a mass-to-charge ratio less than 200 m/z units. In an embodiment, the identified range of mass-to-charge ratios of the second distribution of precursor ions does not include ions having a mass-to-charge ratio less than 175 m/z units. In an embodiment, the identified range of mass-to-charge ratios of the second distribution of precursor ions does not include ions having a mass-to-charge ratio less than 150 m/z units.

In an embodiment, the identified range of mass-to-charge ratios of the first distribution of precursor ions and the identified range of mass-to-charge ratios of the first distribution of precursor ions are not the same. In another embodiment, the identified ranges of mass-to-charge ratios of the first and second distributions of precursor ions are the same. In an embodiment, the identified ranges of mass-to-charge ratios of the first and second distributions, independently from one another, have a width of 100 m/z units or less, 10 m/z units or less, 5 m/z units or less, 3 m/z units or less, 2 m/z units or less, or 1 m/z unit or less. In an embodiment, the identified ranges of mass-to-charge ratios of the first and second distributions, independently from one another, have a width of 0.1 to 10 m/z units, a width of 0.1 to 5 m/z units, a width of 0.5 to 4 m/z units, a width of 1 to 3 m/z units, a width of 1 to 2 m/z units, ora width of 2.5 to 3.5 m/z units centered on the post-manipulation target mass-to-charge ratio value.

In an embodiment, this method further comprises storing the first product ions and the second product ions concurrently in a single ion storage device before measuring the mass-to-charge ratios of the first product ions and the second product ions. In an alternate embodiment, the method further comprises storing the first product ions and the second product ions concurrently in separate ion storage devices before measuring the mass-to-charge ratios of the first product ions and second product ions. In another embodiment, the method further comprises storing the first product ions and the second product ions sequentially in a single ion storage device before measuring the mass-to-charge ratios of the first product ions and second product ions.

In an embodiment, the steps of:
  (g) measuring the mass-to-charge ratios of the first product ions, thereby generating product ion mass spectrometry data; and
  (k) measuring the mass-to-charge ratios of the second product ions, thereby generating product ion mass spectrometry data;
are performed concurrently using a single mass analyzer.

Alternatively, the steps of:
  (g) measuring the mass-to-charge ratios of the first product ions, thereby generating product ion mass spectrometry data; and
  (k) measuring the mass-to-charge ratios of the second product ions, thereby generating product ion mass spectrometry data;
are performed sequentially using a single mass analyzer.

In an embodiment, the steps of:
  (g) measuring the mass-to-charge ratios of the first product ions, thereby generating product ion mass spectrometry data; and
  (k) measuring the mass-to-charge ratios of the second product ions, thereby generating product ion mass spectrometry data;
are performed concurrently or non-concurrently using separate mass analyzers.

In an embodiment, the first distribution of precursor ions is subject to collisional dissociation to selectively change the mass-to-charge ratios of precursor ions in the identified range of mass-to-charge ratios, thereby generating a distribution of mass-to-charge-manipulated precursor ions. In an embodiment, for example, the method of the invention further comprises the step of collisionally dissociating precursor ions in the identified range of mass-to-charge ratios, thereby generating the distribution of mass-to-charge-manipulated precursor ions. In an embodiment, the first distribution of precursor ions is subject to photodissociation to selectively change the mass-to-charge ratios of precursor ions in the identified range of mass-to-charge ratios, thereby generating a distribution of mass-to-charge-manipulated precursor ions. In an embodiment, for example, the method of the invention further comprises the step of photodissociating precursor ions in the identified range of mass-to-charge ratios, thereby generating the distribution of mass-to-charge-manipulated precursor ions. Alternatively, in an embodiment, the first distribution of precursor ions is not subject to collisional dissociation to selectively change the mass-to-charge ratios of precursor ions in the identified range of mass-to-charge ratios and/or the first distribution of precursor ions is not subject to photodissociation to selectively change the mass-to-charge ratios of precursor ions in the identified range of mass-to-charge ratios, thereby generating a distribution of mass-to-charge-manipulated precursor ions.

In an embodiment, the first distribution of precursor ions is subject to a reaction with a species to selectively change the mass-to-charge ratios of precursor ions in the identified range of mass-to-charge ratios, thereby generating a distribution of mass-to-charge-manipulated precursor ions. In an embodiment, for example, the method of the invention further comprises the step of reacting the precursor ions in the identified range of mass-to-charge ratios with a species (such as a charge manipulation reactant) so as to generate the distribution of mass-to-charge-manipulated precursor ions. In an embodiment, the reaction with a species to selectively change the mass-to-charge ratios of the range of mass-to-charge ratios comprises an ion-molecule reaction. In an embodiment, the reaction with a species to selectively change the mass-to-charge ratios of the range of mass-to-charge ratios comprises an ion-ion reaction. In an embodiment, the reaction with a species to selectively change the mass-to-charge ratios of the range of mass-to-charge ratios comprises an ion-electron reaction.

Many different species are useful in a reaction with a species to selectively change the mass-to-charge ratios of precursor ions in the identified range of mass-to-charge ratios, thereby generating a distribution of mass-to-chargemanipulated precursor ions. In an embodiment, for example, singly or multiply charged anions of peptides, proteins, oligonucleotides, biological molecules, polymers, or dendrimers are useful in a reaction with a species to selectively change the mass-to-charge ratios of precursor ions in the identified range of mass-to-charge ratios, thereby generating a distribution of mass-to-charge-manipulated precursor ions. In another embodiment any chemical species with a suitable mass (i.e. >20 Da) is useful in a reaction with a species to selectively change the mass-to-charge ratios of precursor ions in the identified range of mass-to-charge ratios, thereby generating a distribution of mass-to-charge-manipulated precursor ions.

In an embodiment, the reaction with a species to selectively change the mass-to-charge ratios of the range of mass-to-charge ratios comprises a proton-transfer reaction. In an embodiment, the proton transfer reaction comprises reaction of the first distribution of precursor ions with fluoranthene, perfluoro-1,3-dimethyl-cyclohexane, 2,6-dichlorophenol, 2,3,4,6-tetrachlorophenol, or 1,4-naphthoquinone.

In an embodiment, the reaction with a species to selectively change the mass-to-charge ratios of the range of mass-to-charge ratios comprises a charge-transfer reaction. In an embodiment, the reaction with a species to selectively change the mass-to-charge ratios of the range of mass-to-charge ratios comprises a electron-transfer reaction.

In an embodiment, the reaction with a species to selectively change the mass-to-charge ratios of the range of mass-to-charge ratios is a reaction that changes the mass of the precursor ions by a known amount. In one embodiment, the mass of each precursor ion is modified by 200 atomic mass units or less, 100 atomic mass units or less, 75 amu atomic mass units or less, 50 atomic mass units or less, 25 atomic mass units or less, or 10 atomic mass units or less.

In an embodiment, the reaction with a species to selectively change the mass-to-charge ratios of the range of mass-to-charge ratios is a reaction that changes the charge state of the precursor ions. This change in charge state is predictable in that the charge state will be increased or decreased by a known amount. In one embodiment, the precursor ions in the identified range of mass-to-charge ratios have a positive charge state, and selectively changing the mass-to-charge ratios of the precursor ions in the identified range comprises increasing or decreasing the positive charge state of each of the precursor ions. In one embodiment, the positive charge state of the precursor ion is increased by 1, by 2, or by 3. In a further embodiment, the positive charge state of the precursor ion is decreased by 1, by 2, or by 3. In a further embodiment, the positive charge state of the precursor ion is decreased by one.

In an embodiment, the step of:
(e) isolating a range of mass-to-charge ratios of the distribution of mass-to-charge-manipulated precursor ions, thereby generating isolated mass-to-charge-manipulated precursor ions;
comprises isolating a range of mass-to-charge ratios of the distribution of mass-to-charge-manipulated precursor ions corresponding to 100 m/z units or less.

In an embodiment, the step of:
(e) isolating a range of mass-to-charge ratios of the distribution of mass-to-charge-manipulated precursor ions, thereby generating isolated mass-to-charge-manipulated precursor ions;
comprises isolating a range of mass-to-charge ratios of the distribution of mass-to-charge-manipulated precursor ions corresponding to 3 m/z units or less.

In an embodiment, the step of:
(e) isolating a range of mass-to-charge ratios of the distribution of mass-to-charge-manipulated precursor ions, thereby generating isolated mass-to-charge-manipulated precursor ions;
comprises isolating a range of mass-to-charge ratios of the distribution of mass-to-charge-manipulated precursor ions corresponding to 1 m/z units or less.

In an embodiment, the step of:
(e) isolating a range of mass-to-charge ratios of the distribution of mass-to-charge-manipulated precursor ions, thereby generating isolated mass-to-charge-manipulated precursor ions;
comprises isolating a range of mass-to-charge ratios of the distribution of mass-to-charge-manipulated precursor ions corresponding to 0.2 m/z units or less.

In an embodiment, the step of:
(e) isolating a range of mass-to-charge ratios of the distribution of mass-to-charge-manipulated precursor ions, thereby generating isolated mass-to-charge-manipulated precursor ions;
comprises isolating a range of mass-to-charge ratios of the distribution of mass-to-charge-manipulated precursor ions corresponding to 0.1 m/z units or less.

In an embodiment, the method further comprises analyzing the mass-to-charge ratios of at least a portion of the first distribution of precursor ions, thereby generating first precursor ion mass spectrometry data corresponding to the first distribution of precursor ions.

In an embodiment, the method further comprises analyzing the mass-to-charge ratios of at least a portion of the mass-to-charge-manipulated precursor ions, thereby generating mass-to-charge-manipulated precursor ion mass spectrometry data corresponding to the distribution of mass-to-charge-manipulated precursor ions.

In an embodiment, the method further comprises analyzing the mass-to-charge ratios of at least a portion of the second distribution of precursor ions, thereby generating second precursor ion mass spectrometry data corresponding to the second distribution of precursor ions.

In an embodiment, the step of:
(f) fragmenting ions corresponding to the isolated mass-to-charge-manipulated precursor ions, thereby generating first product ions;
comprises fragmenting the isolated mass-to-charge-manipulated precursor ions by beam-type collisionally activated dissociation, ultraviolet photo-dissociation, infrared photodissociation, electron transfer dissociation, electron capture dissociation, surface induced dissociation, or resonant excitation collisionally activated dissociation.

In an embodiment, the step of:
(j) fragmenting ions corresponding to the second distribution of precursor ions, thereby generating second product ions;
comprises fragmenting the ions corresponding to the second distribution of precursor ions by beam-type collisionally activated dissociation, ultraviolet photodissociation, infrared photodissociation, electron transfer dissociation, electron capture dissociation, surface induced dissociation, or resonant excitation collisionally activated dissociation.

In an embodiment, the reaction conditions and ion optics are adjusted to maximize the amount of first product ions generated. In an embodiment, the reaction conditions and ion optics are adjusted to maximize the amount of second product ions generated.

In an embodiment, at least a portion of the first product ion mass spectrometry data corresponds to a reporter tag of the isobarically labeled analyte. In an embodiment, at least a portion of the second product ion mass spectrometry data corresponds to a sequence tag of the isobarically labeled analyte.

In an embodiment, the first distribution of precursor ions is generated by an electrospray ionization source or a MALDI source. In an embodiment, the second distribution of precursor ions is generated by an electrospray ionization source or a MALDI source.

In an embodiment, the isobarically labeled analyte comprises proteins or peptides. In an embodiment, the isobarically labeled analyte comprises phosphorylated proteins or peptides. In an embodiment, the isobarically labeled analyte comprises co-translationally modified proteins or peptides. In an embodiment, the isobarically labeled analyte comprises post-translationally modified proteins or peptides. In an embodiment, the isobarically labeled analyte comprises small molecules, pharmaceutical compounds, oligonucleotides, or sugars. In an embodiment, the isobarically labeled analyte comprises isobarically labeled proteins or peptides. In an embodiment, the isobarically labeled analyte is fractionated prior to generating the first distribution of precursor ions from the analyte. In an embodiment, the isobarically labeled analyte is fractionated prior to generating the second distribution of precursor ions from the analyte.

In an embodiment, the method is implemented in a tandem mass spectrometer instrument, a multistage mass spectrometer instrument, or a hybrid mass spectrometer instrument.

In an embodiment, the isobarically labeled analyte comprises proteins or peptides and the isobarically labeled analyte is analyzed to quantify the amount of proteins or peptides in the analyte. In an embodiment, wherein the isobarically labeled analyte comprises one or more proteins.

In an embodiment the method further comprises digesting the one or more proteins. In an embodiment the method further comprises identifying peptides corresponding to the one or more proteins. In an embodiment the method further comprises determining amounts of the one or more proteins. In an embodiment the method further comprises determining a composition of the one or more proteins. In an embodiment the method further comprises determining a post translational modification of the one or more proteins. In an embodiment, the one or more proteins are indicative of a disease state.

Another embodiment provides a method able to be used with stand-alone ion traps (termed "low-resolution Quant-Mode" or "low-res QuantMode") which drastically improves the quantitative accuracy and dynamic range achievable on low-resolution MS instrumentation for isobaric tag-based quantitative analyses of complex samples. The problem of precursor interference is addressed through the use of gas-phase purification and the utilization of carefully designed segmented scan sequences which enables the generation of both optimal reporter ions and optimal sequencing ions for analysis, while minimizing unnecessary drains on the duty cycle of the mass spectrometer.

In one embodiment, the present invention provides a method of analyzing an analyte using mass spectrometry, where the method comprises:
 (a) providing an isobarically labeled analyte;
 (b) generating a first distribution of precursor ions from the isobarically labeled analyte;
 (c) identifying a range of mass-to-charge ratios of the first distribution of precursor ions;
 (d) scanning the precursor ions in the identified range of mass-to-charge ratios to determine the charge state of the identified precursor ions;
 (e) reacting the precursor ions in the identified range of mass-to-charge ratios with a species to selectively change the mass-to-charge ratios of precursor ions in the identified range of mass-to-charge ratios, wherein the reaction with a species to selectively change the mass-to-charge ratios of the range of mass-to-charge ratios comprises a proton-transfer reaction thereby generating a distribution of mass-to-charge-manipulated precursor ions having a decreased positive charge state;
 (f) isolating a range of mass-to-charge ratios of the distribution of mass-to-charge-manipulated precursor ions, thereby generating isolated mass-to-charge-manipulated precursor ions;
 (g) fragmenting ions corresponding to the isolated mass-to-charge-manipulated precursor ions, thereby generating first product ions; and
 (h) measuring the mass-to-charge ratios of the first product ions, thereby generating first product ion mass spectrometry data, thereby analyzing the analyte using mass spectrometry. If the determined charge state of the identified precursor ions is +2 or greater, then isolating the range of mass-to-charge ratios of the distribution of mass-to-charge-manipulated precursor ions is based on the determined charge state of a desired precursor ion.

However, if the determined charge state of the identified precursor ions is unknown or is less than +2, then isolating the range of mass-to-charge ratios of the distribution of mass-to-charge-manipulated precursor ions is based on a desired charge state of +3. Additionally a second quantification scan is performed and the method further comprises the steps of:
 (i) isolating a second range of mass-to-charge ratios of the distribution of mass-to-charge-manipulated precursor ions, thereby generating second isolated mass-to-charge-manipulated precursor ions;
 (j) fragmenting ions corresponding to the second isolated mass-to-charge-manipulated precursor ions, thereby generating second product ions; and
 (k) measuring the mass-to-charge ratios of the second product ions, thereby generating second product ion mass spectrometry data.

The invention also provides systems for performing mass spectrometry. In an embodiment, a mass spectrometer system for analyzing an isobarically labeled analyte is provided, the system comprising:
 an ion source for generating ions from the isobarically labeled analyte;
 first ion separation optics in communication with the ion source for separating ions according to their mass-to-charge ratios;
 ion reaction optics in communication with the first ion separation optics for generating mass-to-charge-manipulated ions;
 ion fragmentation optics in communication with the first ion separation optics for generating product ions;
 second ion separation optics in communication with the ion fragmentation optics for separating ions according to their mass-to-charge ratios;
 a first ion detector in communication with the second ion separation optics for detecting ions separated according to their mass-to-charge ratios;
 a controller operably connected to the first and second ion separation optics, the ion reaction optics, the first ion detector, and the ion fragmentation optics;

wherein the controller controls the ion optics and detector so as to:
- (a) generate a first distribution of precursor ions from the isobarically labeled analyte;
- (b) identify a range of mass-to-charge ratios of the first distribution of precursor ions;
- (c) selectively change the mass-to-charge ratios of precursor ions in the identified range of mass-to-charge ratios, thereby generating a distribution of mass-to-charge-manipulated precursor ions;
- (d) isolate a range of mass-to-charge ratios of the distribution of mass-to-charge-manipulated precursor ions, thereby generating isolated mass-to-charge-manipulated precursor ions;
- (e) fragment ions corresponding to the isolated mass-to-charge-manipulated precursor ions, thereby generating first product ions;
- (f) measure the mass-to-charge ratios of the first product ions, thereby generating first product ion mass spectrometry data; and
- (g) analyze the first product ion mass spectrometry data.

As used throughout the present description, the term "ion optics" is intended to be inclusive of ion optic components of a mass spectrometer system, including, for example, one or more ion separation optics, ion reaction optics, ion fragmentation optics and combinations thereof. As used throughout the present description, the term "detector" is intended to be inclusive of detector components of a mass spectrometer system, including, for example, one or more ion detectors.

In an embodiment, the controller further controls the ion optics and detector so as to:
- (h) generate a second distribution of precursor ions from the isobarically labeled analyte;
- (i) identify a range of mass-to-charge ratios of the second distribution of precursor ions;
- (j) fragment ions corresponding to the range of mass-to-charge ratios of the second distribution of precursor ions, thereby generating second product ions;
- (k) measure the mass-to-charge ratios of the second product ions, thereby generating second product ion mass spectrometry data; and
- (l) analyze the second product ion mass spectrometry data.

In an embodiment, the system further comprises a first ion storage device in communication with the ion fragmentation optics and second ion separation optics and operably connected to the controller.

In an embodiment, the controller further controls the first ion storage device to store the first product ions and the second product ions concurrently in the ion storage device before measuring the mass-to-charge ratios of the first product ions and the second product ions.

In an embodiment, the controller further controls the first ion storage device to store the first product ions and the second product ions sequentially in the ion storage device before measuring the mass-to-charge ratios of the first product ions and the second product ions.

In an embodiment, the system further comprises a second ion storage device in communication with the ion fragmentation optics and second ion separation optics and operably connected to the controller. In an embodiment, the controller further controls the first ion storage device and second ion storage device to store the first product ions in the first ion storage device and the second product ions in the second ion storage device concurrently before measuring the mass-to-charge ratios of the first product ions and the second product ions. However, it should be noted that the controller can also control the first and second storage devices to the store the first and second product ions non-currently.

In an embodiment, the controller controls the ion optics and detector so as to:
- (f) measure the mass-to-charge ratios of the first product ions, thereby generating product ion mass spectrometry data; and
- (k) measure the mass-to-charge ratios of the second product ions, thereby generating product ion mass spectrometry data;

concurrently with the second ion separation optics and first detector.

In an embodiment, the controller controls the ion optics and detector so as to:
- (f) measure the mass-to-charge ratios of the first product ions, thereby generating product ion mass spectrometry data; and
- (k) measure the mass-to-charge ratios of the second product ions, thereby generating product ion mass spectrometry data;

sequentially with the second ion separation optics and first detector.

In an embodiment, the system further comprises:
third ion separation optics in communication with the ion fragmentation optics, for separating ions according to their mass-to-charge ratios;
a third detector in communication with the third ion separation optics, for detecting ions separated according to their mass-to-charge ratios;

wherein the controller controls the ion optics and detectors so as to:
- (f) measure the mass-to-charge ratios of the first product ions, thereby generating product ion mass spectrometry data; and
- (k) measure the mass-to-charge ratios of the second product ions, thereby generating product ion mass spectrometry data;

concurrently with the second ion separation optics and first detector and the third ion separation optics and third detector.

In an embodiment, the controller further controls the ion optics and detectors to: subject the first distribution of precursor ions to collisional dissociation to selectively change the mass-to-charge ratios of precursor ions in the identified range of mass-to-charge ratios, thereby generating a distribution of mass-to-charge-manipulated precursor ions.

In an embodiment, the controller further controls the ion optics and detectors to: subject the first distribution of precursor ions to photodissociation to selectively change the mass-to-charge ratios of precursor ions in the identified range of mass-to-charge ratios, thereby generating a distribution of mass-to-charge-manipulated precursor ions.

In an embodiment, the controller does not further control the ion optics and detectors to: subject the first distribution of precursor ions to collisional dissociation to selectively change the mass-to-charge ratios of precursor ions in the identified range of mass-to-charge ratios, thereby generating a distribution of mass-to-charge-manipulated precursor ions.

In an embodiment, the controller does not further control the ion optics and detectors to: subject the first distribution of precursor ions to photodissociation to selectively change the mass-to-charge ratios of precursor ions in the identified range of mass-to-charge ratios, thereby generating a distribution of mass-to-charge-manipulated precursor ions.

In an embodiment, the controller further controls the ion optics and detectors to: subject the first distribution of precursor ions to reaction with a species to selectively change the mass-to-charge ratios of precursor ions in the identified range of mass-to-charge ratios, thereby generating a distribution of mass-to-charge-manipulated precursor ions. In an embodiment, reaction with a species to selectively change the mass-to-charge ratios of the range of mass-to-charge ratios comprises an ion-molecule reaction. In an embodiment, reaction with a species to selectively change the mass-to-charge ratios of the range of mass-to-charge ratios comprises an ion-ion reaction. In an embodiment, reaction with a species to selectively change the mass-to-charge ratios of the range of mass-to-charge ratios comprises an ion-electron reaction. In an embodiment, reaction with a species to selectively change the mass-to-charge ratios of the range of mass-to-charge ratios comprises a proton-transfer reaction. In an embodiment, the proton transfer reaction comprises reaction of the first distribution of precursor ions with fluoranthene, perfluoro-1,3-dimethyl-cyclohexane, 2,6-dichlorophenol, 2,3,4,6-tetrachlorophenol, or 1,4-naphthoquinone.

In an embodiment, reaction with a species to selectively change the mass-to-charge ratios of the range of mass-to-charge ratios comprises a charge-transfer reaction. In an embodiment, reaction with a species to selectively change the mass-to-charge ratios of the range of mass-to-charge ratios comprises an electron-transfer reaction.

In an embodiment, the controller controls the ion optics and detector so as to:
(d) isolate a range of mass-to-charge ratios of the distribution of mass-to-charge-manipulated precursor ions, thereby generating isolated mass-to-charge-manipulated precursor ions; wherein the range of mass-to-charge ratios of the distribution of mass-to-charge-manipulated precursor ions corresponding to 100 m/z units or less.

In an embodiment, the controller controls the ion optics and detector so as to:
(d) isolate a range of mass-to-charge ratios of the distribution of mass-to-charge-manipulated precursor ions, thereby generating isolated mass-to-charge-manipulated precursor ions; wherein the range of mass-to-charge ratios of the distribution of mass-to-charge-manipulated precursor ions corresponding to 3 m/z units or less.

In an embodiment, the controller controls the ion optics and detector so as to:
(d) isolate a range of mass-to-charge ratios of the distribution of mass-to-charge-manipulated precursor ions, thereby generating isolated mass-to-charge-manipulated precursor ions; wherein the range of mass-to-charge ratios of the distribution of mass-to-charge-manipulated precursor ions corresponding to 1 m/z units or less.

In an embodiment, the controller controls the ion optics and detector so as to:
(d) isolate a range of mass-to-charge ratios of the distribution of mass-to-charge-manipulated precursor ions, thereby generating isolated mass-to-charge-manipulated precursor ions; wherein the range of mass-to-charge ratios of the distribution of mass-to-charge-manipulated precursor ions corresponding to 0.2 m/z units or less.

In an embodiment, the controller controls the ion optics and detector so as to:
(d) isolate a range of mass-to-charge ratios of the distribution of mass-to-charge-manipulated precursor ions, thereby generating isolated mass-to-charge-manipulated precursor ions; wherein the range of mass-to-charge ratios of the distribution of mass-to-charge-manipulated precursor ions corresponding to 0.1 m/z units or less.

In an embodiment, the system further comprises a second ion detector in communication with the first ion separation optics for detecting ions separated according to their mass-to-charge ratios and generating first precursor ion mass spectrometry data corresponding to the first distribution of precursor ions.

In an embodiment, the system further comprises a fourth ion detector in communication with the ion reaction optics for detecting the mass-to-charge ratios of at least a portion of the mass-to-charge-manipulated precursor ions, thereby generating mass-to-charge-manipulated precursor ion mass spectrometry data corresponding to the distribution of mass-to-charge-manipulated precursor ions.

In an embodiment, the system further comprises a fifth ion detector in communication with the second ion separation optics for detecting ions separated according to their mass-to-charge ratios and generating second precursor ion mass spectrometry data corresponding to the second distribution of precursor ions.

In an embodiment, the controller controls the ion optics and detector so as to:
(e) fragment ions corresponding to the isolated mass-to-charge-manipulated precursor ions, thereby generating first product ions; wherein the isolated mass-to-charge-manipulated precursor ions are fragmented by beam-type collisionally activated dissociation, ultraviolet photo-dissociation, infrared photodissociation, electron transfer dissociation, electron capture dissociation, surface induced dissociation, or resonant excitation collisionally activated dissociation.

In an embodiment, the controller controls the ion optics and detector so as to:
(j) fragment ions corresponding to the second distribution of precursor ions, thereby generating second product ions; wherein the isolated mass-to-charge-manipulated precursor ions are fragmented by beam-type collisionally activated dissociation, ultraviolet photo-dissociation, infrared photodissociation, electron transfer dissociation, electron capture dissociation, surface induced dissociation, or resonant excitation collisionally activated dissociation.

In an embodiment, the controller controls the reaction conditions and ion optics to maximize the amount of first product ions generated. In an embodiment, the controller controls the reaction conditions and ion optics to maximize the amount of second product ions generated. In an embodiment, at least a portion of the first product ion mass spectrometry data corresponds to a reporter tag of the isobarically labeled analyte. In an embodiment, at least a portion of the second product ion mass spectrometry data corresponds to a sequence tag of the isobarically labeled analyte.

In an embodiment, the system further comprises an ion storage device in communication with the ion fragmentation optics for storing fragmented ions. In an embodiment, the controller further controls the ion optics and detectors so as to:
(l) store the first product ions and the second product ions in the ion storage device coincidentally before measuring the mass-to-charge ratios of the first product ions and the second product ions.

In an embodiment, at least a portion of the first product ion mass spectrometry data corresponds to an amount of a component of the isobarically labeled analyte. In an embodiment, at least a portion of the second product ion mass spectrometry data corresponds to an amino acid sequence of a component of the isobarically labeled analyte.

In an embodiment, the ion source is an electrospray ionization source or a MALDI source.

In an embodiment, the isobarically labeled analyte comprises proteins or peptides. In an embodiment, the isobarically labeled analyte comprises phosphorylated proteins or peptides. In an embodiment, the isobarically labeled analyte comprises co-translationally modified proteins or peptides. In an embodiment, the isobarically labeled analyte comprises post-translationally modified proteins or peptides. In an embodiment, the isobarically labeled analyte comprises small molecules, pharmaceutical compounds, oligonucleotides, or sugars.

In an embodiment, the system further comprises a fractionation stage operably connected to the ion source for fractionating the isobarically labeled analyte prior to generating the distribution of precursor ions from the isobarically labeled analyte.

In an embodiment, the system comprises a tandem mass spectrometer instrument or a multistage mass spectrometer instrument.

In an embodiment, the isobarically labeled analyte comprises proteins or peptides and the controller controls the ion optics and detectors to analyze the isobarically labeled analyte to quantify the amount of proteins or peptides in the analyte. In an embodiment, the isobarically labeled analyte comprises one or more proteins. In an embodiment, the one or more proteins are digested. In an embodiment, the controller identifies peptides corresponding to the one or more proteins. In an embodiment, the controller determines amounts of the one or more proteins. In an embodiment, the controller determines a composition of the one or more proteins. In an embodiment, the controller determines a post-translational modification of the one or more proteins. In an embodiment, the one or more proteins are indicative of a disease state.

In an embodiment, the controller further controls the ion optics and detector so as to identify the range of mass-to-charge ratios of the second distribution of precursor ions to not include mass-to-charge ratios corresponding to reporter ions of the isobarically labeled analyte. In an embodiment, the identified range of mass-to-charge ratios of the second distribution of precursor ions does not include ions having a mass-to-charge ratio less than 400 m/z units. In an embodiment, the identified range of mass-to-charge ratios of the second distribution of precursor ions does not include ions having a mass-to-charge ratio less than 200 m/z units. In an embodiment, the identified range of mass-to-charge ratios of the second distribution of precursor ions does not include ions having a mass-to-charge ratio less than 175 m/z units. In an embodiment, the identified range of mass-to-charge ratios of the second distribution of precursor ions does not include ions having a mass-to-charge ratio less than 150 m/z units.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

DETAILED DESCRIPTION

Figure 1:
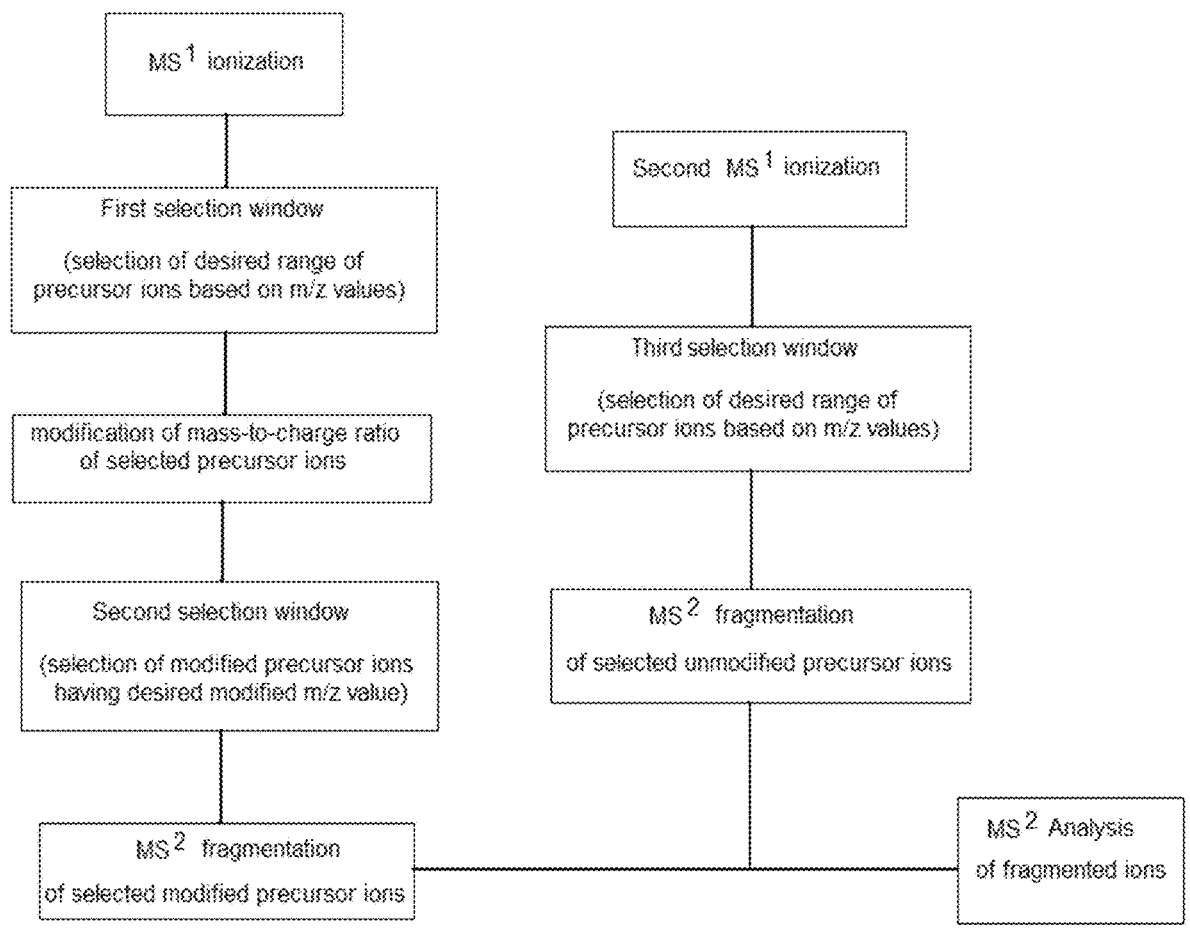
FIG. 1 provides a flowchart illustrating an overview of steps used in an embodiment of the present invention.

Referring to the drawings, like numerals indicate like elements and the same number appearing in more than one drawing refers to the same element. In general the terms and phrases used herein have their art-recognized meaning, which can be found by reference to standard texts, journal references and contexts known to those skilled in the art. The following definitions are provided to clarify their specific use in the context of the invention.

Definitions

As used herein, the term "precursor ion" is used herein to refer to an ion which is produced during ionization stage of mass spectrometry analysis, including the $MS^1$ ionization stage of MS/MS analysis.

As used herein, the terms "product ion" and "secondary ion" are used interchangeably in the present description and refer to an ion which is produced during a fragmentation process of a precursor ion. The term "secondary product ion" as used herein refers to an ion which is the product of successive fragmentations.

As used herein, the term "analyzing" refers to a process for determining a property of an analyte. Analyzing can determine, for example, physical properties of analytes, such as mass or atomic or substituent composition.

As used herein, the term "analyte" refers to a compound, mixture or composition which is the subject of an analysis. Analytes include, but are not limited to, proteins, peptides, small molecules, pharmaceutical compounds, oligonucleotides, sugars and mixtures thereof. An "isobarically labeled analyte" refers to an analyte that has been labeled with one or more isobaric tagging reagents. For example, an "isobarically labeled analyte" can be a mixture containing proteins or peptides labeled with multiple isobaric tagging reagents where the isobaric tagging reagents generate different reporter ions during fragmentation.

As used herein, the term "ion source" refers to a device component which produces ions from a sample. Examples of ion sources include, but are not limited to, electrospray ionization sources and matrix assisted laser desorption/ionization (MALDI) sources.

As used herein, the term "mass spectrometry" (MS) refers to an analytical technique for the determination of the elemental composition of an analyte. Mass spectrometric techniques are useful for elucidating the chemical structures of analytes, such as peptides and other chemical compounds. The mass spectrometry principle consists of ionizing analytes to generate charged species or species fragments and measurement of their mass-to-charge ratios. Conducting a mass spectrometric analysis of an analyte results in the generation of mass spectrometry data relating to the mass-to-charge ratios of the analyte and analyte fragments. Mass spectrometry data corresponding to analyte ion and analyte ion fragments is presented in mass-to-charge (m/z) units representing the mass-to-charge ratios of the analyte ions and/or analyte ion fragments. In tandem mass spectrometry (MS/MS or $MS^2$), multiple rounds of mass spectrometry analysis are performed. For example, samples containing a mixture of proteins and peptides can be ionized and the resulting precursor ions separated according to their mass-to-charge ratio. Selected precursor ions can then be fragmented and further analyzed according to the mass-to-charge ratio of the fragments.

As used herein, the term "interference" refers to a species detected in an analysis which interferes with the detection of a species or analyte of interest. Interference can refer to detection of a protein, or protein fragment, which is not a protein or protein fragment of interest and which interferes with the accurate detection or quantitation of the protein or peptide fragment of interest. Interference can be quantified as an interference ratio, such as a ratio of an amount of interference signal to an amount of analyte signal. In a mass spectral analysis, interference can be manifested as an interference peak which corresponds to detection of a species which is not an analyte of interest.

As described herein, an "isolation window" refers to a range of precursor ions or a range of mass-to-charge-manipulated precursor ions that is selectively separated and fragmented, manipulated or isolated. For example, the range of precursor ions which undergo manipulation of their mass-to-charge ratios can be referred to as a first isolation window; and the range of mass-to-charge-manipulated precursor ions that is isolated prior to fragmentation can be referred to as a second isolation window.

As used herein, the term "species" refers to a particular molecule, compound, ion, anion, atom, electron or proton. For example, as described in certain embodiments herein, precursor ions within a selected mass-to-charge ratio range are reacted with a species to change the mass-to-charge ratio of the precursor ions. This means the selected precursor ions are reacted with a specific molecule, compound, ion, atom, electron or proton to change either the mass of charge of the precursor ions. In one embodiment, if it is desired to alter the mass of the precursor ions, the species can be a molecule or compound which binds to the precursor ions adding to the molecular weight of each precursor ion. In another embodiment, if it is desirable to alter the charge of the precursor ions, the species can be a charge manipulation reactant which adds an electron or proton to a precursor ion thereby changing the charge of the precursor ion.

As used herein, the term "signal-to-noise ratio" refers to a measure which quantifies how much a signal has been corrupted by noise, or unwanted signal. It can also refer to the ratio of signal power to the noise power corrupting the signal. A ratio higher than 1:1 indicates more signal than noise and is desirable for some applications.

As used herein, the term "mass-to-charge ratio" refers to the ratio of the mass of a species to the charge state of a species. The term "m/z unit" refers to a measure of the mass to charge ratio. The Thomson unit (abbreviated as Th) is an example of an m/z unit and is defined as the absolute value of the ratio of the mass of an ion (in Daltons) to the charge of the ion (with respect to the elemental charge).

As used herein, the term "ion optic" refers to a device component which assists in the transport and manipulation of charged particles, for example ions, by the application of electric and/or magnetic fields. The electric or magnetic field can be static, alternating, or can contain both static and alternating components. Ion optical device components include, but are not limited to, ion deflectors which deflect ions, ion lenses which focus ions, and multipoles (such as quadruples) which confine ions to a specific space or trajectory. Ion optics include multipole RF device components which comprise multiple rods having both static and alternating electric and/or magnetic fields.

As used herein, the term "mass spectrometer" refers to a device which creates ions from a sample, separates the ions according to mass, and detects the mass and abundance of the ions. Mass spectrometers include multistage mass spectrometers which fragment the mass-separated ions and separate the product ions by mass one or more times. Multistage mass spectrometers include tandem mass spectrometers which fragment the mass-separated ions and separate the product ions by mass once.

As used herein, the term "disease state" refers to condition that can cause pain, dysfunction, distress, social problems, and/or death to a patient. Methods and systems described herein can be useful for diagnosis of a disease state.

The terms "peptide" and "polypeptide" are used synonymously in the present description, and refer to a class of compounds composed of amino acid residues chemically bonded together by amide bonds (or peptide bonds). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides include, for example, polypeptides comprising 1 to 100 amino acid units, optionally for some embodiments 1 to 50 amino acid units and, optionally for some embodiments 1 to 20 amino acid units.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, iodination or any modification that derivatizes the protein.

As used herein, the term "controller" refers to a device component which can be programmed to control a device or system, as is well known in the art. Controllers can, for example, be programmed to control mass spectrometer systems as described herein. Controllers can be programmed, for example, to carry out ion manipulation and sample analysis methods as described herein on systems and devices as described herein.

As used herein, the term "fractionated" or "fractionate" refers to the physical separation of a sample, as is well known in the art. A sample can be fractionated according to physical properties such as mass, length, or affinity for another compound, among others using chromatographic techniques as are well known in the art. Fractionation can occur in a separation stage which acts to fractionate a sample of interest by one or more physical properties, as are well known in the art. Separation stages can employ, among other techniques, liquid and gas chromatographic techniques. Separation stages include, but are not limited to, liquid chromatography separation systems, gas chromatography separation systems, affinity chromatography separation systems, and capillary electrophoresis separation systems.

Quantitative analysis in chemistry is the determination of the absolute or relative abundance of one, several, or all particular substance(s) present in a sample. For biological samples, quantitative analysis performed via mass spectrometry can determine the relative abundance of peptides and proteins. The accepted methodology for performing mass spec quantitation is accomplished using a mass spectrometer capable of MS/MS fragmentation (i.e. triple quadropole or ion trap). The quantitation process typically involves isobaric tagging of peptide precursors, which when combined with post-acquisition software, provides the relative abundance of peptides.

Gas-phase Purification

Described herein are methods to eliminate interference and to increase purification during mass spectrometry analysis of isobaric tagged analytes. Particularly with lower resolution instruments, interference of ions having similar mass-to-charge ratios erodes dynamic range measurements and decreases accuracy of quantitative analysis, as measured ratios tend to be compressed toward the median (1:1). As described herein, the mass-to-charge ratios of precursor ions within a first isolation window are selectively modified and the modified precursor ions within a second isolation window are then selected for fragmentation and further MS analysis. The use of gas-phase purification can therefore exclude undesired ions from subsequent MS measurements.

One embodiment of the present invention is illustrated in FIG. 1 where ionization during the $MS^1$ stage generates a plurality of precursor ions. In a first selection window, precursor ions having m/z values falling within a desired range are selected and their mass-to-charge ratios subsequently modified to generate modified precursor ions. In a second selection window, modified precursor ions having modified m/z values falling within a second desired range are selected and undergo $MS^2$ fragmentation and analysis. Optionally, a second $MS^1$ ionization step is performed to generate a second set of precursor ions. In a third isolation window, precursor ions having m/z values falling within a third desired range are selected and undergo subsequent $MS^2$ fragmentation and analysis without modification of their mass-to-charge ratios. Optionally, the fragment ions from the modified precursor ions selected from the second isolation window and the fragment ions from the unmodified precursor ions selected from the third isolation window are combined for $MS^2$ analysis.

Figure 11:
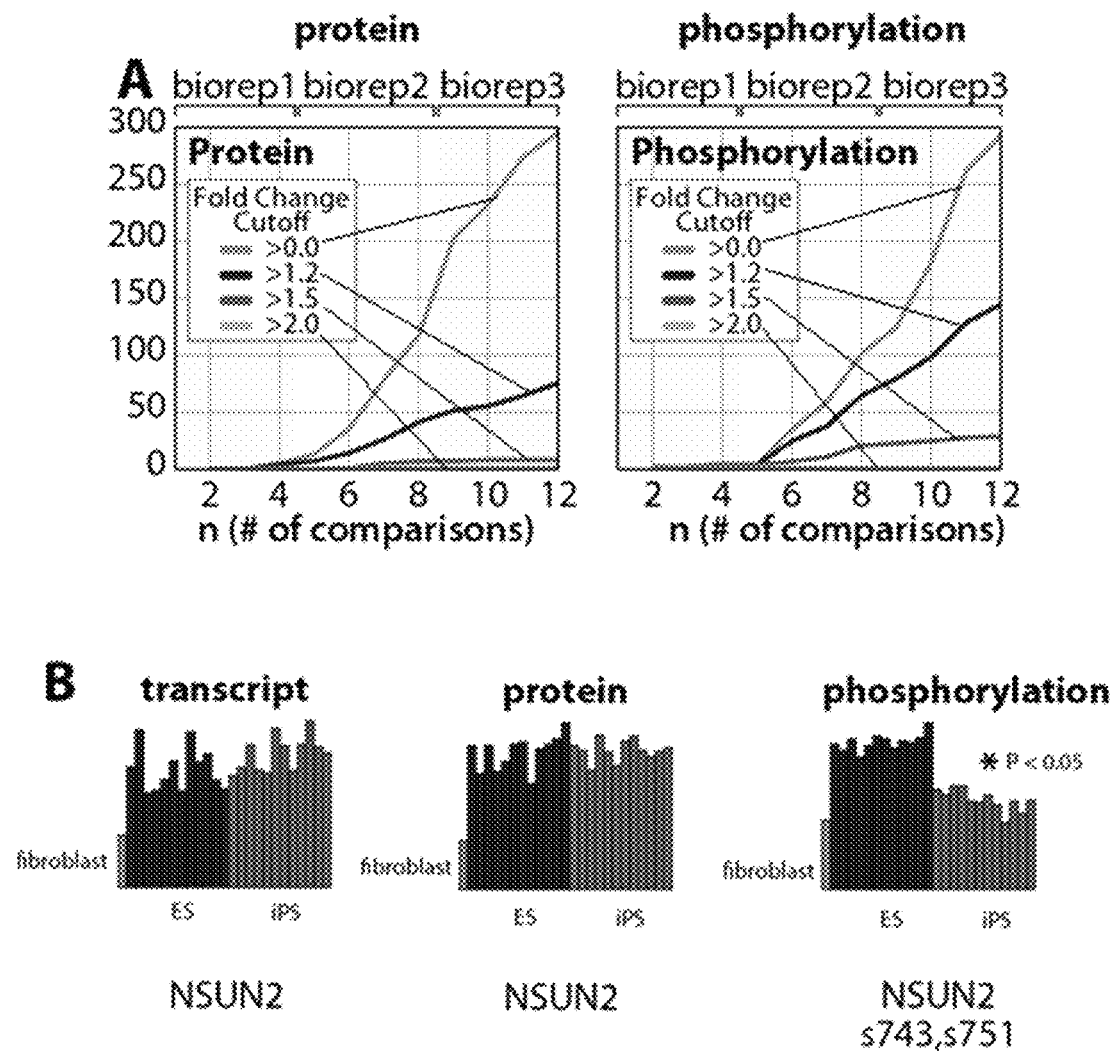
FIG. 11 provides a plot illustrating that a number of replicate analysis are often required to detect statistically significant protein differences (panel A). Panel B shows multiple measurements that reveal subtle but significant ($P<0.05$) differential regulation of two phosphorylation sites on NSUN2 that was only detectable with multiple independent comparisons.

In one embodiment, the present invention allows purification and accurate mass spectrometry analysis of analytes which produce multiple precursor ions in the $MS^1$ stage having similar mass-to-charge ratios. These multiple precursor ions having similar mass-to-charge ratios can be reporter ions from isobarically tagged molecules, such as isobarically tagged peptides. The similarity of the mass-to-charge ratios between multiple precursor ions may also arise because the precursor ions are generated from closely related peptides. For example, proteins and peptides that undergo various degrees of phosphorylation may result in precursor ions having very similar mass-to-charge ratios. FIG. 11 displays data detailing the number of biological replicate analyses required to determine statistically significant differences between human ES and induced pluripotent cell lines (iPS). FIG. 11 shows subtle but significant (P<0.05) differential regulation of a phosphorylation site on NSUN2 that is only detectable with 12 independent comparisons. The number of replicate analysis required to detect statistically significant protein differences is shown in FIG. 11 (panel A). Panel B of FIG. 11 shows multiple measurements that reveal significant (P<0.05) differential regulation of two phosphorylation sites on NSUN2. The present invention increases the accuracy of the mass spectrometry analysis of such proteins and allows for the determination of the amount of such proteins.

Figure 2:
FIG. 2 illustrates different types of ion-ion reactions that can alter the charge of a precursor ion.
Figure 2:
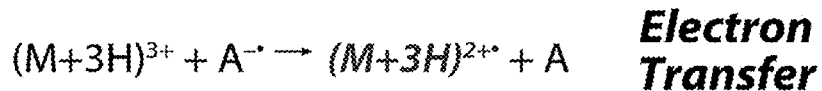
Figure 2:
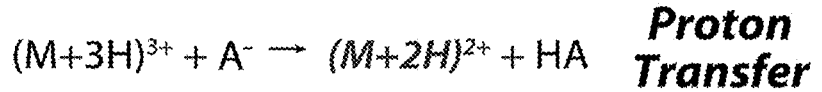

The mass-to-charge ratios of the precursor ions can be selectively changed by reacting the precursor ions, which are typically positively charged, with a species (such as a charge manipulation reactant) so as to change the charge, the mass, or both, of the precursor ion. In one embodiment, the reaction with a species to selectively change the mass-to-charge ratios is an ion-ion reaction that at least changes the charge of the precursor ion. In a further embodiment, the ion-ion reaction is selected from the group consisting of a proton transfer reaction (PTR), an electron transfer reaction, and an anion attachment reaction. For example, these reactions, as illustrated in FIG. 2, react a positively charged ion (cation) with a negatively charged species resulting in a net loss of a charge of the cation. With an electron transfer reaction, the cation gains an electron from the negatively charged species. A proton transfer reaction can be described as the cation losing a proton to the negatively charged species. The resulting mass change in an electron transfer and proton transfer reaction is minimal. With an anion attachment reaction, the negatively charged species binds to the cation which noticeably alters the charge and the mass of the cation.

The mass-to-charge ratio of the precursor ions can be changed by manipulating the mass or charge of the precursor ions. For example, even before electron-transfer dissociation (ETD), proton transfer ion-ion reactions (PTR) were developed to manipulate precursor charge states, purify precursors, and simplify spectra. PTR is typically accomplished by reaction of multiply protonated cations with even-electron anions, resulting in precursor ion de-protonation and charge state reduction. An ETD-enabled orbitrap can permit both ETD and PTR chemistry. Accordingly, one embodiment of the present invention provides a novel approach of using PTR to enable large-scale, multiplexed protein quantification. Stable isotope labeling by amino acids in cell culture (SILAC), the protein quantification gold standard, provides a means to make binary or ternary comparisons [See, e.g., Ong, S. E., B. Blagoev, I. Kratchmarova, D. B. Kristensen, H. Steen, A. Pandey, and M. Mann, *Stable isotope labeling by amino acids in cell culture, silac, as a simple and accurate approach to expression proteomics. Molecular & Cellular Proteomics,* 2002. 1(5): p. 376-386]. SILAC, however, has two major drawbacks: incompatibility with human tissues or biofluids, clearly the major portion of biomedical research, and high labor requirements, which make biological replicate analysis difficult to achieve. The problem is that each binary or ternary set must be analyzed separately. This issue, combined with extensive fractionation, and the need for technical replicates, means that a large-scale experiment via SILAC demands three to five months of constant instrument usage for a single biological replicate. And though this approach can detect extreme differences, it does not afford the statistical power sufficient to reveal subtle or even moderate perturbations and does not offer control or estimation of false positive rates.

Isobaric labeling provides a solution to this problem, allowing relative quantification of up to 8 proteomes simultaneously [See: Thompson, A., J. Schafer, K. Kuhn, S. , J. Schwarz, G. Schmidt, T. Neumann, and C. Hamon, *Tandem mass tags: A novel quantification strategy for comparative* analysis of complex protein mixtures by ms/ms. Analytical Chemistry, 2003. 75(8): p. 1895-1904; Ross, P. L., Y. L. N. Huang, J. N. Marchese, B. Williamson, K. Parker, S. Hattan, N. Khainovski, S. Pillai, S. Dey, S. Daniels, S. Purkayastha, P. Juhasz, S. Martin, M. Bartlet-Jones, F. He, A. Jacobson, and D. J. Pappin, *Multiplexed protein quantitation in saccharomyces cerevisiae using amine-reactive isobaric tagging reagents. Molecular & Cellular Proteomics,* 2004. 3(12): p. 1154-1169; Phanstiel, D., R. Unwin, G. C. McAlister, and J. J. Coon, *Peptide quantification using 8-plex isobaric tags and electron transfer dissociation tandem mass spectrometry. Anal Chem,* 2009. 81(4): p. 1693-8; Choe, L., M. D'Ascenzo, N. R. Relkin, D. Pappin, P. Ross, B. Williamson, S. Guertin, P. Pribil, and K. H. Lee, *8-plex quantitation of changes in cerebrospinal fluid protein expression in subjects undergoing intravenous immunoglobulin treatment for alzheimer's disease. Proteomics,* 2007. 7(20): p. 3651-3660].

Here, differentially isotopically labeled, but isobaric amine-reactive tags are embedded into peptides. Once labeled, the 8 samples are combined and peptides are sequenced individually by MS/MS using CAD. Peptides having the same sequence from each of the 8 samples co-elute and have equivalent m/z values. During MS/MS, however, vibrational excitation induces cleavage of both the peptide backbone and the isobaric tag. Dissociation of the backbone gives rise to fragment ions characteristic of the peptide sequence; dissociation of the tag generates low mass product ions where each label creates a unique m/z reporter peak. Yet despite the potential to enable expedient, multiplexed quantitative proteomics, precursor interference has prevented isobaric labeling from being widely embraced. [See, Lu, R., F. Markowetz, R. D. Unwin, J. T. Leek, E. M. Airoldi, B. D. MacArthur, A. Lachmann, R. Rozov, A. Ma'ayan, L. A. Boyer, O. G. Troyanskaya, A. D. Whetton, and I. R. Lemischka, *Systems-level dynamic analyses of fate change in murine embryonic stem cells. Nature,* 2009. 462(7271): p. 358-U126]. This problem does not exist for SILAC because abundance measurements are performed with high-resolution MS$^1$. Even for very complex samples having tens or hundreds of co-eluting peptides, high-resolving power mass analyzers can easily distinguish the target from neighboring peaks less than 0.01 Th away. In the isobaric approach, however, the target peptide is isolated at much lower resolution, typically 1-3 Th, and dissociated to produce reporter tags. Therefore, the quantitative signal in the reporter region is compiled from every species in the isolation window. [See, Ow, S. Y., M. Salim, J. Noirel, C. Evans, I. Rehman, and P. C. Wright, *Itraq underestimation in simple and complex mixtures: "The good, the bad and the ugly". Journal of Proteome Research,* 2009. 8(11): p. 5347-5355].For highly complex mixtures, like those analyzed in large-scale experiments, co-isolation of multiple species is the rule, not the exception. This problem may erode dynamic range in some situations, as measured ratios tend to be compressed toward the median ratio of 1:1, and thus has restricted the technique to applications with low sample complexity. [See Karp, N. A., W. Huber, P. G. Sadowski, P. D. Charles, S. V. Hester, and K. S. Lilley, *Addressing accuracy and precision issues in itraq quantitation. Mol Cell Proteomics,* 2010]. Described below are methods utilizing gas-phase purification, such as through changing the mass-to-charge ratio via PTR, to systematically eliminate the pervasive interference problem in isobaric tag-based quantification. Allowing large-scale comparison of 8 or more proteomes simultaneously, this straightforward approach has potential to transform the way quantitative proteomics is conducted.

EXAMPLE 1

Gas-Phase Purification Enables Accurate, Large-Scale, Multiplexed Proteomic Quantification Protein identification technologies have rapidly matured such that constructing catalogs of the thousands of proteins comprised by a cell using mass spectrometry (MS) is now relatively straightforward [de Godoy, L. M. F. et al. *Nature* 455, 1251-1255 (2008); Swaney, D. L., Wenger, C. D. & Coon, J. J. *J. Proteome Res.* 9, 1323-1329 (2010)]. Knowing how the abundance of these molecules change under various circumstances is not [Ong, S. E. & Mann, M. *Nat. Chem. Biol.* 1, 252-262 (2005)]. Stable isotope labeling by amino acids in cell culture (SILAC) provides a means to make binary or ternary comparisons [Jiang, H. & English, A. M. *J. Proteome Res.* 1, 345-350 (2002); Ong, S. E. et al. *Mol. Cell. Proteomics* 1, 376-386 (2002)]. By interlacing these two- or three-way experiments, higher-order comparisons can be obtained [Olsen, J. V. et al. *Sci. Signal.* 3, ra3 (2010)]. Such large-scale multiplexed experiments are invaluable, as they (1) allow measurement of time-course experiments, (2) permit collection of biological replicates, and (3) enable direct comparison of transcriptomic and proteomic data.

Constructing this type of multi-faceted proteomics study, however, is an arduous undertaking and has only been accomplished in a handful of experiments by an even smaller group of researchers. The first impediment is the requirement to grow multiple groups of cells with various labels. And this step is actually less limiting than the second major obstacle: each binary or ternary set must be analyzed separately. When combined with the need for extensive pre-MS fractionation and technical replicates, a large-scale experiment via SILAC demands three to six months of constant instrument usage.

Isobaric tagging [Thompson, A. et al. *Anal. Chem.* 75, 1895-1904 (2003); Ross, P. L. et al. *Mol. Cell. Proteomics* 3, 1154-1169 (2004)], allows relative quantification of up to eight proteomes simultaneously [Choe, L. et al. *Proteomics* 7, 3651-3660 (2007); Dayon, L. et al. *Anal. Chem.* 80, 2921-2931 (2008)]. Further, it is compatible with mammalian tissues and biofluids, unlike metabolic approaches. Despite its potential to enable fast, multiplexed quantitative proteomics, isobaric tagging has not been widely embraced for large-scale studies [Lu, R. et al. *Nature* 462, 358-U126 (2009)]—chiefly because of precursor interference. This problem does not exist for SILAC because abundance measurements are performed with high-resolution MS$^1$. Even for very complex samples having tens or hundreds of co-eluting peptides, high-resolving power mass analyzers can easily distinguish the target from neighboring peaks less than 0.01 Th away.

In the isobaric approach, however, the target peptide is isolated at much lower resolution, typically 1-3 Th, and dissociated to produce reporter tags. Therefore, the quantitative signal in the reporter region is compiled from every species in the isolation window [Ow, S. Y. et al. *J. Proteome Res.* 8, 5347-5355 (2009)]. For highly complex mixtures, like those analyzed in large scale experiments, co-isolation of multiple species is the rule, not the exception (vide infra). This problem erodes quantitative accuracy, as measured ratios tend to be compressed toward the median ratio of 1:1, and thus has restricted isobaric tagging to applications with lower sample complexity.

Extent of Interference on Quantitative $MS^2$ Measurements

To document the extent of interference, a precursor purity model was constructed (shown in FIG. 3) by labeling peptides from a whole cell yeast lysate with the tandem mass tag (TMT) 6-plex m/z 126 tag. These peptides were then spiked with peptides from a tryptic digest of human proteins, which had been labeled with the TMT 6-plex m/z 131 tag. By incorporating human peptides as the interference, the precursor contamination typical of a human proteomic analysis can be effectively modeled. Following nHPLC-MS/MS, the reporter m/z regions of MS/MS spectra that were uniquely mapped to yeast were examined. The relative signal abundance of these m/z peaks thus provides a quantitative empirical measurement of interference. On average, only 68% of reporter ion signal originated from the target peptide, as shown in panel A of FIG. 5. Only 3% of MS/MS spectra were of ultrapure (≥99%) precursors.

Figure 4:
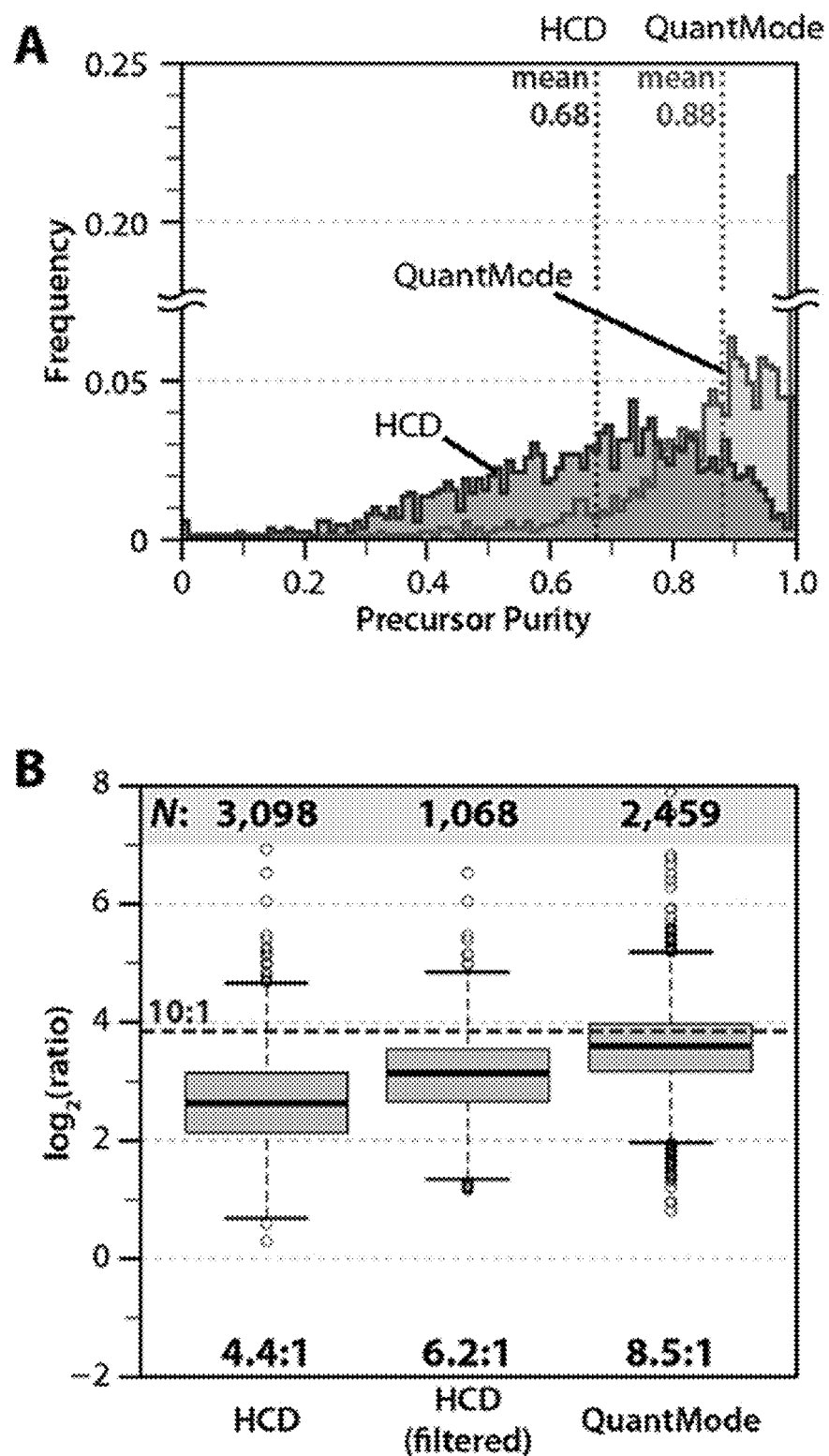
FIG. 4 provides a quantitative accuracy model workflow and example mass spectra for a mixed yeast and human sample containing interference.

FIG. 4 provides analysis of the precursor purity model and quantitative accuracy model samples with either HCD $MS^2$ or mass spectrometry analysis utilizing gas-phase purification via PRT (referred to in the Figure as "QuantMode"). Panel A of FIG. 4 shows distribution of precursor purity as measured by examining reporter tag 126 (yeast) and 131 (human) for yeast-identified sequences using either HCD MS2 or QuantMode. Panel B of FIG. 4 shows analysis of quantitative accuracy via HCD $MS^2$ (left), HCD $MS^2$ with filtering (middle), and QuantMode (right). The dashed horizontal line indicates the true ratio while boxplots indicate the median (stripe), the 25th to 75th percentile (interquartile range, box), 1.5 times the interquartile range (whiskers), and outliers (open circles). The number of quantified yeast PSMs (A and median ratio are given for each method.

Figure 5:
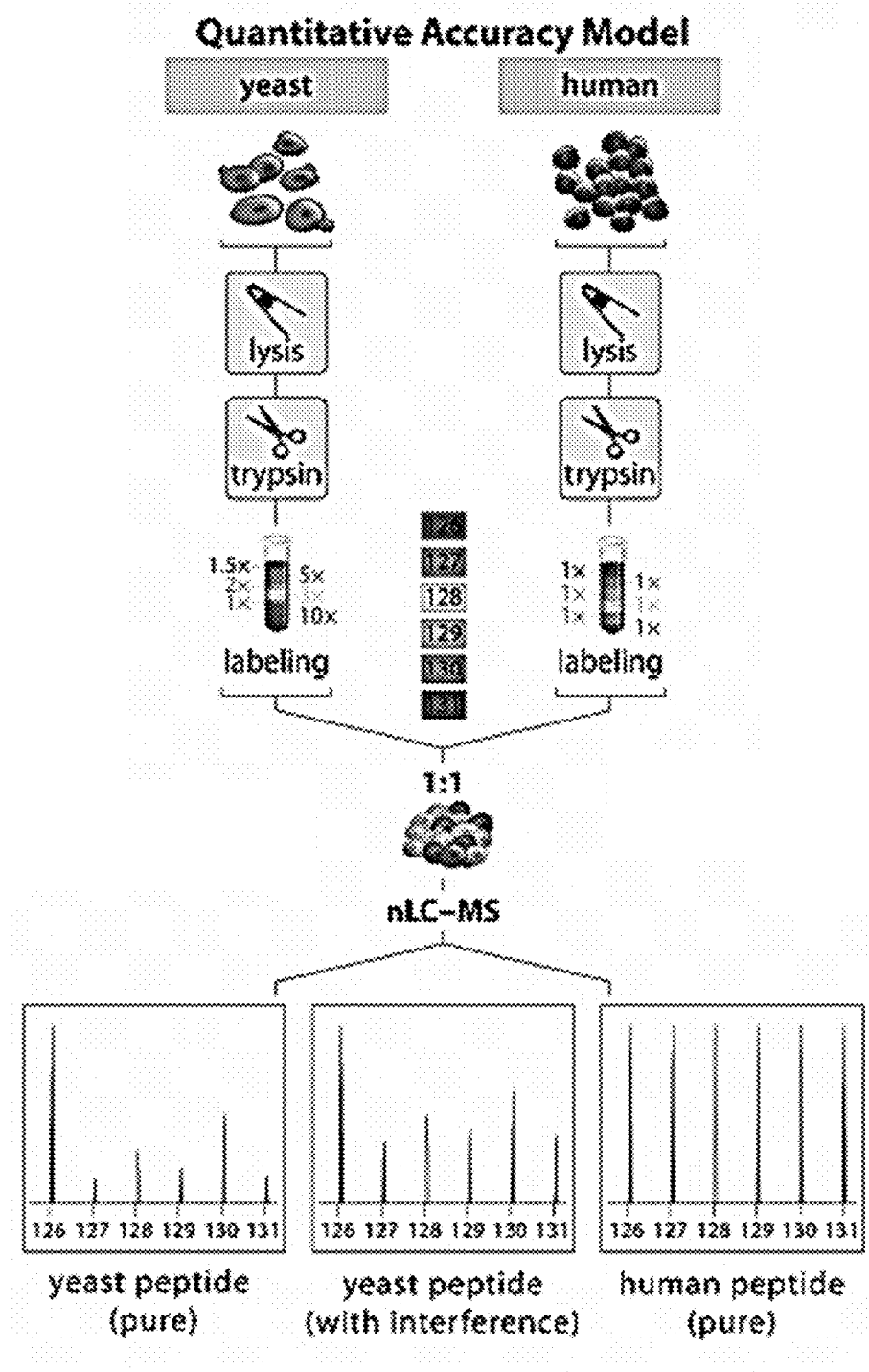
FIG. 5 provides comparative analysis of precursor purity model and quantitative accuracy model samples using either higher-energy collision dissociation mass spectrometry analysis (HCD $MS^2$), or mass spectrometry analysis utilizing gas-phase purification as described in an embodiment of the present invention (referred to in the Figure as "QuantMode"). Panel A provides a distribution of precursor purity as measured using either HCD $MS^2$ or QuantMode. Panel B provides analysis of quantitative accuracy via HCD $MS^2$ (left), HCD $MS^2$ with filtering (middle), and QuantMode (right).
Figure 6:
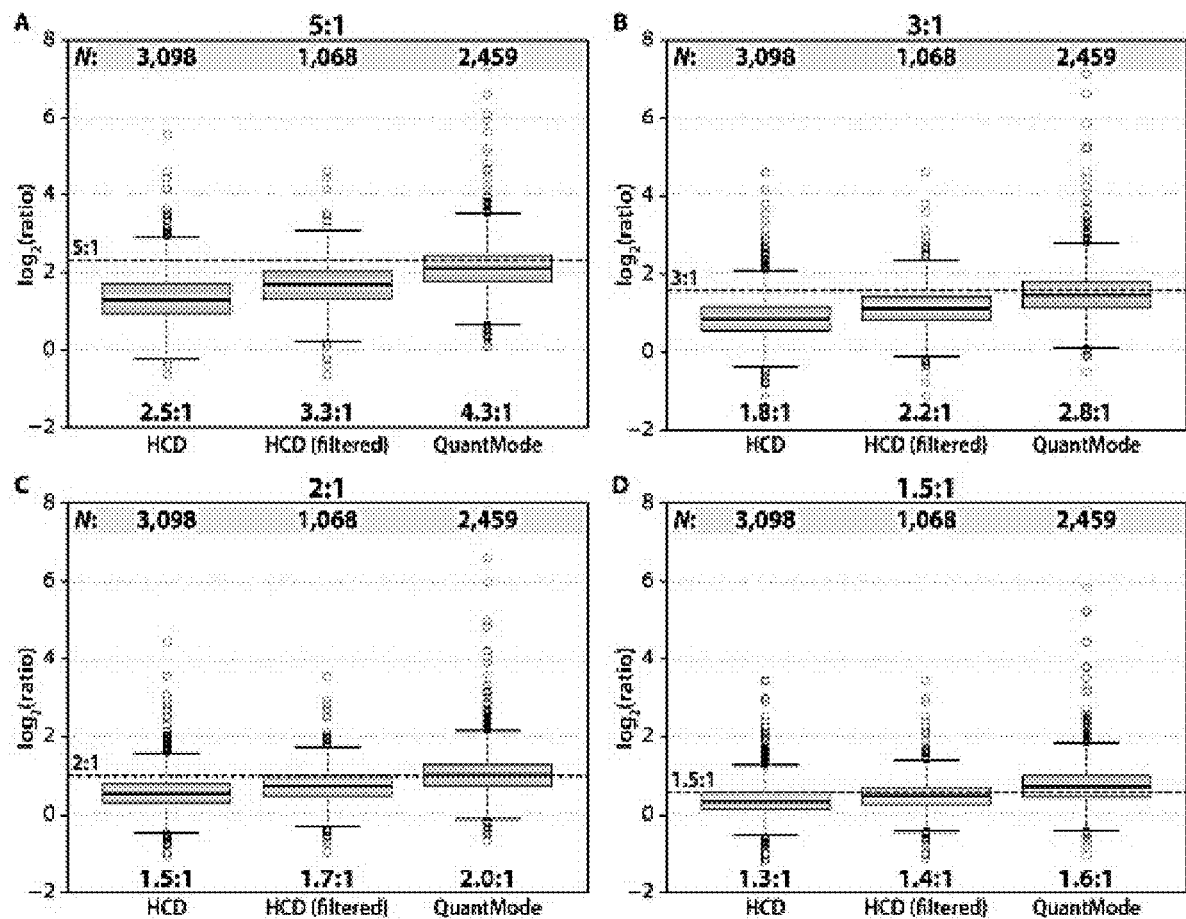
FIG. 6 provides plots showing analysis of the quantitative accuracy model sample for true ratios of 5:1 (panel A), 3:1 (panel B), 2:1 (panel C) and 1.5:1 (panel D).

To address what effect this prevalent interference has on isobaric tag-based quantification, a quantitative accuracy model, shown in FIG. 5, was created by labeling yeast peptides with TMT 6-plex tags (m/z 126-131) and combining them in ratios of 10:1:3:2:5:1.5. This sample was combined with an equal mass of tryptic human peptides also labeled with TMT 6-plex (m/z 126-131) but mixed in ratios of 1:1:1:1:1:1. By examining reporter ion ratios in yeast peptide spectra, the degradation of quantitative accuracy was assessed. Because this mixture was analyzed directly with nanoflow liquid chromatography-MS/MS (nLC-MS/MS), without prior fractionation, the experiment tested the technology in a worst-case interference scenario. Shockingly, the yeast 10:1 mix was measured at 4.4:1-a 2.3-fold underestimation or a 66% relative error, as shown in FIG. 6, furthest left boxplot in panel B; other similar ratios are shown in FIG. 6, panels A-D. These experiments both illuminate the extent and repercussion of precursor interference and provide an excellent metric with which to gauge improvement.

As shown in FIG. 6 (analysis of the quantitative accuracy mode/sample), boxplots display results for HCD $MS^2$ (left), HCD $MS^2$ with filtering (middle) or QuantMode (right) at (a) 5:1, (b) 3:1, (c) 2:1, and (d) 1.5:1 ratios. The dashed horizontal line indicates the true ratio while boxplots indicate the median (stripe), the 25th to 75th percentile (interquartile range, box), 1.5 times the interquartile range (whiskers), and outliers (open circles). The number of quantified yeast PSMs (A and median ratio are given for each method.

As seen in FIG. 6, QuantMode provided significantly more accurate results than both HCD $MS^2$ and HCD $MS^2$ with filtering.

Effects of Narrowing the Isolation Window and Interference Filtering in HCD $MS^2$ Several strategies have been proposed for the elimination of precursor interference in isobaric tag quantitation. These methods include: narrowing the precursor isolation window, rejecting precursor isolation windows containing impurities above a certain threshold, and performing an extra fragmentation ($MS^3$) event on the most intense $MS^2$ fragment ion prior to mass analysis of the reporter region ($MS^3$). One possible approach to reduce the impact of interference is to simply narrow the width of the $MS^2$ isolation window (without modifying any of the mass-to-charge ratios) so that fewer contaminant ions are present during precursor activation. Application of this concept, however, produced only minor improvements. It should also be noted that isolation efficiency is reduced as window widths narrow, resulting in fewer identifications (nearly 50% from 3 to 1 Th; 3,348 to 1,723 yeast PSMs).

Figure 7:
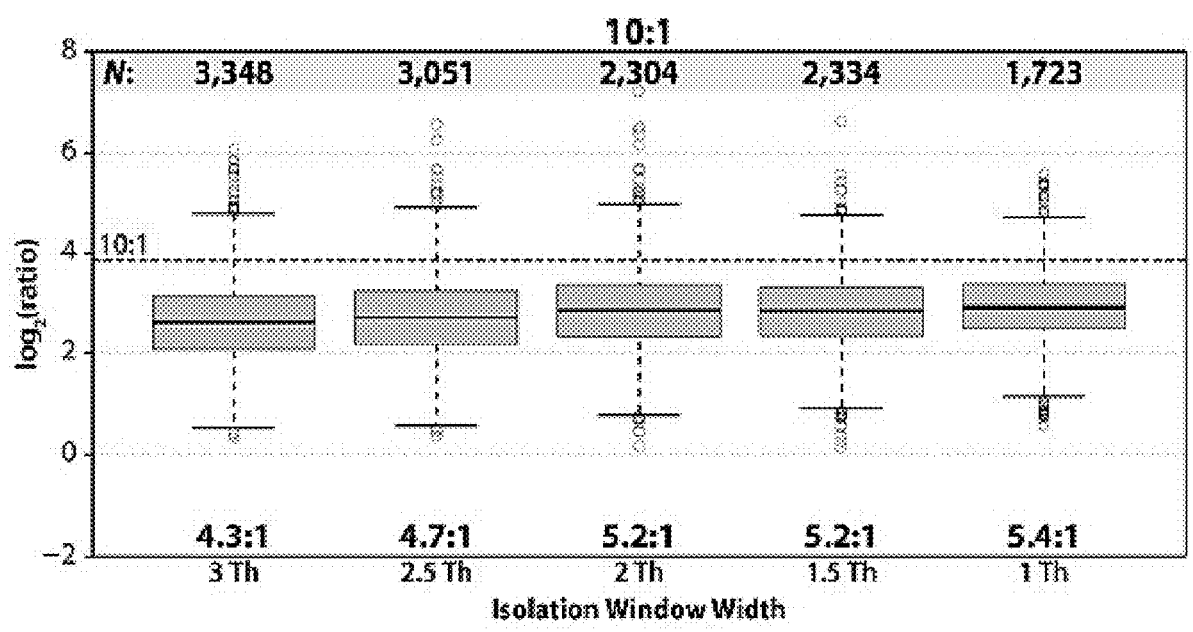
FIG. 7 provides a plot showing quantitative accuracy as a function of precursor isolation width.

As shown in FIG. 7 (quantitative accuracy as a function of isolation width), the 10:1 ratio of the quantitative accuracy model sample was analyzed by HCD $MS^2$ with decreasing precursor isolation width. The dashed horizontal line marks the true ratio of each plot (10:1). As shown in FIG. 7, the width of the isolation window (which only selected precursor ions within 1 Th to 3 Th mass-to-charge ratios of the target ion) was compared at widths of 3 Th, 2.5 Th, 2.0 Th, 1.5 Th and 1.0 Th. However, the 10:1 mix was still only measured at 4.3:1 to 5.4:1 using HCD $MS^2$. The number of yeast PSMs (n) and median ratio are listed beneath their respective boxplot.

Another strategy is to reject quantitative information from precursors having interference above a specified threshold. For the above dataset, for example, a post-acquisition filtering algorithm was used to remove MS/MS spectra if the precursor's purity was below 75% within the 3 Th $MS^2$ isolation window of the preceding $MS^1$ spectrum. As shown in FIG. 4, middle boxplot of panel B, this technique marginally improves quantification (to 6.2:1), but comes at the expense of 66% of the data: 3,098 versus 1,068 quantified PSMs. Though performing this process in real time boosts quantifiable PSMs, the improvement in quantification remains subtle. These data evince that background contaminants are not always detectable in $MS^1$. It is concluded that none of these avoidance-based strategies are wholly satisfactory and that interference is an omnipresent quantitative limitation.

Gas-Phase Purification Using Proton Transfer Ion-Ion Reactions (PTR)—QuantMode Scan Function A fresh approach is to combat interference directly via gas-phase purification: that is, to de-convolve the co-isolated contaminants from the precursor in m/z space by manipulating either mass or charge before performing a second isolation. Expedient proton-transfer ion/ion reactions (McLuckey, S. A. & Stephenson, J. L. *Mass Spectrom. Rev.* 17, 369-407 (1998); Reid, G. E., Shang, H., Hogan, J. M., Lee, G. U. & McLuckey, S. A. *J. Am. Chem. Soc.* 124, 7353-7362 (2002)) efficiently reduce ion charge state and integrate easily into higher order instrument scan methods. Consider a doubly charged precursor at 500 Th co-isolated with a triply charged contaminant also at 500 Th. Following PTR, the precursor is now positioned at m/z 999 (+1 charge state), while the interfering species is moved to m/z 749.5 (+2 charge state). Subsequent isolation of m/z 999 yields a purified precursor population from which to generate accurate quantification. Contaminants having z identical to the precursor are still spread in m/z space; for example, a +2 interference at m/z 501 will be transformed to m/z 1001 and effectively eliminated from the second isolation window (997.5-1000.5).

Figure 8:
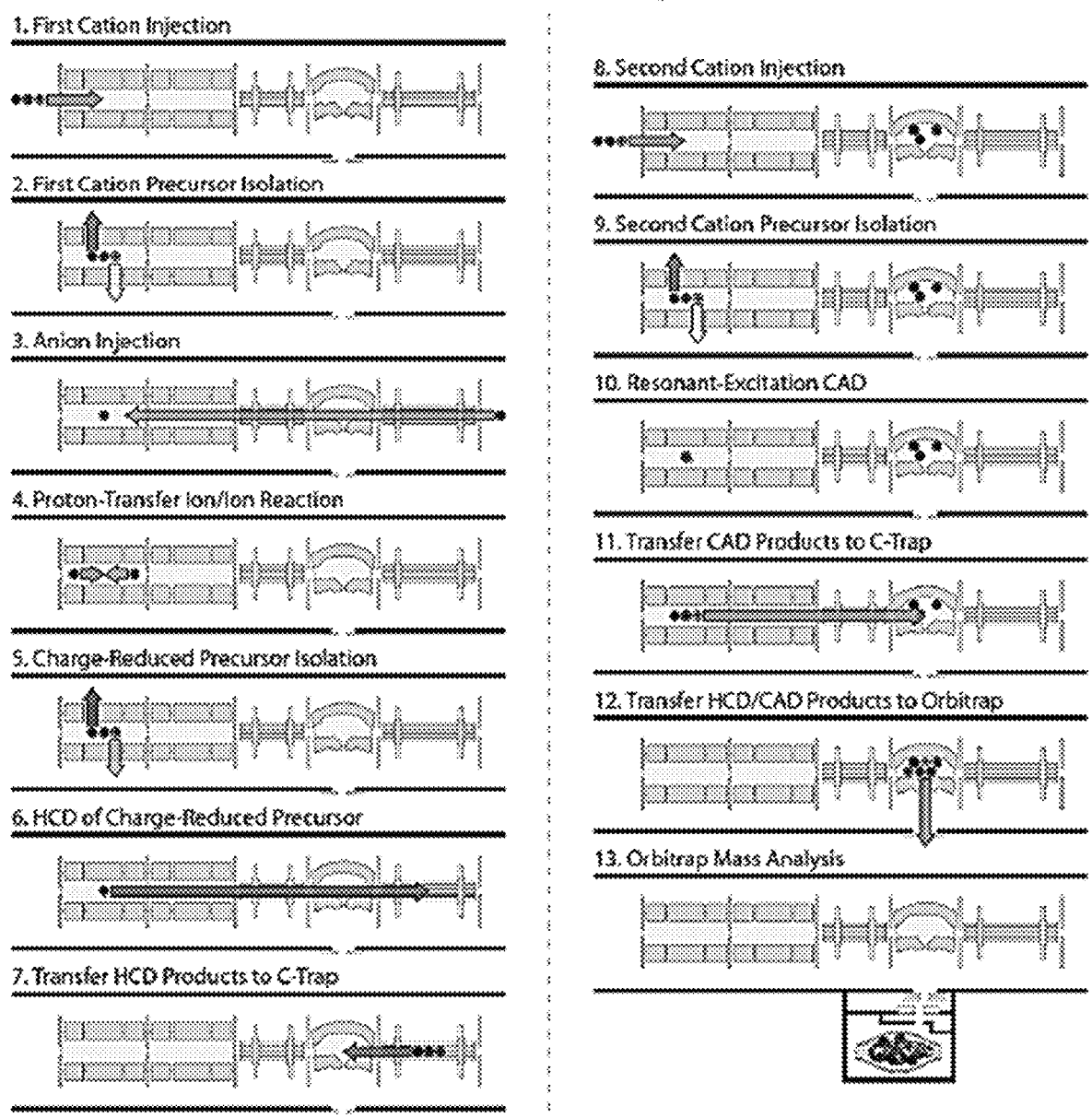
FIG. 8 provides an overview of steps in the QuantMode scan function.

To evaluate this idea, a scan function was devised comprising the following steps and automated by instrument firmware code modification as shown in FIG. 8: (1) first cation injection into a quadrupole linear ion trap (QLT), (2) first cation precursor isolation (also in the QLT), (3) anion injection (QLT), (4) proton transfer ion-ion reaction (QLT), (5) charge-reduced precursor isolation (QLT), (6) higher-energy collision dissociation (HCD) of the charge-reduced precursor (within the HCD cell), (7) transfer of HCD products (into the c-trap), (8) second cation injection (into the QLT), (9) second cation precursor isolation (QLT), (10) resonant-excitation collision-activated dissociation (CAD) (QLT), (11) transfer CAD products (c-trap), (12) transfer HCD/CAD products (orbitrap), and (13) mass analysis of reporter and sequence ions together (orbitrap). This mass spectrometry method using PRT was named QuantMode. The typical QuantMode scan is ~64% longer than a typical HCD scan, although markedly shorter than a full MS$^3$ experiment (~115% longer, not including a separate CAD scan for optimal identification).

Figure 9:
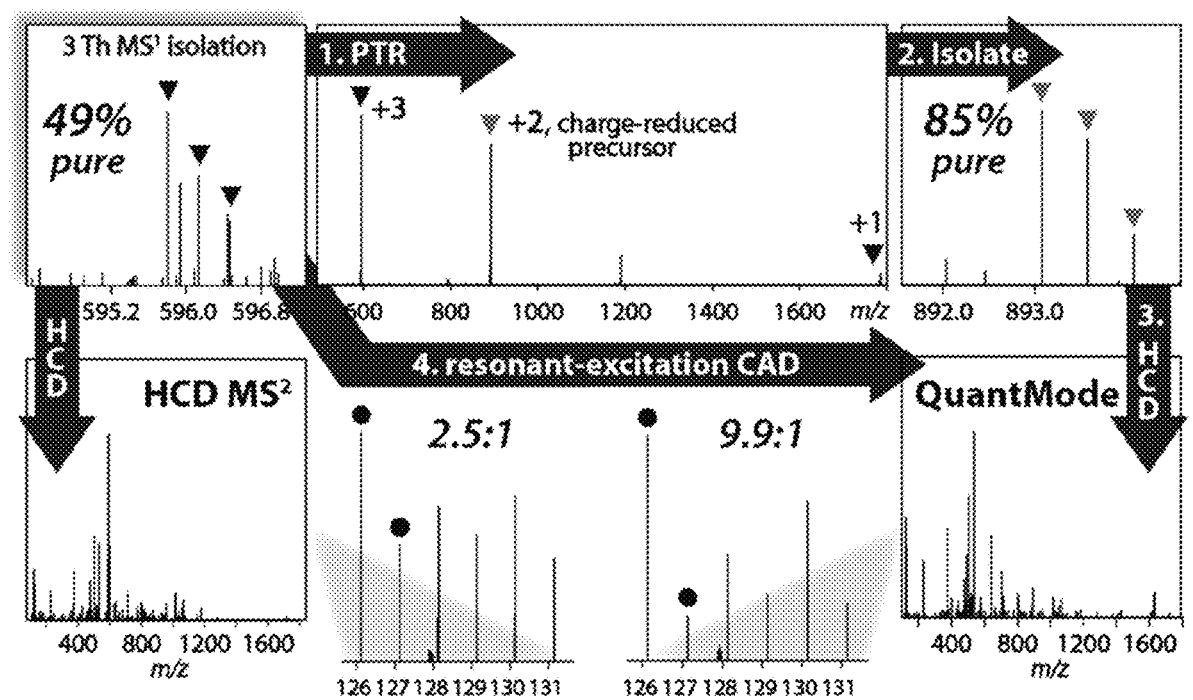
FIG. 9 provides an overview of QuantMode as applied to the quantitative accuracy model.

FIG. 9 provides an overview of the QuantMode scan function as applied to the quantitative accuracy model. A triply charged precursor at m/z 595.72 was isolated with a 3 Th window (upper left). The precursor isotopic cluster (▼) occupies only 49% of the total ion current in this region. QuantMode begins with PTR (step 1); isolation of the charge-reduced precursor (+2) purifies this target to 85% (step 2); HCD converts these purified precursors to reporter ions (step 3); resonant-excitation CAD follows re-injection/reisolation of the triply charged precursor (step 4). The HCD and CAD products are combined in the c-trap for orbitrap mass analysis (lower right panel). Juxtaposed against QuantMode is the conventional HCD MS$^2$ scan for this impure precursor (lower left panel). Lower middle insets display the reporter ion region (identical intensity scale) and the quantitative accuracy achieved by both approaches for the 10:1 ratio (●).

FIG. 9 displays the purifying effects of QuantMode. Examination of the 3 Th precursor isolation window (m/z595.72, +3) from the preceding MS$^1$ scan reveals extensive contamination—merely 49% purity, as shown in FIG. 9, upper left panel. This impurity does not hinder sequence identification upon HCD, shown in FIG. 9, bottom left panel (RINELTLLVQK, OMSSA expectation value 2×10$^{-10}$. It does, however, cripple quantitative accuracy: the 10:1 true value is recorded as 2.5:1, see FIG. 9, bottom center left panel. A 30 ms PTR step on this impure population effectively de-convolves the target with high efficiency (~45% for +3→+2), see FIG. 9, top middle panel. The doubly protonated precursor (893.08 Th) is then isolated from the contaminants (85% purity; see FIG. 9, top right panel); note the mass analysis following PTR, while illustrative, is not necessary, as the precursor's charge-reduced m/z is easily calculated. This untainted charge-reduced precursor population is then dissociated under HCD conditions favorable to reporter ion generation, the products of which are stashed in the c-trap. Next, sequence-informative products are produced through re-injection of the original triply charged precursor (m/z595.72), isolation, and fragmentation in the QLT. After combination in the c-trap, the mixed ion population is mass analyzed in the orbitrap, see FIG. 9, bottom right panel. The QuantMode scan, like its HCD-only counterpart, yields a high-confidence match to the peptide sequence RINELTLLVQK (OMSSA expectation value 2×10$^{-8}$). Yet in stark contrast to the truncated 2.5:1 ratio, QuantMode obtains a 9.9:1 ratio virtually equivalent the expected 10:1, see FIG. 9, bottom right center panel.

Figure 10:
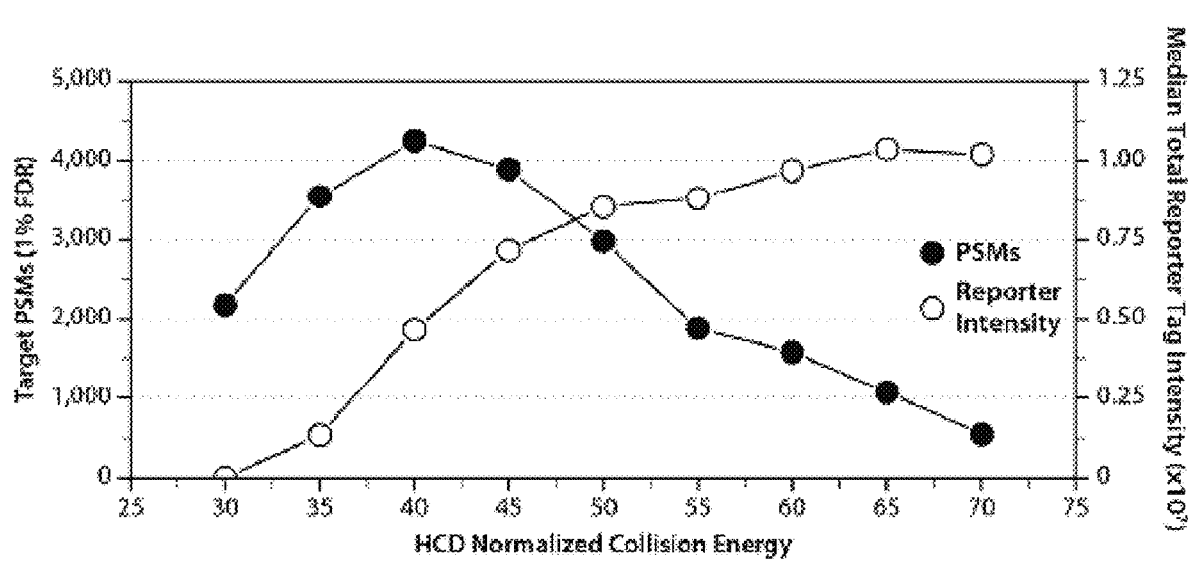
FIG. 10 provides a plot showing differences in optimal collision energies for identification and quantification.

The QuantMode scan affords manifold benefits in presenting the opportunity to conveniently decouple sequence and reporter ion generation. When dissociation conditions best facilitate reporter ion generation, spectral IDs suffer from poor sequence ion production, as shown in FIG. 10. First, then, independent control of dissociation parameters can simultaneously improve quantitative accuracy and spectral IDs. Second, decoupling permits the use of isobaric tagging with dissociation methods that are otherwise incompatible (e.g., resonant-excitation CAD, ECD/ETD, etc.) [Phanstiel, D., Zhang, Y., Marto, J. A. & Coon, J. J. *J. Am. Soc. Mass Spectrom.* 19, 1255-1262 (2008)]. Third, beyond decoupling benefits, QuantMode combines multiple disparate steps into a single scan to effectively reduce duty cycle.

As shown in FIG. 10 (differences in optimal collision energies for identification and quantification), a neat sample of trypsin-digested yeast proteins were analyzed at normalized collision energies (NCE) ranging from 30 to 70. The optimal number of target PSMs at 1% FDR (filled circles) are achieved at an NCE of 40, while the median total reporter tag intensity (open circles) peaks at 65 NCE.

To validate the efficacy of this method, the mixed organism models were reanalyzed with QuantMode. With the precursor purity model, purity improved from 68% to 88% among the same 1,297 precursors. Even more striking is the surge in ultrapure (99%) precursors—from 3% to 23%. Furthermore, this enhanced purity translated to quantitative accuracy. Applying QuantMode to analyze the quantitative accuracy model shifted the measured ratio from 4.4:1 with HCD to 8.5:1, much nearer to the true value of 10:1, as shown in FIG. 4, right boxplot of panel B. Other ratios are similarly present in FIG. 6. Unlike the avoidance-based strategies, such as narrowing the isolation window, QuantMode incurs only a minimal loss (21%, 3,098 to 2,459) in identified PSMs—all of which are now suitable for quantification.

In sum, these experiments demonstrate that isobaric tagging suffers from systemic loss of quantitative accuracy on account of pervasive and inherent precursor interference. The data acquisition method, QuantMode, described above mitigates this problem through gas-phase purification. QuantMode substantially increases quantitative accuracy without severely penalizing quantifiable identifications. In a non-laborious fashion, this method facilitates the critically important measurement of protein and PTM dynamics and performance of biological replicates for proper statistical treatment. Note this initial implementation will doubtless evolve to include a repertoire of dissociation methods, to improve both sequence and reporter ion generation, and to lessen duty cycle. Accordingly, QuantMode will render isobaric tagging a viable option for accurate, large-scale, multiplexed quantification.

Sample Preparation

For the above experiments, the following samples were prepared. Wild-type yeast (*Saccharomyces cerevisiae*) was grown in rich media to an OD$_{600}$ of 0.6. Cells were harvested and centrifuged for 10 min at 4° C. The resulting cell pellet was washed twice with sterile water and centrifuged at 1,088×g for 5 min. Lysis buffer of approximately three times the cell pellet volume was added. The Lysis buffer contained 8 M urea, 75 mM NaCl, 50 mM tris (pH 8), 10 mM sodium pyrophosphate, 100 mM sodium butyrate, complete mini ETDA-free protease inhibitor (Roche Diagnostics), and phosSTOP phosphatase inhibitor (Roche Diagnostics). The cells were lysed using a French press where the sample was pressed 3 times and centrifuged for 15 min at 23,708×g and 4° C.

Human H1 embryonic stem cells were maintained in a feeder-independent system, as previously described [Ludwig, T. E. et al. *Nat. Methods* 3, 637-646 (2006)]. Cells were harvested by individualizing for 10 min with an adequate volume of prewarmed (37° C.) 0.05% Tryp-LE to cover the culture surface. Following cell detachment, an equivalent volume of either icecold DPBS (Invitrogen) was added before collecting the cells. Cell pellets were subsequently washed twice in ice-cold PBS and stored at −80° C. Cells were lysed via sonication in lysis buffer containing 30 mM NaCl, 50 mM tris (pH 8), 2 mM $MgCl_2$, 50 mM NaF, 1 mM sodium orthovanadate, 6 mM sodium pyrophosphate, mini EDTA-free protease inhibitor (Roche Diagnostics), and phosSTOP phosphatase inhibitor (Roche Diagnostics).

For both yeast and human proteins, cysteine residues were reduced with DTT, alkylated using iodoacetamide, and digested in a two-step process (separately). Proteinase Lys-C (Wako Chemicals) was added at an enzyme:protein ratio of 1:100 and incubated for approximately 4 hr at 37° C. in lysis buffer. Samples were then diluted with 50 mM tris (pH 8.0) to a final urea concentration of 1.5 M and digested with sequencing-grade trypsin (Promega) at an enzyme:protein ratio of 1:50 at 37° C. overnight. Reactions were quenched using trifluoroacetic acid. Samples were desalted using C18 solidphase extraction columns (SepPak; Waters) and dried to completion. Yeast and human peptides were then split into six equal mass aliquots. TMT labeling was then performed with each of these aliquots, independently, as described previously [Wenger, C. D., Phanstiel, D. H., Lee, M. V., Bailey, D. J. & Coon, J. J. *Proteomics* (2011)].

Figure 3:
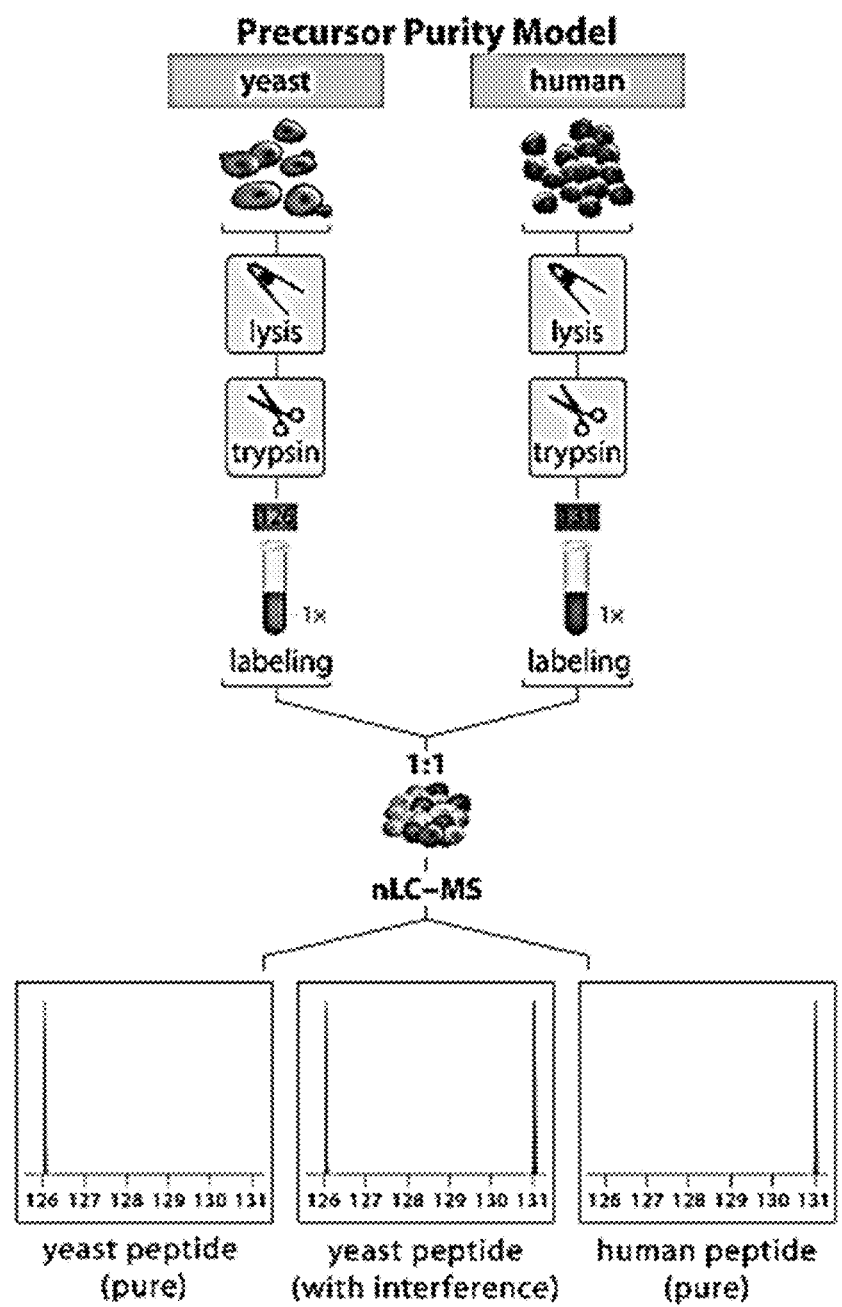
FIG. 3 provides a precursor purity model workflow and example mass spectra for a mixed yeast and human sample.

As shown in FIG. 3 (precursor purity model workflow), two populations of cells, yeast and human, were lysed and enzymatically digested with trypsin. Yeast peptides labeled with TMT 6-plex m/z 126 tag were mixed in equal mass with human peptides labeled with TMT 6-plex m/z 131 tag. Examining the presence of m/z 131 in yeast-exclusive peptides facilitates a quantitative calculation of precursor purity. As shown in FIG. 5 (quantitative accuracy model workflow), two populations of cells, yeast and human, were lysed and enzymatically digested with trypsin. Yeast peptides labeled with TMT 6-plex m/z 126-131 tags in ratios of 10:1:3:2:5:1.5, respectively, were mixed in equal mass with human peptides labeled with TMT 6-plex m/z 126-131 tags in ratios of 1:1:1:1:1:1. Including human peptide contamination in a yeast-exclusive PSM erodes quantitative accuracy.

The precursor purity sample shown in FIG. 3 comprised equal masses of a yeast aliquot labeled with the TMT 6-plex m/z 126 tag and a human aliquot labeled with the TMT 6-plex m/z 131 tag. The quantitative accuracy sample, shown in FIG. 5, comprised six yeast and six human aliquots labeled with TMT 6-plex m/z 126-131 tags. The yeast aliquots were mixed in the mass ratios 10:1:3:2:5:1.5, respectively; the human aliquots were mixed in the mass ratios 1:1:1:1:1:1, respectively. These samples were subsequently combined in equal masses.

Liquid Chromatography-Mass Spectrometry.

Online chromatography was performed with a NanoAcquity UPLC system (Waters) coupled to an ETD-enabled LTQ Orbitrap Velos (Thermo Scientific). Samples were loaded onto a precolumn (75 μm i.d., packed with 10 cm 5 μm Magic C18 particles; Michrom Bioresources, Inc.) for 10 min at 98:2 0.2% formic acid:acetonitrile with 0.2% formic acid at a flow rate of 1 μL/min. Samples were then eluted over an analytical column at a flow rate of 250 nL/min (50 μm i.d., packed with 25 cm 5 μm Magic C18 particles; Michrom Bioresources, Inc.) using a gradient with an initial steep rise to 8% B (acetonitrile with 0.2% formic acid) within 5 minutes, followed by a linear gradient to 30% B over 120 minutes and a ramped up to 70% B over 10 minutes and held for 5 minutes. The column was equilibrated with 2% B for an additional 25 min. The column-making procedure was previously described [Martin, S. E., Shabanowitz, J., Hunt, D. F. & Marto, J. A. *Anal. Chem.* 72, 4266-4274 (2000)].

Unless otherwise noted, the MS instrument method consisted of a data-dependent top-10 experiment with $MS^1$ resolution of 30,000 (orbitrap) followed either HCD $MS^2$ or QuantMode scans, mass analyzed in the orbitrap at 7,500 resolution. All isolation widths were 3 Th. HCD used a NCE setting of 45 for 30 ms. QuantMode employed PTR, the anions for which were generated by the commercial ETD source. For best PTR performance, we employed the nitrogen adduct of fluoranthene at m/z 216. Source conditions were optimized and all associated ion optics, using the instrument's automated tuning procedures, for this PTR anion.

Following accumulation of the precursor and reagent ions, the two populations were mixed via charge-sign independent trapping, as in an ETD scan. Reaction conditions were tailored to produce the maximal amount of the single charge reduction—e.g., the ion/ion reaction time for a triply charged precursor was set such that the maximum amount of doubly charge product ion was produced. For these experiments the following reaction times were employed: doubly charged precursors were reacted for 80 ms, triply charged precursors were reacted for 30 ms, quadruply charged precursors were reacted for 20 ms, and all precursors with five or more charges were reacted for 10 ms.

Following PTR, the resulting charge-reduced population was isolated and subjected to HCD (NCE 45, 30 ms). Note the charge-reduced species was used for determining HCD energetics, not the initial precursor. These products are then stored in the c-trap. Following HCD, but prior to mass analysis in the orbitrap, a second population of precursor ions (not charge reduced, i.e., impure) was injected into the high-pressure QLT, isolated, and subjected to resonant-excitation CAD (q-value 0.25, NCE 35, 10 ms). These products, which are devoid of the reporter region on account of the QLT low mass cutoff, were mixed with the HCD products in the c-trap and then simultaneously mass analyzed in the orbitrap.

AGC target values were 1,000,000 ($MS^1$), 50,000 (HCD), 200,000 (QuantMode: PTR), and 10,000 (QuantMode: resonant-excitation CAD). Note more recent data indicates a reduction in QuantMode PTR target to 50,000 results in neither significant loss of quantitative accuracy nor identification rate. Precursors of unknown or +1 charge state were rejected. Dynamic exclusion was enabled for 60 s after one precursor selection.

For the QuantMode overview experiment shown in FIG. 9, a data-dependent top-3 instrument method consisting of a 30,000-resolution $MS^1$ scan in the orbitrap was used followed by (1) normal HCD $MS^2$, (2) PTR $MS^2$, and (3) HCD $MS^3$ of the charge-reduced precursor followed by CAD $MS^2$ of the original precursor, in three separate scans, all mass analyzed at 7,500 resolution in the orbitrap. For the isolation width experiments shown in FIG. 7, standard HCD was used with $MS^2$ isolation widths from 3 Th to 1 Th in increments of 0.5 Th. For HCD NCE experiments shown in FIG. 10, standard HCD was used with NCEs of 30 to 70 in increments of 5. In this case only the yeast component of the quantitative accuracy sample was used with no human interference.

Data Analysis

The resulting data was processed with the COMPASS software suite [Wenger, C. D., Phanstiel, D. H., Lee, M. V., Bailey, D. J. & Coon, J. J. *Proteomics* (2011)]. OMSSA [Geer, L. Y. et al. *J. Proteome Res.* 3, 958-964 (2004)] searches were performed against a target-decoy [Elias, J. E. & Gygi, S. P. *Nat. Methods* 4, 207-214 (2007)] database containing both human (International Protein Index, 3.80) and yeast (*Saccharomyces* Genome Database, www.yeastgenome<dot>org, Feb. 3, 2011, "all" version including all systematically named open reading frames (ORFs), including verified, uncharacterized, and dubious ORFs and pseudogenes) proteins using an average precursor mass tolerance of ±5.0 Da and a monoisotopic product mass tolerance of ±0.01 Da. Carbamidomethylation of cysteines (+57 Da), TMT 6-plex on peptide N-termini (+229 Da) and TMT 6-plex on lysines (+229 Da) were specified as fixed modifications. Oxidation of methionine (+16 Da) and TMT 6-plex on tyrosines (+229 Da) were specified as variable modifications.

All analyses were independently filtered to 1% FDR at the unique peptide level. Peptides that could be derived from human proteins, regardless of enzymatic specificity and treating leucine and isoleucine as equivalent, were removed from consideration so only peptides of yeast origin were evaluated for quantitative analysis.

Post-acquisition precursor purity assessment was performed in real time with additional logic to the instrument firmware. The algorithm consists of iterating through all peaks within a window around the precursor. The window was enlarged by 20% relative to the actual isolation window, from 3 Th to 3.6 Th, to account for the empirical observation that species outside the isolation window (particularly on the low m/z side) could still be retained at significant levels. The peak m/z was converted to mass and compared to the precursor mass, assuming both species had the same charge. The nearest multiple of 1.00335 Da (carbon-13 mass minus carbon-12 mass, the main contributor to peptide isotopic peaks) was subtracted, and the remaining mass error was converted to parts per million (ppm). If the mass error was greater than ±25 ppm, the peak was judged as a precursor peak and its intensity was added to the precursor intensity sum. Once all peaks were considered, precursor purity was calculated as the precursor intensity sum divided by the total intensity.

EXAMPLE 2

The Role of Gas-Phase Purification in Quantitative Proteomics

The present methods are useful for providing mass spectrometric analysis achieving a number of goals particularly useful for the analysis of protein containing samples. First, the pervasive interference that occurs during isobaric tagging with proton transfer ion-ion reactions is eliminated. Additionally, the present methods are applicable in the context of the yeast environmental stress response (ESR). Yeast's manageable proteome and available copy per cell data make it an excellent tech development model, while the conserved stress response network makes it medically relevant.

To maximize biomedical impact, quantitative protoemics should be compatible with human tissues and biofluids. Multiplexing is likewise beneficial as it presents an expedient route to significance testing. Isobaric tagging meets these requirements, but is plagued by ubiquitous and debilitating interference. Such Interference, often undetectable in $MS^1$ scanning, is effectively combated by gas-phase purification with PTR. This innovative and creative use of PTR has broad biological significance and impact. Selection of the yeast ESR application is a fresh approach to technology development, as those experiments will generate guiding information for the subsequent biological study, which has relevance for research ranging from human disease to evolution.

Isobaric tagging offers a direct means to perform highly-multiplexed proteome quantification on ALL proteomic samples, including tissues and bio-fluids. The method, however, has not been widely adopted because of the widespread problem of precursor interference. [See Lu, R., F. Markowetz, R. D. Unwin, J. T. Leek, E. M. Airoldi, B. D. MacArthur, A. Lachmann, R. Rozov, A. Ma'ayan, L. A. Boyer, O. G. Troyanskaya, A. D. Whetton, and I. R. Lemischka, *Systems-level dynamic analyses of fate change in murine embryonic stem cells. Nature,* 2009. 462(7271): p. 358-U126]. Co-isolated species unintentionally contribute to the target's reporter ion signal, causing an overall repression of dynamic range and loss of quantitative precision.

An accurate, multiplexed method for quantitative analysis of cell lysates, tissues, and biofluids will greatly improve the biomedical impact of proteomics. The present approach seamlessly integrates PTR with ETD/CAD for accurate, high dynamic range, multiplexed quantification.

Experimental Design

Figure 12:
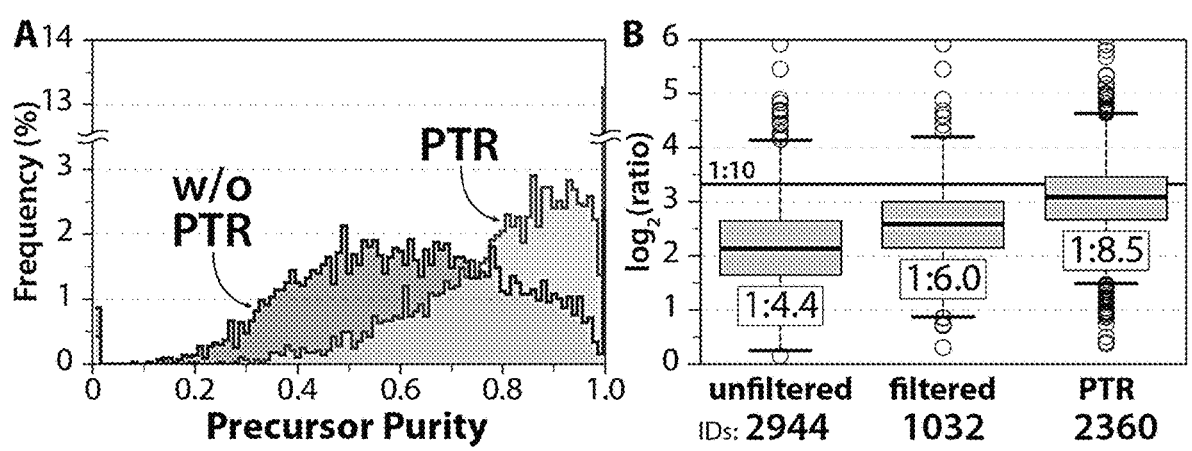
FIG. 12 provides a comparison of precursor purity observed in an isobaric tag experiment without proton transfer ion-ion reactions (PTR) vs. purity distribution following PTR (panel A). Panel B shows quantitative accuracy for an isobaric tagging experiment of yeast peptides mixed in a 1:10 ratio and contaminated with human interference at 1:1.

To document the extent of interference, peptides from a whole cell yeast lysate were labeled with a tandem mass tag (TMT) 126. These peptides were spiked with peptides from a digest of human proteins, which had been labeled with a TMT 131 tag. Following nHPLC-MS/MS, the MS/MS reporter regions of peptide precursors that were uniquely mapped to yeast were extracted. The 126:131 reporter signal ratio, therefore, provides a direct measure of contamination, as shown in FIG. 12, panel A. From these data, on average, only 55-60% of reporter region ion signal originates from the peptide being quantified. The impact of contamination on dynamic range is nothing short of astonishing, as shown in FIG. 12, panel B. Yeast peptides labeled either with TMT 126 or 127 are mixed in a 1:10 ratio. That sample was contaminated with human peptides carrying the same tags, but mixed in a 1:1 ratio. Now any yeast-identified peptide having human contamination will display an eroded 1:10 ratio. From FIG. 12, panel B (unfiltered column), the dynamic range is compressed from 1:10 to ~1:4.

Next, the region around the precursor m/z peak (±1.5 Da, the isolation range) in the $MS^1$ scan and tabulated all peaks within this region was examined. All MS/MS scans that had a detectable $MS^1$ contaminant peak that was ≥25% of the target's abundance were filtered out. The idea is that perhaps contamination can be detected and those scans eliminated from quantitative calculations. The filtered experiment reduced the number of quantifiable scans from 2,944 to 1,032 and only increased the measured ratio to 1:6.0, shown in FIG. 12, panel B, filtered column. Reduction of the isolation window width can only, at best, marginally improve the measurements. Further, effective isolation at a resolution better than 1.0 m/z is difficult. As seen in this data, the pervasive interference problem greatly handicaps the multiplexing potential offered by isobaric tags and that interfering species are often not detectable at the $MS^1$ level.

McLuckey et al. pioneered the field of ion-ion chemistry and have extensively described the use of PTR to manipulate ion charge states, purify populations, and simplify mass spectra. Here, it is proposed to use PTR to eliminate the interference associated with isobaric tagging. The idea is to use PTR to de-convolve the co-isolated contaminants from the precursor in m/z space, re-isolate the charge-reduced precursors, and then perform MS/MS to generate a pure population of reporter tags. Application of this approach to the mixture described above resulted in a near correct ratio of 1:8.5 with 2,360 identifications, shown in FIG. 12, panel B, PTR column. As an added benefit, the reporter tag ion production is now easily decoupled from sequence ion generation-called the chaser. For instance, the scan sequence (automated by control code modification) in FIG. 12, panel B (PTR) comprised: precursor selection (QLT), precursor purification (PTR, in QLT), isolation of the charge-reduced product (QLT), reporter tag generation and storage (HCD cell), precursor re-injection (QLT), precursor isolation (QLT), ion trap CAD (the chaser, QLT), injection of those products into the HCD cell, and mass analysis of reporter and sequence ions together (orbitrap). This sequence was automated by control code modification. With this approach, alternative fragmentation methods not fully compatible with isobaric tags (i.e., ETD or ion trap CAD) can be seamlessly woven in without loss of quantitative information. It also affords the opportunity to optimize tag production conditions irrespective of sequence ion generation. Finally, since +1 precursors are rarely encountered (ESI-LC-MS), the approach is applicable to nearly all eluents.

Continued development can be achieved via duty cycle improvement, reporter signal generation, implementation of PTR reaction in the ETD cell, and PTR reagent selection. Currently the PTR/HCD scan is ~30-40% longer than a standard HCD scan, though the implementation shows only a slight reduction in IDs from 2,944 to 2,360. This is strong performance and, considering that interference renders the quantitative data from the 2,944 HCD IDs essentially useless, the PTR/HCD method is already a powerful quantification tool. Because the identification information comes from a separate activation event, the chaser, PTR purification does not influence ID sensitivity. ID reduction can thus be attributed to duty cycle. The duty cycle can be improved by investigating PTR anions of m/z lower than the current m/z 216. Performing the PTR step within the ETD cell can further increase the reaction rate, but requires subsequent isolation of the PTR product in the QLT. Despite the resultant additional 10-15 ms and marginally decreased sensitivity (transfer losses), an overall savings of ~30-40 ms (20% duty cycle increase) is achieved. The proposed ETD cell does not necessarily afford isolation capability; as these modifications may in some instances require considerable effort and expense. Given the method's already strong performance and the proximity of the QLT, extending isolation capability to the ETD cell is not necessary.

As shown in FIG. 12, panel A: Measurement of precursor purity typically observed in an isobaric tag experiment ("w/o PTR" in the Figure) vs. purity distribution following PTR ("PTR" in the Figure). As shown in FIG. 12, panel B: Quantitative accuracy for an isobaric tagging experiment of yeast peptides mixed in a 1:10 ratio and contaminated with human interference at 1:1. PTR substantially improves quantitative accuracy (1:8.5) and still produces comparable identifications.

The present methods are also beneficial for inducing exclusive reporter tag formation. Increasing HCD energy does boost tag signal, but too much energy can negate any gains through scattering losses. Preliminary data indicates that IRMPD presents an attractive alternative; by using the AI-ETD laser, primary product ions have been effectively converted to reporter tag signals (at normal QLT operating pressures). In this experiment, the sum of the reporter signal was just over ⅔ the intensity of the initial product signal. Automating this experiment, even without further gains, would greatly boost quantitative accuracy and dynamic range via overall S/N improvement. Finally, the separation of reporter and sequence ion generation will enable the seamless introduction of ETD with isobaric tagging. To implement ETD a custom control code may be used to pass the ETD reagent through the ETD cell into the QLT for ion-ion reactions. This may be done because the ETD cell will be storing the reporter ions and cannot be used for ETD. Little reaction of the +1 reporter ions is anticipated for two reasons: (1) the reagents will be passing with high relative velocity and (2) reporter ions are singly charged and will not be particularly reactive on the time-scale of anion injection (~10 ms). The use of a data-dependent Decision Tree algorithm to automatically integrate ETD and CAD for shotgun proteomics has been previously described. Such algorithms can used to integrate other mass spectrometry methods with PTR. Standard peptide mixtures, introduced with infusion, can be used to test reaction rates, conversion efficiencies, ETD implementation, and reporter tag generation via IRMPD. After optimization, large-scale testing by nLC-MS analysis of complex mixtures of yeast peptides can be conducted, and model interference (as described above) can be conducted to evaluate the efficacy of the purification process. Comparison of the PTR approach to the standard HCD method will provide duty cycle benchmarking.

The central outcome is a multiplexed quantification method with high dynamic range and accuracy. The use of PTR chemistry solves a longstanding problem with isobaric tagging. By enabling routine multiplexing and compatibility with human tissues and biofluids, the approach can have substantial biomedical impact.

EXAMPLE 3

New QuantMode Characteristics

The QuantMode scan sequence is designed to be able to be used on ETD-enabled instruments, such a LTQ Velos Orbitrap instrument. Briefly, this scan sequence comprises: precursor selection, precursor gas-phase purification, isolation of the charge-reduced products, reporter tag generation and storage (such as in a dedicated beam-type collision cell), precursor re-injection, precursor isolation (QLT), ion trap CAD (QLT), injection of CAD products into the dedicated collision cell, and mass analysis of reporter and sequence ions together. This scan progression not only produces a purified reporter tag region, but also decouples reporter tag ion production from sequence ion generation to enable a boost in reporter tag signal without the loss of key sequencing ions. The method was validated using a mixed organism model which maximized the occurrence of precursor interference. Using this model, QuantMode was found to produce significant improvements in both dynamic range and quantitative accuracy, with minimal losses in peptide identifications.

Figure 13:
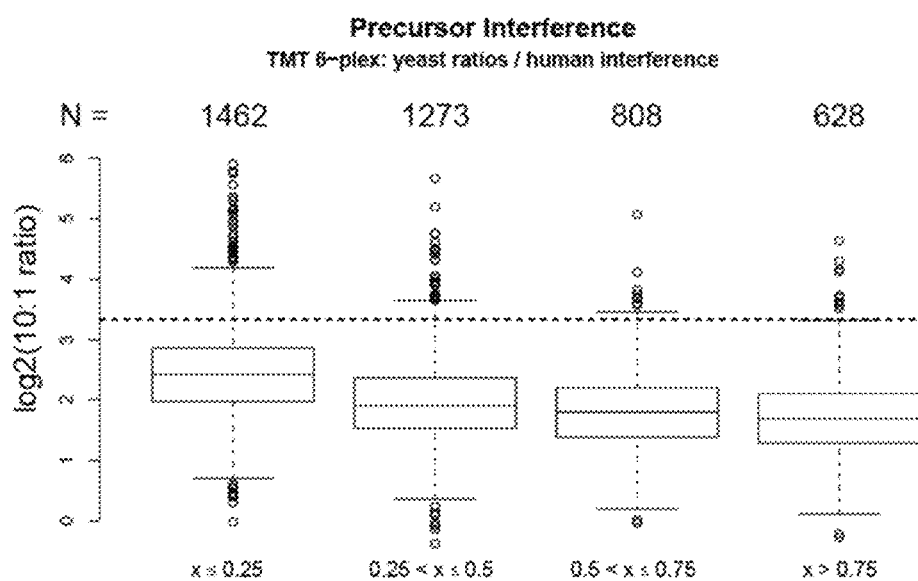
FIG. 13 provides a plot of the measured isobaric tag ratio as a function of detectable precursor interference in the MS isolation window (panel A). Even precursors having highly pure (>25%) target precursors have measured ratios much lower than expected (dotted line). Panel B shows isobaric tag ratios as a function of target precursor intensity. Targets of high intensity provide ratios closest to the true value (dotted line).
Figure 13:
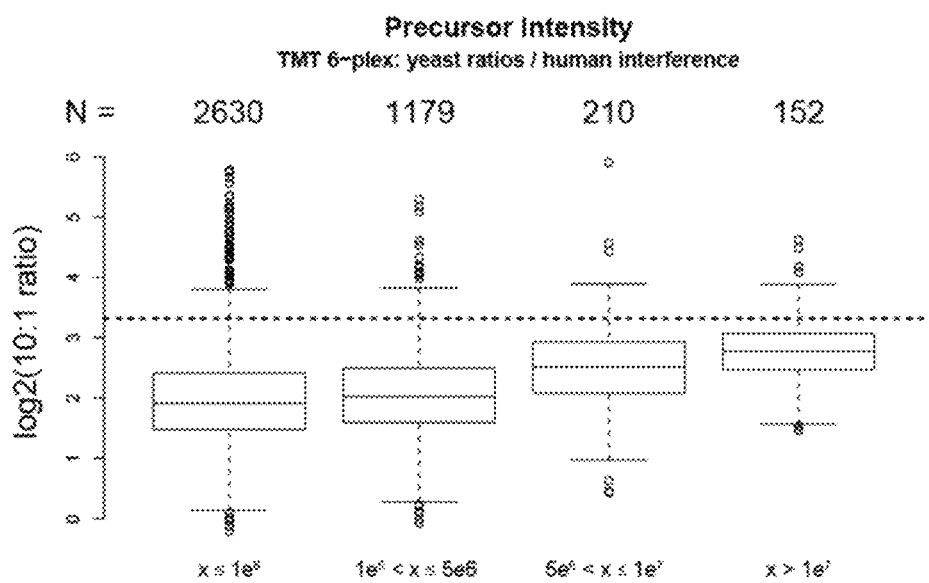

FIG. 13 (panel A) provides a plot of the measured isobaric tag ratio as a function of detectable precursor interference in the MS isolation window. Even precursors having highly pure (>25%) target precursors have measured ratios much lower than expected (dotted line). FIG. 13 (panel B) provides plots of measured isobaric tag ratios as a function of target precursor intensity. Targets of high intensity provide ratios closest to the true value (dotted line).

Figure 14:
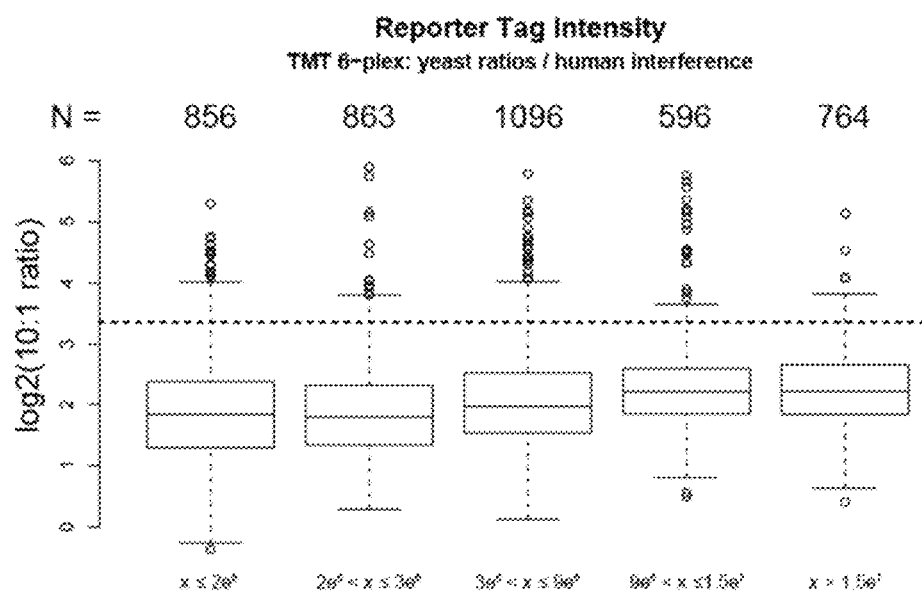
FIG. 14 provides isobaric tag ratios as a function of reporter tag intensity (panel A). Tags of high intensity provide ratios closest to the true value (dotted line). Panel B shows isobaric tag ratios as a function of precursor charge state. Tags of high charge states provide ratios furthest from the true value (dotted line).
Figure 14:
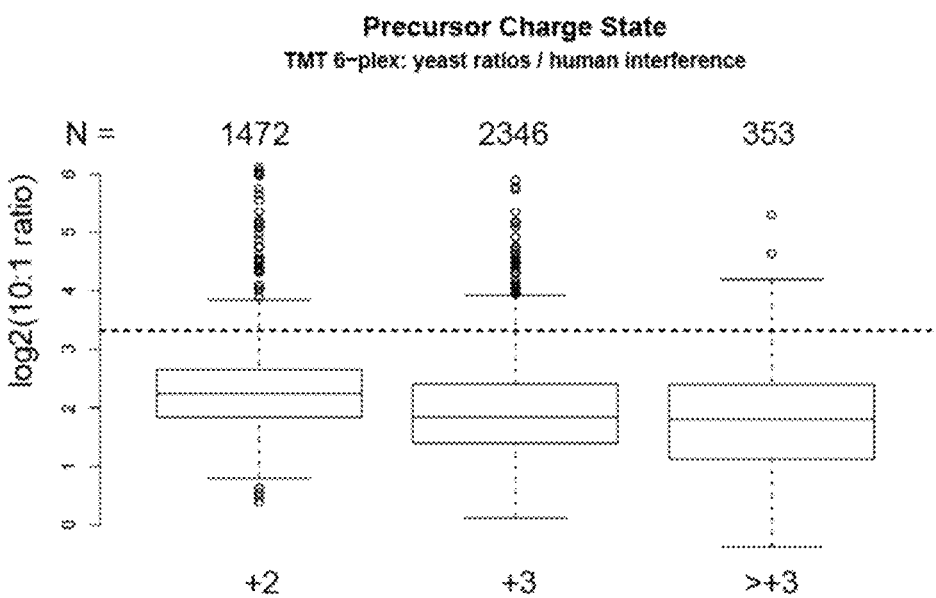

FIG. 14 (panel A) provides plots of measured isobaric tag ratios as a function of reporter tag intensity. Tags of high intensity provide ratios closest to the true value (dotted line). FIG. 14 (panel B) provides plots of measured isobaric tag ratios as a function of precursor charge state. Tags of high charge states provide ratios furthest from the true value (dotted line).

Figure 15:
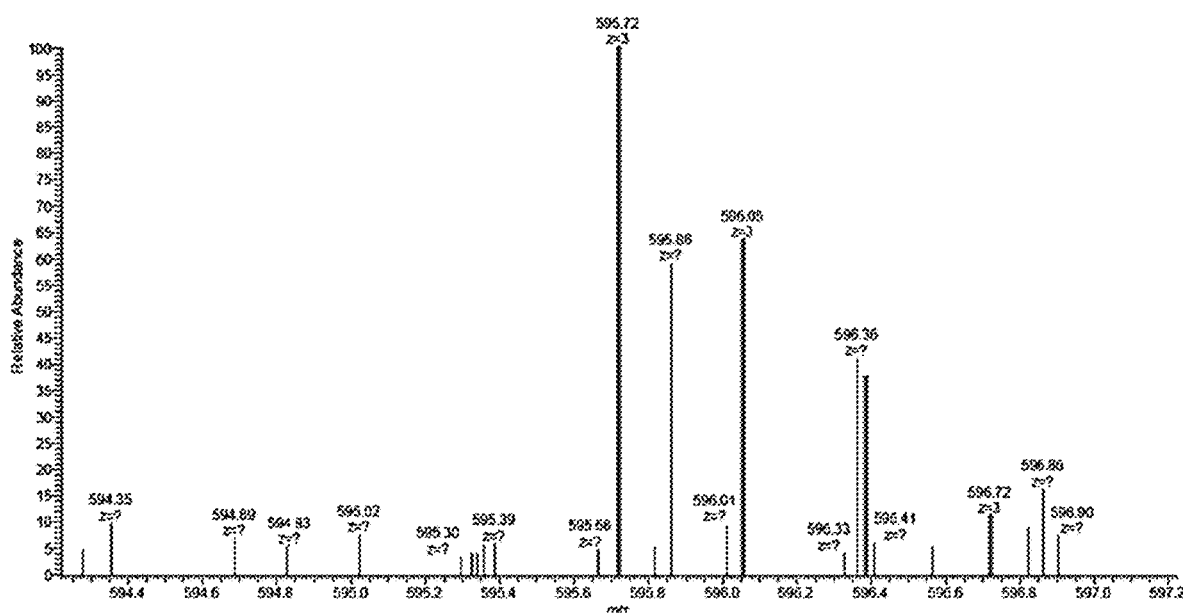
FIG. 15 provides a spectrum of an isolation window showing an isotopic cluster of a peptide precursor cation of a peptide having the sequence RINELTLLVQK. Interfering species are present.

FIG. 15 provides a spectrum corresponding to an isolation window showing the isotopic cluster of the peptide precursor cation of the peptide having the sequence RINELTLL-VQK. The spectrum shown in FIG. 15 shows the presence of interfering species.

Figure 16:
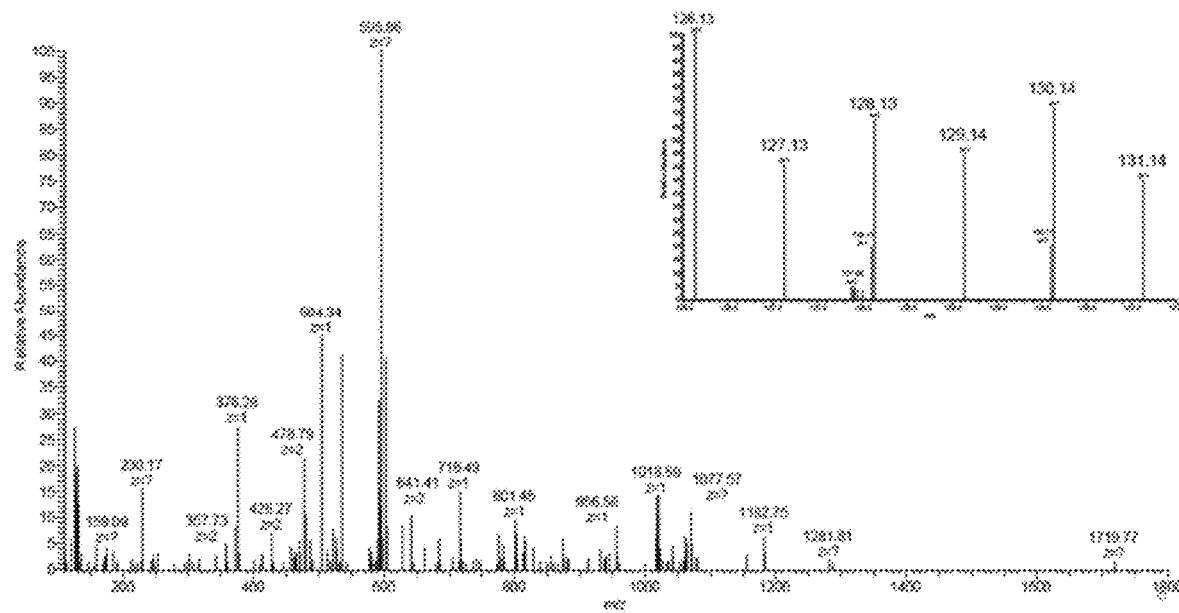
FIG. 16 provides an MS/MS spectrum of the precursor region shown in FIG. 14. Reporter tags at m/z 126 and 127 should have ratio of 10:1. They are measured at 2.5:1.

FIG. 16 provides a MS/MS spectrum of the precursor region shown in FIG. 15. Reporter tags at m/z 126 and 127 should have ratio of 10:1. They are measured at 2.5:1.

Figure 17:
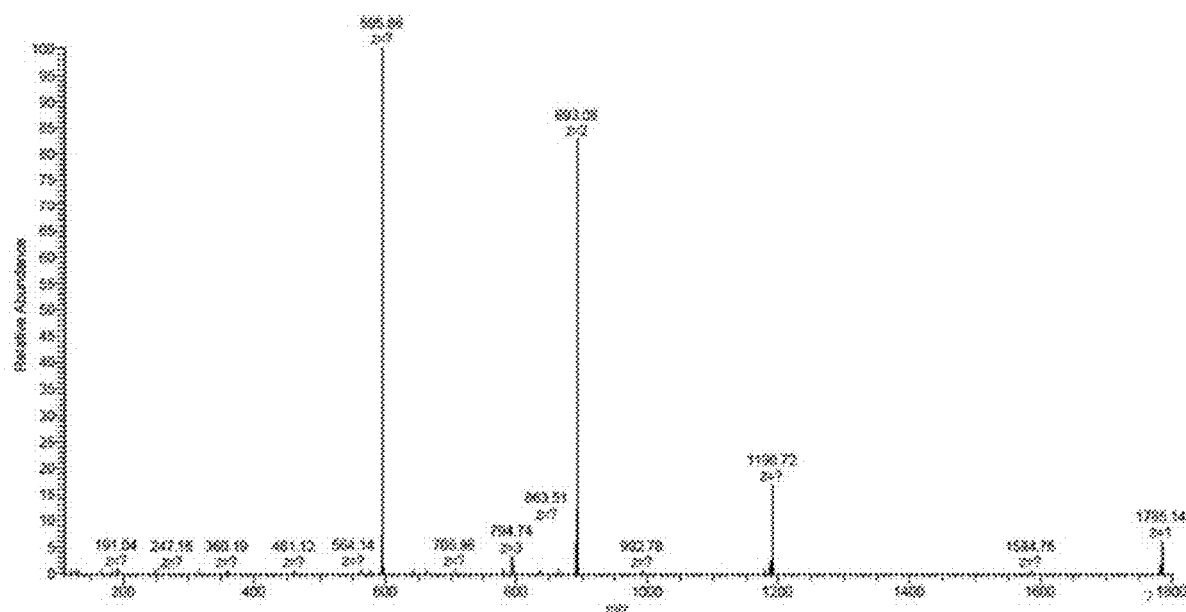
FIG. 17 provides a spectrum of the reaction of the isolation window shown in FIG. 14. Multiple products are detected from both the target peptide and contaminating species.

FIG. 17 provides a spectrum corresponding to the reaction of the isolation window shown in FIG. 15. Multiple products are detected from both the target peptide and contaminating species.

Figure 18:
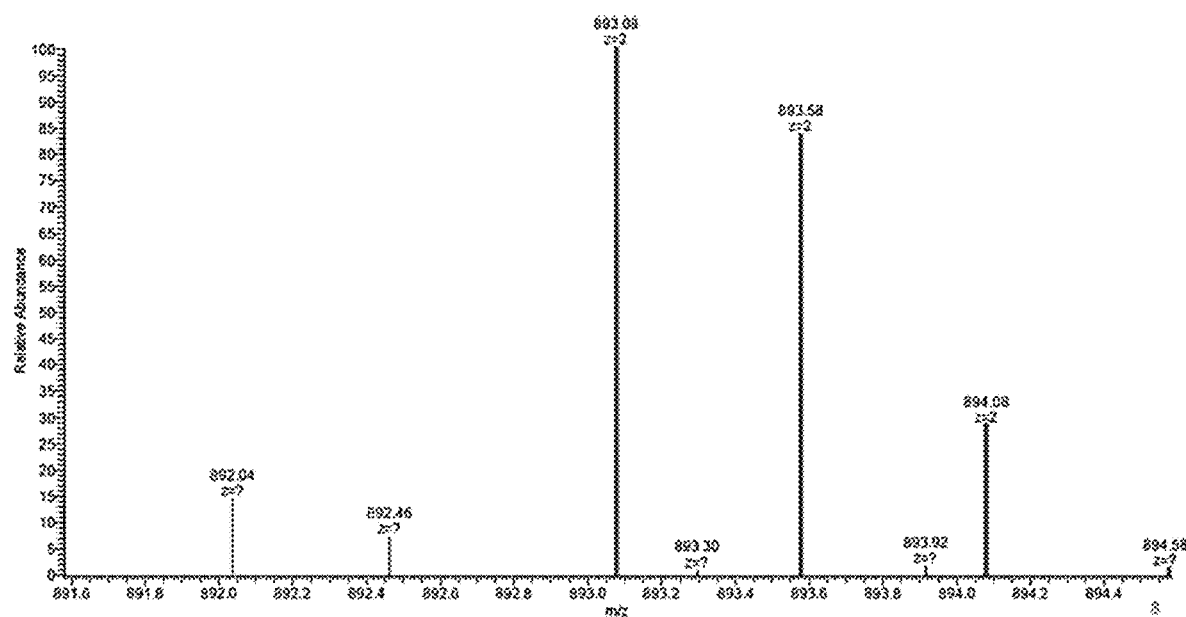
FIG. 18 provides a spectrum of an isolation window showing a purified precursor peptide cation population following a proton transfer reaction of the isolation window shown in FIG. 14.

FIG. 18 provides a spectrum corresponding to the isolation window showing a purified precursor peptide cation population following a proton transfer reaction of the isolation window shown in FIG. 15.

Figure 19:
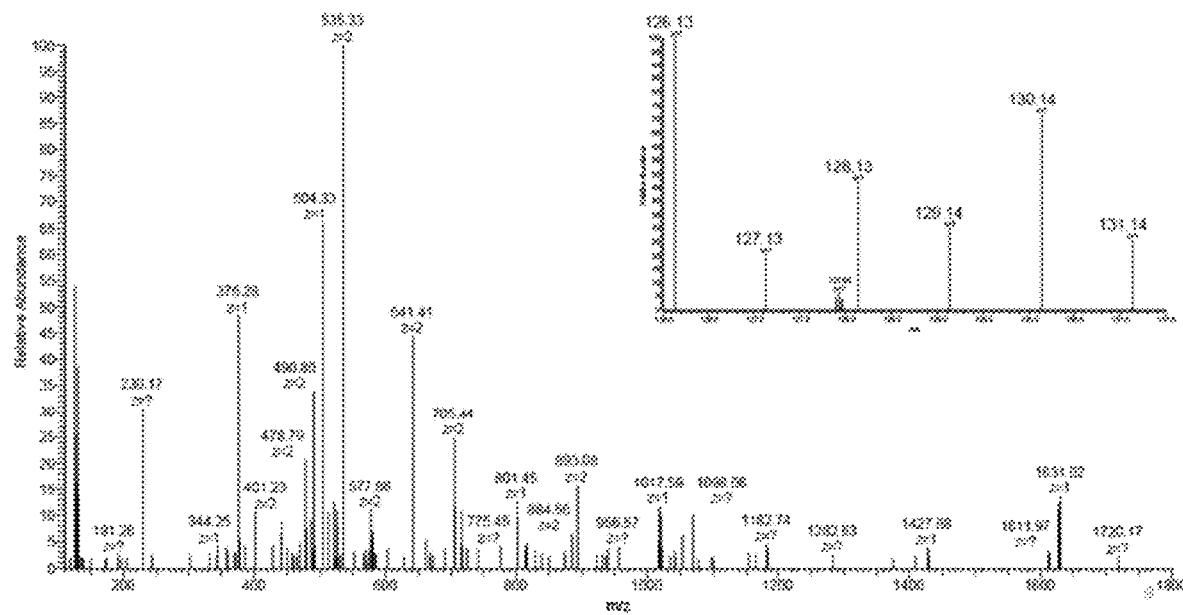
FIG. 19 provides a product ion spectrum following dissociation of the isolated charge-reduced target precursor population. The reporter signal is now measured at 9.9:1 and is almost identical to the true value of 10:1.

FIG. 19 provides a product ion spectrum following dissociation of the isolated charge-reduced target precursor population. Note the reporter signal is now measured at 9.9:1 and is almost identical to the true value of 10:1.

Figure 20:
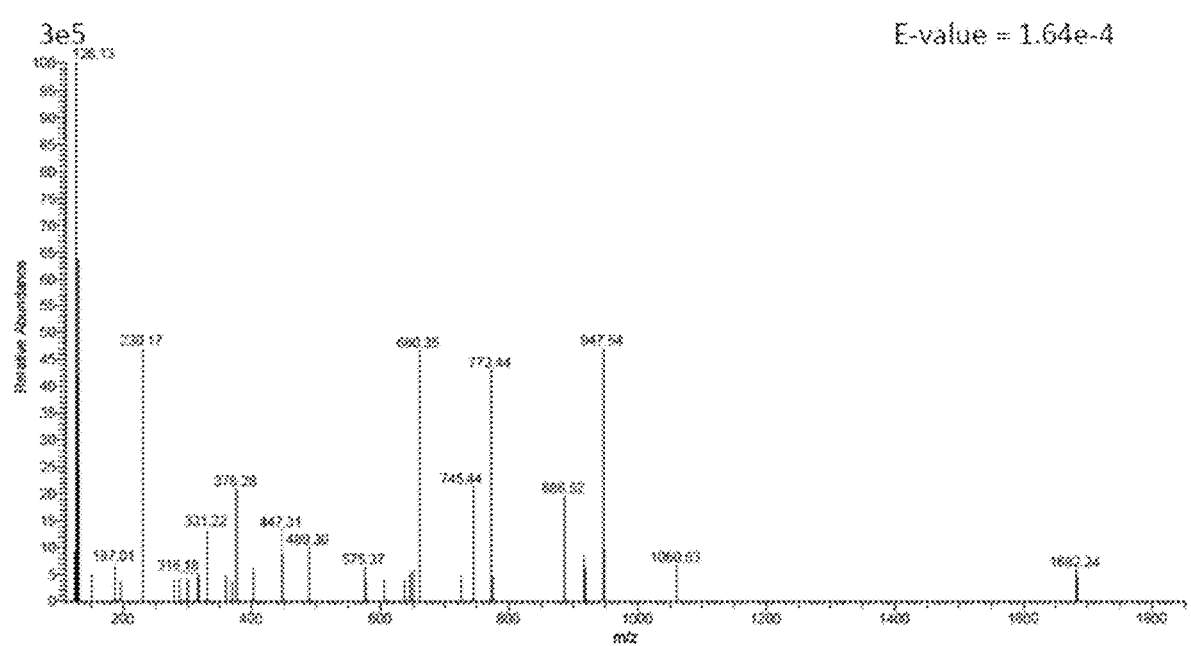
FIG. 20 provides a product ion spectrum following isolation and dissociation of the charge-reduced precursor of the peptide having the sequence TASGNIIPSSTAGAAK.

FIG. 20 provides a product ion spectrum following isolation and dissociation of the charge-reduced precursor of the peptide having the sequence TASGNIIPSSTAGAAK.

Figure 21:
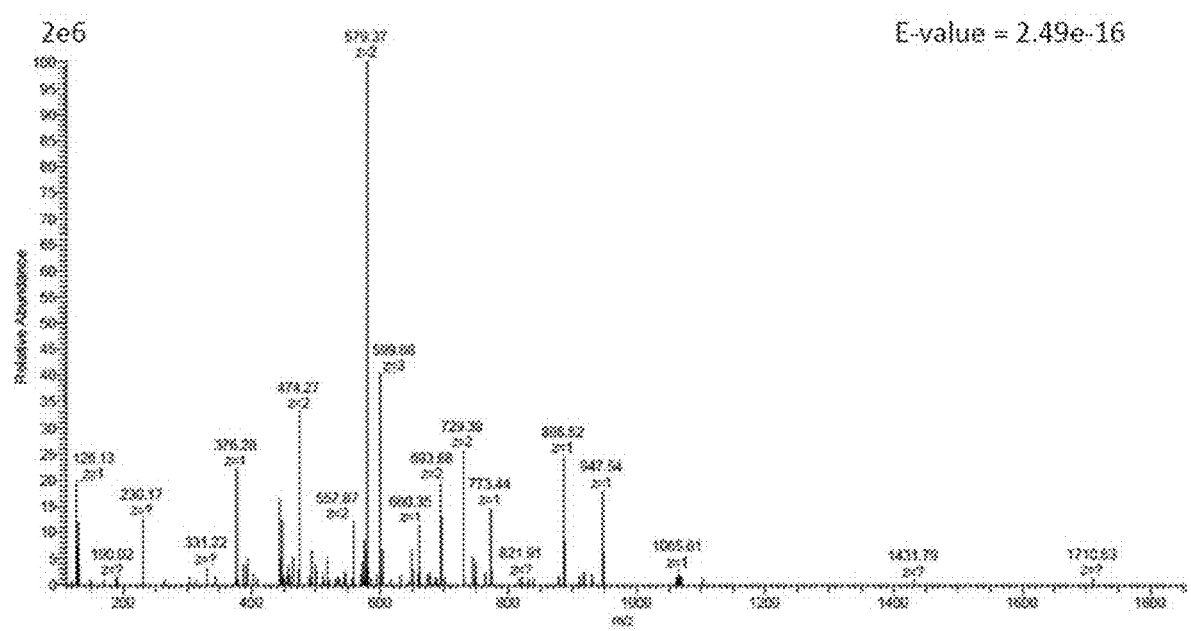
FIG. 21 provides a product ion spectrum following (a) isolation and dissociation of the charge-reduced precursor of the peptide having the sequence TASGNIIPSSTAGAAK, and (b) fragmentation of the isolated non charge-reduced precursor and combination with the products generated in step 1. Significantly more sequence informative ions are present in this spectrum.

FIG. 21 provides a product ion spectrum following (1) isolation and dissociation of the charge-reduced precursor of the peptide having the sequence TASGNIIPSSTAGAAK and (2) fragmentation of the isolated non charge-reduced precursor and combination with the products generated in step 1. Note significantly more sequence informative ions in this spectrum.

Figure 22:
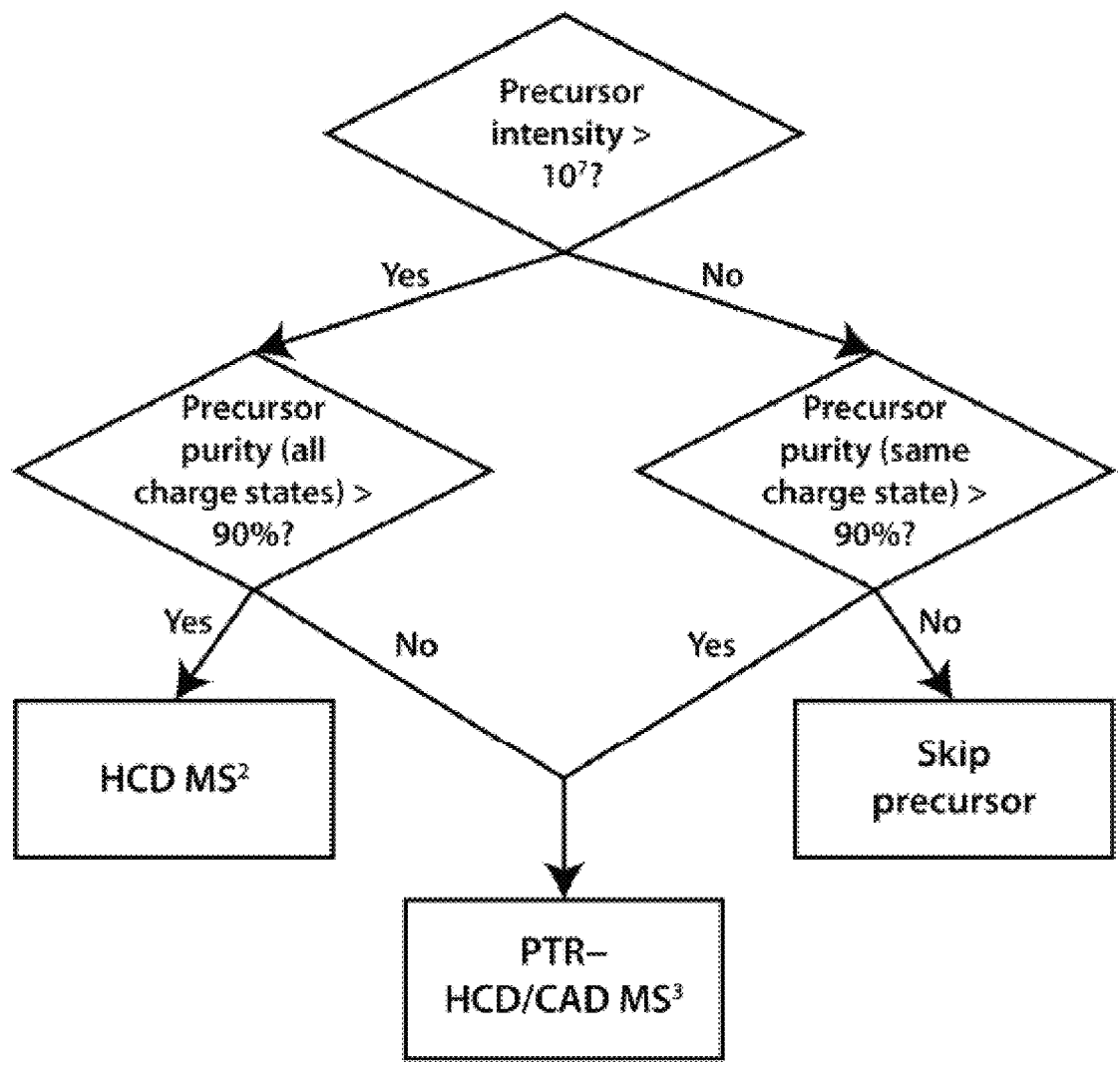
FIG. 22 provides a schematic diagram of an algorithm illustrating that an embodiment of the present invention can be selectively applied to a sample depending on whether highly intense or highly purified precursors are present.

FIG. 22 provides a schematic diagram of an algorithm illustrating that an embodiment of the present invention (e.g., QuantMode) can be selectively applied to a sample depending on whether highly intense or highly purified precursors are present. If a precursor ion has low intensity at the $MS^1$ stage and low purity (i.e., less than 90%) then accurate identification and/or quantification may be unlikely even with gas-phase purification. In this instance, the algorithm may direct this precursor to be skipped from further mass spectrometry analysis. If the precursor ion exhibits low intensity but has high purity, then further analysis may be performed with PTR. Similarly, PTR may be utilized if the precursor ion exhibits high intensity but low purity. If the precursor ion exhibits high intensity and high purity, then PTR may not be necessary and analysis by HCD $MS^2$ may be performed.

EXAMPLE 4

Low Resolution QuantMode

To extend gas-phase purification to a broader subset of proteomics, a gas-phase purification platform (named "low-res QuantMode") was developed that is amendable to stand-alone ion trap instruments. This method also utilizes PTR to eliminate precursor interference for the improvement of isobaric tag-based quantification and further allows the combination of sequential HCD and CAD fragmentation into one m/z analysis. With the development of low-res QuantMode, this functionality has now been extended to low resolution instruments in addition to high resolution instruments, providing a more accessible solution to the problem of precursor interference. It is believed that such a system will be a valuable tool to the proteomics community, as it will enable a broader subset of researchers to confidently and effectively incorporate isobaric tag-based quantitation into their studies.

In this method, beam-type activation can be achieved using ESI ion injection optics of stand-alone ion traps. This activation method, called front-end high energy collision-induced dissociation (fHCD), has recently been optimized and commercialized for use on benchtop instruments (LTQ Velos Pro, Thermo Fisher Scientific). fHCD is ideal for isobaric tag-based quantitation on low resolution instruments, as it yields product ions which closely resemble those of HCD, it outperforms PQD in peptide identifications (2-fold improvement) and reporter ion intensities (10-fold improvement), and, unlike CAD, it allows for the retention of reporter ions.

The scan sequence further comprises three separate scan events: 1) charge-state determination, 2) quantification, and 3) identification. Incorporation of these specialized scan events and fHCD into the QuantMode scan sequence enabled the development of a low-resolution gas-phase purification method which improves quantitative accuracy, maximizes peptide identifications, and minimizes unnecessary drains on duty cycle. Herein, the low-res QuantMode scan function is described in detail along with improvements provided by this method for isobaric tag-based quantification through the analysis of both a mixed organism model (which replicates a worst-case precursor interference scenario) and a complex biological time course sample.

Cell Culture and Differentiation

Wild-type yeast (*Saccharomyces cerevisiae*) was grown in rich medium to an OD600 of 0.6. Cells were collected and centrifuged at 14,200 g for 10 min at 4° C. The resulting cell pellet was washed twice with sterile water and centrifuged at 1,100 g for 5 min. Lysis buffer of approximately three times the cell pellet volume was added. The lysis buffer contained 8 M urea, 75 mM NaCl, 50 mM Tris (pH 8), 10 mM sodium pyrophosphate, 100 mM sodium butyrate, complete mini ETDA-free protease inhibitor (Roche Diagnostics) and phosSTOP phosphatase inhibitor (Roche Diagnostics). The cells were lysed using a French press, where the sample was pressed three times and then centrifuged for 15 min at 24,000 g at 4° C.

Human H1 embryonic stem cells were maintained in a feeder-independent system [Ludwig et al., *Nat. Materials*, 2006, 3, p. 637-646]. Cells were collected by application of an adequate volume of prewarmed (37° C.) 0.05% Tryp-LE to cover the culture surface for 10 min. After cell detachment, an equivalent volume of ice-cold DPBS (Invitrogen) was added before collecting the cells. Cell pellets were subsequently washed twice in ice-cold PBS and stored at −80° C. Cells were lysed via sonication in lysis buffer containing 30 mM NaCl, 50 mM Tris (pH 8), 2 mM $MgCl_2$, 50 mM NaF, 1 mM sodium orthovanadate, 6 mM sodium pyrophosphate, mini EDTA-free protease inhibitor (Roche Diagnostics) and phosSTOP phosphatase inhibitor (Roche Diagnostics).

C2C12 mouse myoblasts were cultured as subconfluent monolayers in DMEM high glucose medium (Invitrogen) with 10% fetal bovine serum (Invitrogen), 100 units/ml penicillin and 100 μg/ml streptomycin (Invitrogen) and incubated at 37° C. and 5% $CO_2$. To induce myotube differentiation, myoblasts were grown to confluence then switched to media containing 2% horse serum (Invitrogen). The cells were re-fed every 24 hours during the differentiation. Undifferentiated myoblasts were collected the day of the media change (day 0) and fully differentiated myotubes were collected 6 days following the media change (day 6). Cells were collected by dissociation with 0.05% Trypsin-EDTA (Invitrogen), washed with PBS, pelleted by centrifugation, snap frozen in liquid nitrogen and stored at −80° C. until use.

Cell pellets were resuspended in approximately three times the pellet volumes using lysis buffer. The lysis buffer contained 8 M urea, 50 mM Tris (pH 8), 40 mM NaCl, 2 mM $MgCl_2$, 50 mM NaF, 50 mM b-glyceraldehyde phosphate, 1 mM sodium orthovanadate, 10 mM sodium pyrophosphate, mini EDTA-free protease inhibitor (Roche Diagnostics), and phosSTOP phosphatase inhibitor (Roche Diagnostics). Cells were lysed via sonification. Protein content within each of the mouse samples was evaluated using a BCA assay (Thermo).

Cell Lysis and Digestion

Yeast, human, and mouse proteins were subject to cysteine residue reduction using 5 mM DTT and alkylation using 10 mM iodoacetamide. Proteins were then digested using a two-step process. First, Proteinase Lys-C (Wako Chemicals) was added to each sample at a ratio of 1:100 (enzyme:protein) and the resulting mixtures were incubated at 37° C. for 4 hours. Next, samples were diluted to a final concentration of 1.5 M urea (pH 8) with a solution of 25 mM tris and 2 mM CaCl. Sequencing-grade trypsin (Promega) was added to each sample at a ratio of 1:100 (enzyme:protein) and the resulting mixtures were incubated at 37° C. overnight. Reactions were quenched using trifluoroacetic acid. Samples were desalted using C18 solid-phase extraction columns (SepPak; Waters) and dried to completion.

Sample Preparation

Interference Sample: Yeast peptides were split into six equal mass aliquots; each aliquot was labeled with one of six TMT 6-plex reagents (m/z 126-131), as described previously (TMTsource). Yeast aliquots were mixed in the mass ratios 1:5:10:10:5:1, respectively. Human peptides were split into three equal mass aliquots; each aliquot was labeled with one of three TMT 6-plex reagents (m/z 129-131), as described previously (TMTsource). Human aliquots were mixed in the mass ratios 1:1:1, respectively. A small aliquot was obtained from each individual sample to provide material for control experiments. Yeast and human samples were then combined in a 2:1 mass ratio, respectively. All samples were dried to completion and resuspended in 0.2% formic acid for LC-MS analysis.

Myoblast Differentiation Sample.

The 'day 0' and 'day 6' mouse samples were split into three equal mass aliquots; each of the 'day 0' aliquots was labeled with one of the lightest three TMT 6-plex reagents (m/z 126-128) while each of the 'day 6' aliquots was labeled with one of the heaviest three TMT 6-plex reagents (m/z 129-131), as described previously (TMTsource). The six resulting aliquots were desalted using C18 solid-phase extraction columns, dried to completion, and combined in equal masses. The labeled mouse peptide mixture was fractionated using SCX. Eight fractions were collected over the SCX gradient: two 6-min intervals, five 1-min intervals, and one 10-min interval. Each fraction was lyophilized, desalted, dried to completion, and resuspended in 0.2% formic acid for LC-MS analysis.

Liquid Chromatography-Mass Spectrometry

All experiments were performed using a NanoAcquity UPLC system (Waters) coupled to an ETD-enabled LTQ Velos mass spectrometer (Thermo). A nanoESI source was used for the generation of precursor peptide cations. Samples were loaded onto a precolumn (75 μm i.d., packed with 10 cm of 5 μm C18 particles; Microm Bioresources, Inc) for 15 minutes at 98:2 0.2% formic acid:acetonitrile with 0.2% formic acid at a flow rate of 0.850 μL/min. Samples were then separated on an analytical column (75 μm i.d., packed with 15 cm of 5 μm C18 particles; Microm Bioresources, Inc) at a flow rate of 0.300 L/min using a gradient consisting of an initial steep rise to 7% B (acetonitrile with 0.2% formic acid) followed by a 90 minute linear gradient from 7% to 30% B and a final ramp to 70% B over 4 minutes which was held for 5 minutes. The column was equilibrated with 2% buffer B for an additional 20 minutes. Precursor peptide cations were generated from the eluent through the utilization of a nanoESI source.

All non-QuantMode instrument methods consisted of an $MS^1$ scan (300-1600 m/z) followed by ten data-dependent trapHCD $MS^2$ scans, all analyzed in the ion trap at a normal scan speed. $MS^2$ scans employed a precursor isolation window of 3 Th and a trapHCD normalized collision energy (NCE) setting of 60 for 2 ms.

All QuantMode instrument methods consisted of an $MS^1$ scan (300-1600 m/z) followed by three data-dependent QuantMode scan cycles, all analyzed in the ion trap. Precursor isolation windows of 3 Th were used. The QuantMode scan cycle utilizes proton transfer reactions (PTR) to achieve gas-phase purification. For all experiments, the nitrogen adduct of fluoranthene (m/z 216) was used as the PTR reagent ion. Reagent anions were generated by an integrated chemical ionization source (commercial ETD module; Thermo); source conditions and all associated ion optics were optimized for this reagent prior to each set of experiments.

The QuantMode scan cycle was composed of three separate scan events: 1) charge-state determination scan; 2) quantitation scan(s); and 3) identification scan. The charge-state determination scan was an $MS^2$ event in which isolated precursor cations were subjected to resonant-excitation CAD (q-value=0.25, NCE 1, 1 ms) and analyzed in the ion trap at an enhanced scan speed over a 15 Th region surrounding the precursor isolation window. Instrument code was modified to store the charge-state of each isolated precursor population for the subsequent scan (charge-state prediction based on the m/z of ions surrounding the $MS^2$ base peak). The quantitation scan was an $MS^3$ event. Isolated precursor cations and reagent anions were sequestered in the high pressure trap and comingled via charge-sign independent trapping. The duration of the PTR reaction was dictated by the charge-state prediction in the previous scan event to ensure optimal reaction conditions for single charge reduction. Reaction times were set at 80 ms for doubly charged precursors, 30 ms for triply charged precursors, and 20 ms for quadruply charged precursors. Following PTR, the charge-reduced precursor population was re-isolated based on the predicted charge-state. If no charge-state was predicted, the precursor was re-isolated as if it were initially a triply charged cation. The re-isolated precursors then underwent trapHCD activation [NCE 90 (optimal for tag generation), 2 ms] followed by ion trap analysis scanned at normal scan speed over a 30 Th window surrounding the TMT-tag region (110-140 m/z). If no charge-state was determined for the precursor of interest, a second quantitation scan was performed in which precursors were treated as quadruply charged cations. Instrument code was modified to skip this second quantitation scan if charge-state was determined. The identification scan was an $MS^2$ event in which isolated precursor cations were subjected to trapHCD [NCE 70 (for doubly-charged precursors)/NCE 50 (for all other precursors), 2 ms] and analyzed in the ion trap at a normal scan speed over the full mass range.

The automatic gain control (AGC) target settings for precursor cations were $4 \times 10^4$ for $MS^1$ scans, $1 \times 10^4$ for CAD-activated $MS^2$ scans, $4 \times 10^4$ for trapHCD-activated $MS^2$ scans, and $1.2 \times 10^5$ for PTR quantitation scans. Precursors were subject to dynamic exclusion for 60 seconds using a window of −0.5 to 2.5 Th. The reagent anion AGC target setting was $2 \times 10^5$.

Data Analysis

Data was processed using the in-house software suite COMPASS. OMSSA (version 2.1.8) searches for interference sample data were performed against the International Protein Index (IPI: www<dot>ebi<dot>ac<dot>uk/IPI/) target-decoy database comprised of both yeast (Saccharomyces Genome Database, www<dot>yeastgenome<dot>org, "all" version including all systematically named open reading frames (ORFs), including verified, uncharacterized, and dubious ORFs and pseudogenes) and human (version 3.80) proteins. OMSSA searches for myoblast differentiation data were performed against the Universal Protein Resource (UNIPROT: www<dot>uniprot<dot>org/) target-decoy mouse database. Searches were conducted using an average precursor mass tolerance of ±5.0 Da and a monoisopic product mass tolerance of ±0.50 Da. The fixed modifications specified were carbamidomethylation of cysteines, TMT 6-plex on peptide N-termini, and TMT 6-plex on lysines. The variable modifications specified were oxidation of methionine and TMT 6-plex on tyrosines. A maximum of 3 missed tryptic cleavages were allowed. Interference data was independently trimmed to 1% FDR and subsequently filtered to remove all human-derived peptides, enabling only yeast-derived peptides to be considered for analysis. Myoblast differentiation data fractions were collectively filtered to 1% FDR for each set of experiments. Noise-band capping of missing TMT 6-plex channels was manually applied during quantitative analyses based on the lowest TMT peaks detected within each set of experiments. Statistical and GO/KEGG-term analyses of myoblast differentiation data were conducted using the Persius software package [Cox, J. and Mann, M., Nat Biotechnol, 2008, 26, pgs. 1367-72].

Low-Res QuantMode Scan Sequence

Figure 23:
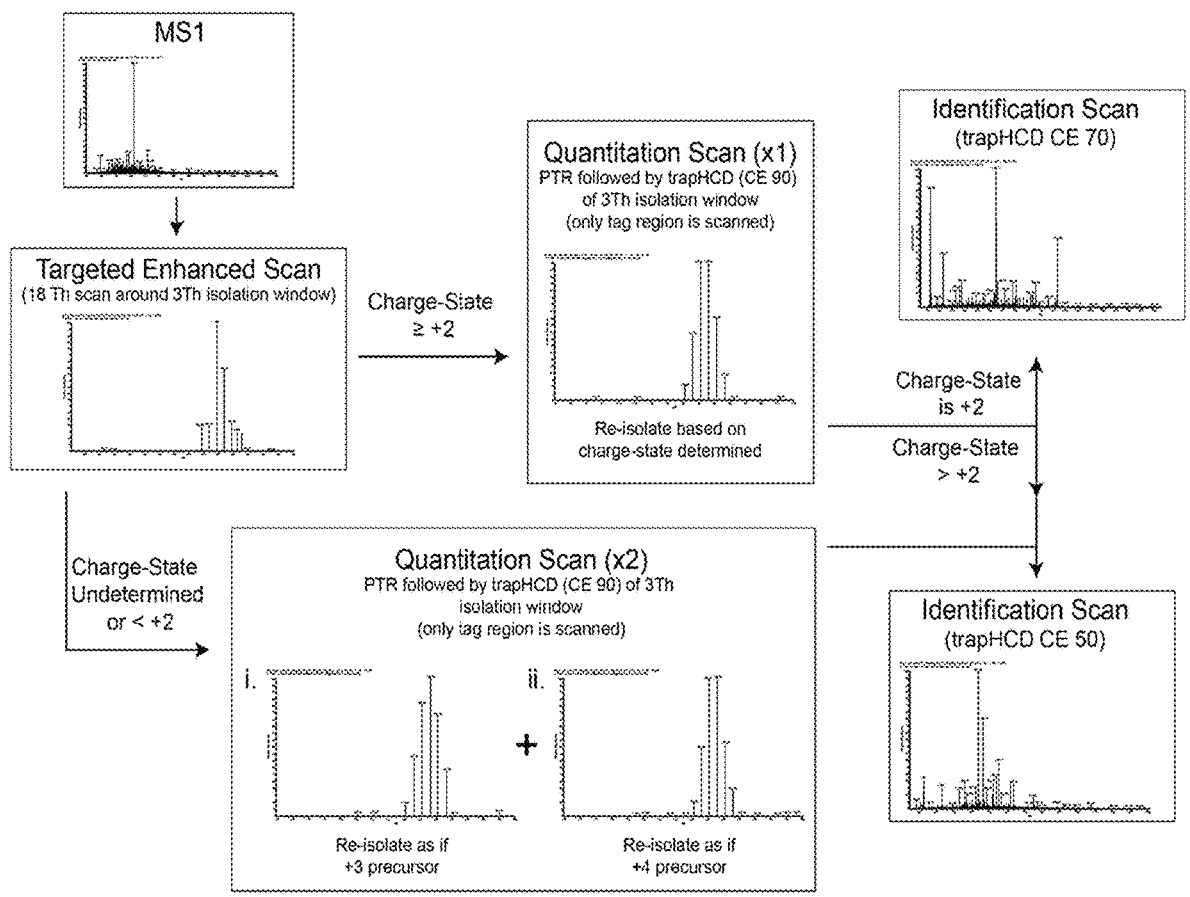
FIG. 23 provides a flowchart illustrating the sequence of scan events in one embodiment of the present invention (low-res QuantMode) including a charge-state determination scan, one or more quantitation scans, and an identification scan.

Instrument software was modified to enable implementation of low-resolution QuantMode (low-res QuantMode) on a stand-alone ion trap. A full low-res QuantMode scan sequence subjects a precursor to three separate scan events: a charge-state determination scan, one or more quantitation scans, and an identification scan. This workflow is outlined in FIG. 23, and each scan event within the cycle is presently described.

Charge-State Determination Scan. Unlike orbitrap mass analyzers, ion trap mass analyzers cannot provide the spectral resolution necessary to elucidate charge-state information from sampled precursor ions. Knowledge of precursor charge-state is critical for the implementation of PTR within the low-res QuantMode method; without this information, re-isolation of the charge-reduced precursor is inefficient, at best. For this reason, the first low-res QuantMode scan event was dedicated entirely to the acquisition of precursor charge-state.

Charge-state determination was achieved in this first scan event by isolating precursor ions in a 3Th m/z window and performing m/z analysis on the isolated region using a slower, 'enhanced' scan rate. This enhanced scan rate improved baseline resolution to enable subsequent charge state determination for doubly and triply protonated precursor peptides.

The utility of the targeted enhanced scan for charge state prediction was evaluated outside of the low-res QuantMode method using a sample of tryptic, unlabeled mouse peptides. A 90 minute data-dependent top 3 method subjected each precursor to three scan events: 1) the low-res QuantMode charge-state determination scan; 2) PTR followed by full m/z analysis; and 3) CID (35 NCE) followed by full m/z analysis. The latter two scans in this method provide charge-state verification for the targeted scan. A computer algorithm was written which determined precursor charge-state from PTR spectra based on the intensity and m/z locations of the charge-reduced precursors. OMSSA identifications obtained from CID spectra provided another source of charge-state information for each sampled precursor.

Figure 24:
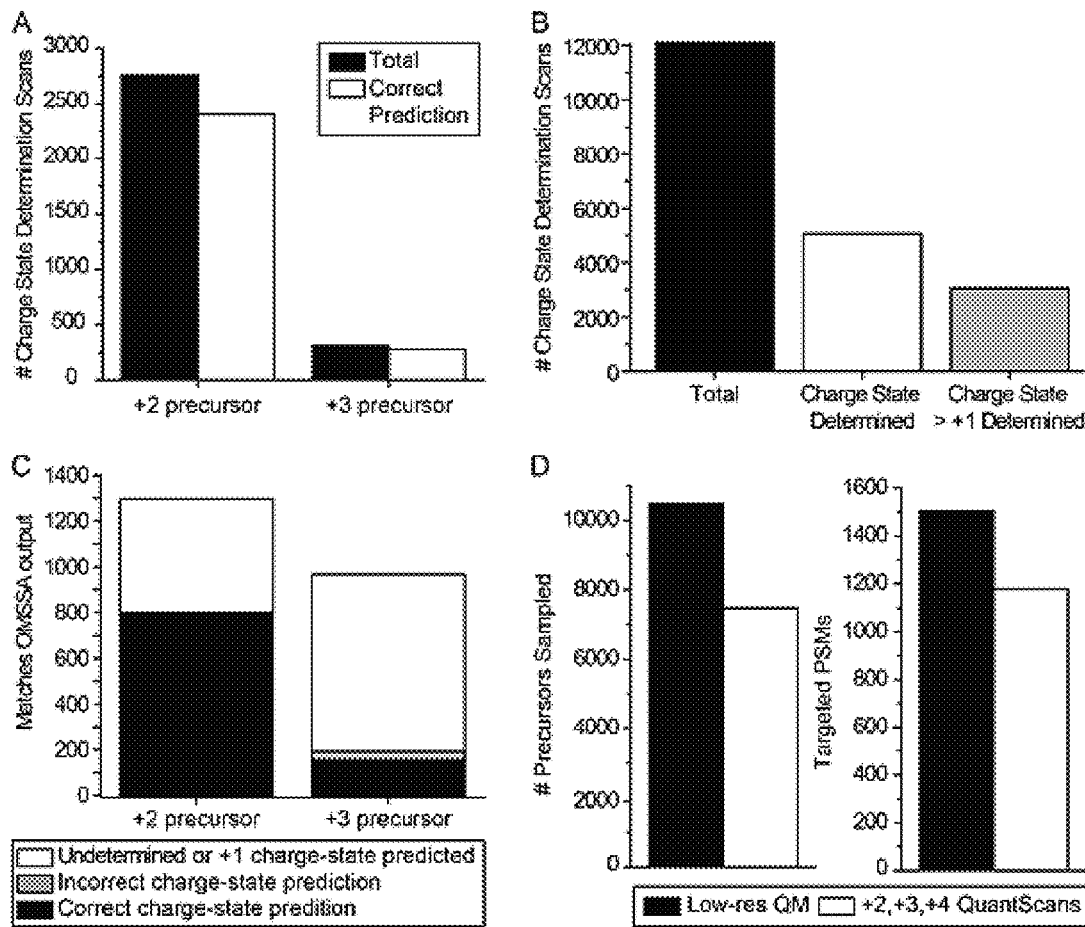
FIG. 24 provides data evaluating charge determination scans performed in an embodiment of the present invention. This data confirms that a targeted charge state scan prediction of a +2 or +3 charged precursor was correct at least 88% of the time (panel A). However, the targeted scan was only able to predict charge state information for 42% of all precursors sampled, and only 60% of these predicted charge-states were associated with peptides amenable to PTR (≥+2 charge) (panel B). The targeted scan also generated significantly less predictions for the +3 charged precursors (panel C). Panel D shows that integration of the targeted charge determination scan into the low-res QuantMode scan enabled a shorter duty cycle and a greater amount of peptide identifications than quantitatively evaluating each peptide as a +2, +3, and +4 charged species.
Figure 25:
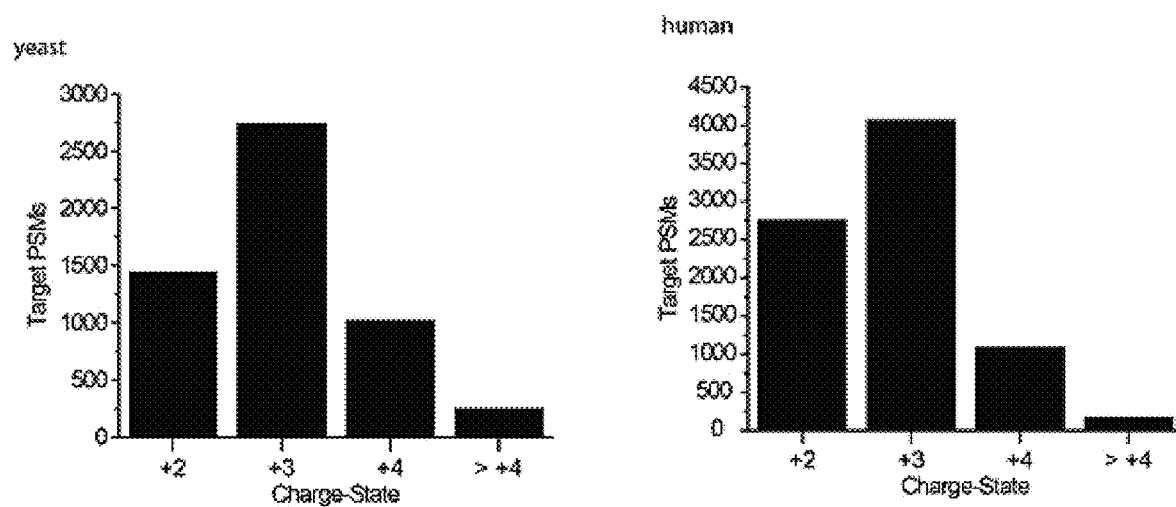
FIG. 25 shows a charge-state distribution of isobarically labeled peptides where a significant amount of peptides have a charge state of +3, +4 and greater +4.

These verification scans allowed confirmation that a targeted scan prediction of a doubly or triply charged precursor was correct at least 88% of the time (FIG. 24, panel a). Despite this high success rate, however, the targeted scan was only able to predict charge state information for 42% of all precursors sampled, and only 60% of these predicted charge-states were associated with peptides amenable to PTR (≥+2 charge) (FIG. 24, panel b). Although the targeted scan correctly predicted charge-state information for over half of the doubly charged precursors identified in the evaluation experiment, it generated significantly less predictions for the triply charged- and no predictions for the quadruply charged-precursors (FIG. 24, panel c). Peptides labeled with isobaric tags tend to ionize to higher charge states than non-labeled peptides, making highly-charged precursors with un-identified charge states too important to completely ignore (FIG. 25). The charge state determination scan was therefore mainly utilized as a screening process; if no charge state was determined, the peptide was evaluated as both a triply and quadruply charged peptide for quantitation purposes. Charge-state was later confirmed during data processing using PSM information gleaned from the identification scan. By eliminating the need to quantitatively evaluate each peptide as doubly, triply, and quadruply charged species, integration of the targeted scan into low-res QuantMode actually enabled a shorter duty cycle and a greater amount of peptide identifications (FIG. 24, panel d). It should be noted that performing this targeted scan using a slower 'zoom' scan speed resulted in no improvement in charge-state identification and negatively affected both duty cycle and total peptide identifications (data not shown).

Quantitation Scan(s). Peptide quantification was performed in the second scan event through the utilization of gas-phase purification. Precursor ions were subjected to PTR and re-isolated based on the charge-state determined in the previous scan. This 'purified' charge-reduced precursor population was then fragmented with fHCD activation at a collision energy optimal for tag generation. As was mentioned above, in cases where charge-state information was unavailable, two quantitation scans were performed: one which assumed a precursor charge state of +3 and one which assumed a precursor charge state of +4. Whether performing a single or multiple quantitation scans, m/z analysis was only performed for a narrow range corresponding to the reporter tag m/z region; in so doing, the duty cycle penalty associated with multiple MS/MS events was drastically reduced.

Identification Scan. Lastly, an identification scan was performed to ascertain each peptide sequence. Useful sequence ions were generated using fHCD activation. Alternatively, this identification scan could have been performed using CAD activation; however, it was found that trapHCD activation produced a greater number of peptide spectral matches (data not shown).

Figure 26:
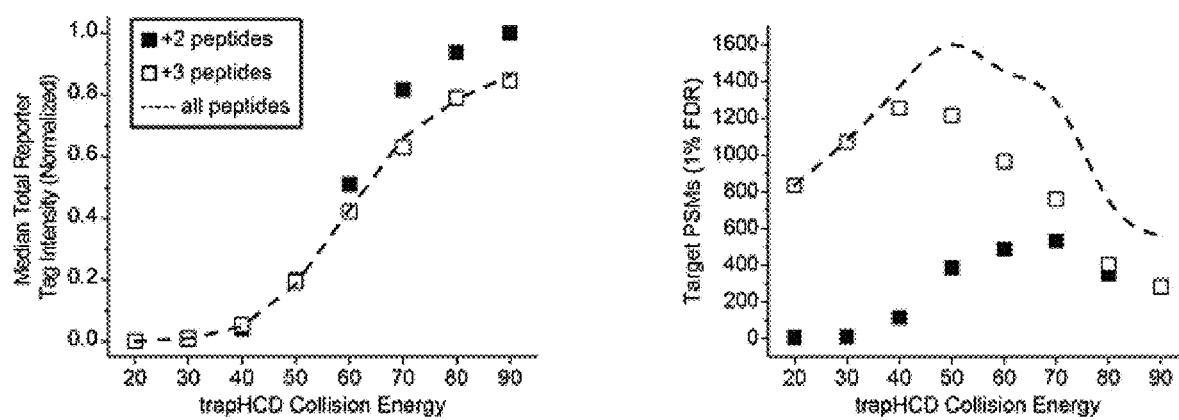
FIG. 26 shows optimal activation conditions and optimal collision energy for peptide identification and reporter tag intensity generation.

Segmenting the low-res QuantMode scan sequence into three distinct events enabled the decoupling of sequence and reporter ion generation; this increased the likelihood of obtaining accurate quantitation and sequence information from each peptide analyzed. Optimal activation conditions for peptide identification and tag generation were determined experimentally (FIG. 26). The optimal collision energy for high reporter ion signal intensity was independent of charge-state, which enabled a single collision energy (NCE 90) to be used for all quantitation scans (FIG. 26). The optimal collision energy for the generation of useful sequence ions, however, was dependent on charge-state (FIG. 26). Since charge-state information isn't typically available on low-resolution instruments, methods scale activation energies based on a default charge state (set to +3 in all of these experiments); all peptides are therefore subject to the same collision energies, regardless of their actual charge-state. In the low-res QuantMode analyses, it was possible to take advantage of the charge-state determination scan to scale up the activation energy for +2 precursors and scale down the activation energy for all other precursors. Overall, this minimized the incidence of underreacted/overreacted spectra and maximized peptide identifications in the experiments.

Evaluation of Low-Res QuantMode Using Interference Model

To evaluate the ability of low-res QuantMode to remedy the problem of precursor co-isolation in isobaric tag-based quantification, the method was first tested using a mixed organism model designed to mimic a 'worst-case' scenario for precursor interference. To generate this mixed organism sample, yeast peptides labeled with TMT tags 126, 127, 128, 129, 130, or 131 were mixed in a 1:5:10:10:5:1 ratio, respectively. The yeast sample was then contaminated with an equivalent amount of human peptides carrying the tags 129, 130, and 131 (mixed in a 1:1:1 ratio, respectively). LC-MS/MS analysis of the interference sample highlights the breakdown of quantitative accuracy which occurs in the reporter tag region when multiple species are co-isolated; any yeast-identified peptide containing human interference will contain skewed 5:1 and 10:1 ratios in the right-most channels while maintaining the correct 5:1 and 10:1 ratios in the left-most channels. For the purpose of this analysis, the left-most channels (126-128) will be referred to as 'control channels'; control channel ratios are determined by comparing tags 127:126 and 128:126 (5:1 and 10:1 ratios, respectively). Similarly, the right-most channels (129-131) will be referred to as 'interference channels'; interference channel ratios are determined by comparing tags 130:131 and 129:131 (5:1 and 10:1 ratios, respectively).

Baseline quantitation was established through fHCD analysis (data-dependent top 10 (ddTop10), NCE 60) of the yeast control (i.e., the interference sample prior to the addition of human peptides). With no interfering species present, 4.8:1 and 8.9:1 ratios in the control channels and 4.5:1 and 8.2:1 ratios in the interference channels were observed. Deviation from the expected 5:1 and 10:1 ratios can be attributed to sample preparation inconsistencies.

Figure 27:
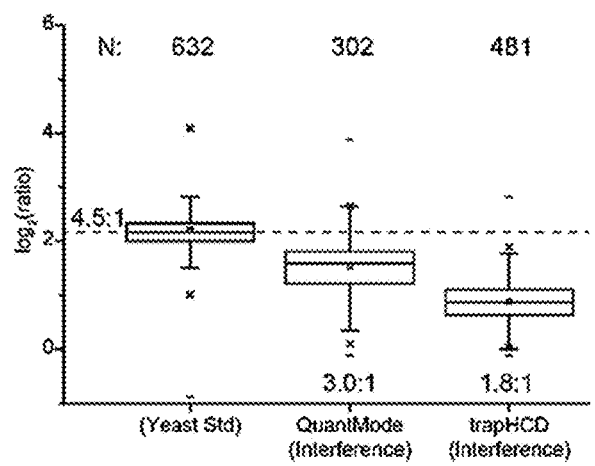
FIG. 27 shows quantitative results for yeast peptides identified in experiments utilizing a low-res QuantMode embodiment of the present invention compared to mass spectrometry analysis using trapHCD.
Figure 27:
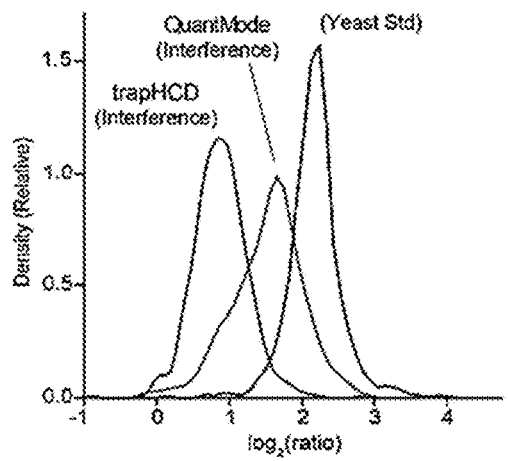
Figure 27:
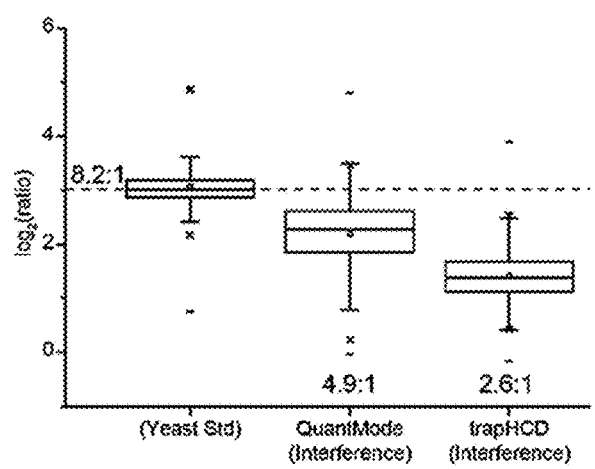
Figure 27:
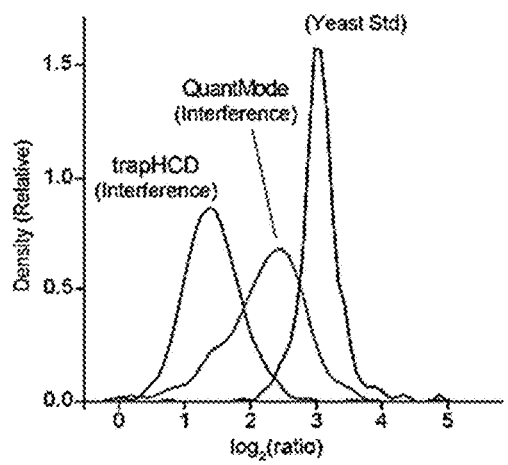

The interference sample (composed of both yeast and human peptides in the amounts specified above) was analyzed twice, once using only fHCD (ddTop10, NCE60) and once using QuantMode (as described). Data was filtered to provide quantitative results for only the yeast peptides identified in each experiment; outcomes are shown in FIG. 27. The severity of the precursor interference problem is demonstrated by the truncated ratios observed in the fHCD-only analysis. While control channels retained ratios of 4.9:1 and 9.2:1, interference channels showed incredibly truncated ratios of 1.8:1 and 2.6:1. This translates to a 3-fold underestimation of the 129:131 ratio and a 2.5-fold underestimation of the 130:131 ratio. Implementation of low-res QuantMode, however, was able to recover these diminished proportions. Again, control channels retained ratios of 4.9:1 and 9.2:1, but interference channels now displayed ratios of 3.0:1 and 4.9:1—numbers which are significantly closer to the respective 4.1:1 and 8.2:1 ratios observed in the yeast control. This marks a 28% and 27% improvement in quantitative accuracy for the 129:131 and 130:131 reporter tag ratios (32% to 60% and 40% to 67%), respectively, when comparing quantitative analyses conducted with and without low-res QuantMode.

The low-res QuantMode scan cycle provides dramatic improvements in quantitative accuracy, but does so at the slight expense of peptide and protein identifications. Despite efforts to make the method as efficient as possible, the low-res QuantMode duty cycle is significantly slower than the fHCD-only duty cycle, which translates to a 53% loss in peptide identifications and a 37% loss in protein identifications. This begs the question of whether it is more beneficial to sacrifice quantitative accuracy or high sequence coverage when analyzing complex samples. Quantitative analysis of a real, complex biological time course sample advocates for the former, and the results of this study are presently revealed.

Evaluation of Low-Res QuantMode Using C2C12 Myogenesis Sample

Interference model experiments establish improvements in quantitative accuracy when using low-res QuantMode in a 'worst case' interference scenario; however, it is demonstrated that the utility of low-res QuantMode translates to the analysis of large-scale, complex biological samples as well.

The differentiation of mouse-derived C2C12 myoblasts has been extensively studied over the past decade as a model system for the development and interaction of skeletal muscle myocytes. Over the course of six days, C2C12 myoblasts undergo myogenic differentiation to form myotubes, and this development process is accompanied by dynamic changes in protein expression. In recent years, quantitative mass spectrometry methods, such as spectral counting and SILAC, have been utilized to investigate these myogenic protein dynamics. All studies find significant changes in the presence of metabolic and structural proteins during various stages of the differentiation process.

To validate the quantification advantages provided by the low-res QuantMode method, both fHCD (ddTop10, NCE60) and low-res QuantMode were used to compare relative protein levels present in the myogenic cells at day 0 and day 6 of the differentiation process. Myoblast (day 0) and myotube (day 6) cells were separately harvested, lysed, digested and split into three equal mass aliquots. Each myoblast aliquot was separately labeled with TMT 6-plex tags 126 to 128 m/z while each myotube aliquot was separately labeled with TMT 6-plex tags 129-131 m/z. All aliquots were combined in equal mass ratios; the resulting sample was fractionated with SCX and analyzed using both fHCD and QuantMode LC-MS methods.

Figure 28:
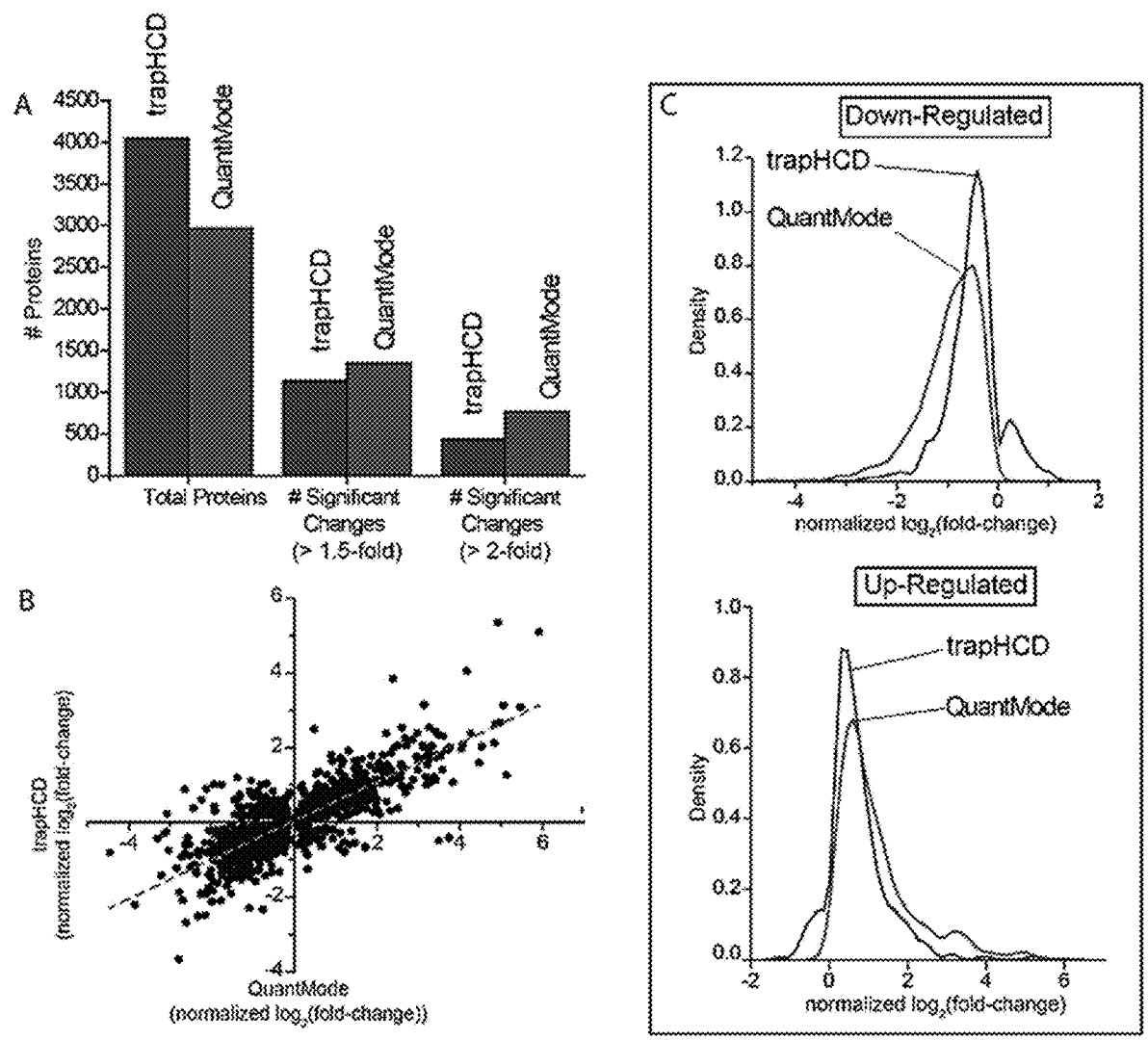
FIG. 28 shows relative protein levels present in the myogenic cells at day 0 and day 6 of the differentiation process in experiments utilizing a low-res QuantMode embodiment of the present invention compared to mass spectrometry analysis using trapHCD. Panels A-C show that fHCD-only analyses were able to identify a greater overall number of proteins than low-res QuantMode analyses but that low-res QuantMode actually identified more 1.5-fold changes than fHCD.

The results of this analysis are presented in FIG. 28. As was observed in the interference experiments, a faster duty cycle enables fHCD-only analyses to identify a greater overall number of proteins than low-res QuantMode analyses (4050 vs. 2964, respectively). When assessing the number of protein identifications associated with changes greater than 1.5-fold, however, the two methods become comparable; in fact, low-res QuantMode actually identified more 1.5-fold changes than fHCD by a margin of almost 15% (1326 vs. 1132, respectively). Improvements in dynamic range only become more substantial as low-res QuantMode and fHCD identifications are compared at higher fold-changes; low-res QuantMode produced significantly more >2-fold (766 vs. 438) and >5-fold (96 vs. 12) changes overall (FIG. 28, panel a). Given the 1332 proteins detected in both sets of experiments, greater fold-changes were discovered, on average, when proteins were analyzed using low-res QuantMode (FIG. 28, panels b and c). In a large-scale time course study such as this one, sound quantitative accuracy and high dynamic range are essential for the determination of biological relevance.

Figure 29:
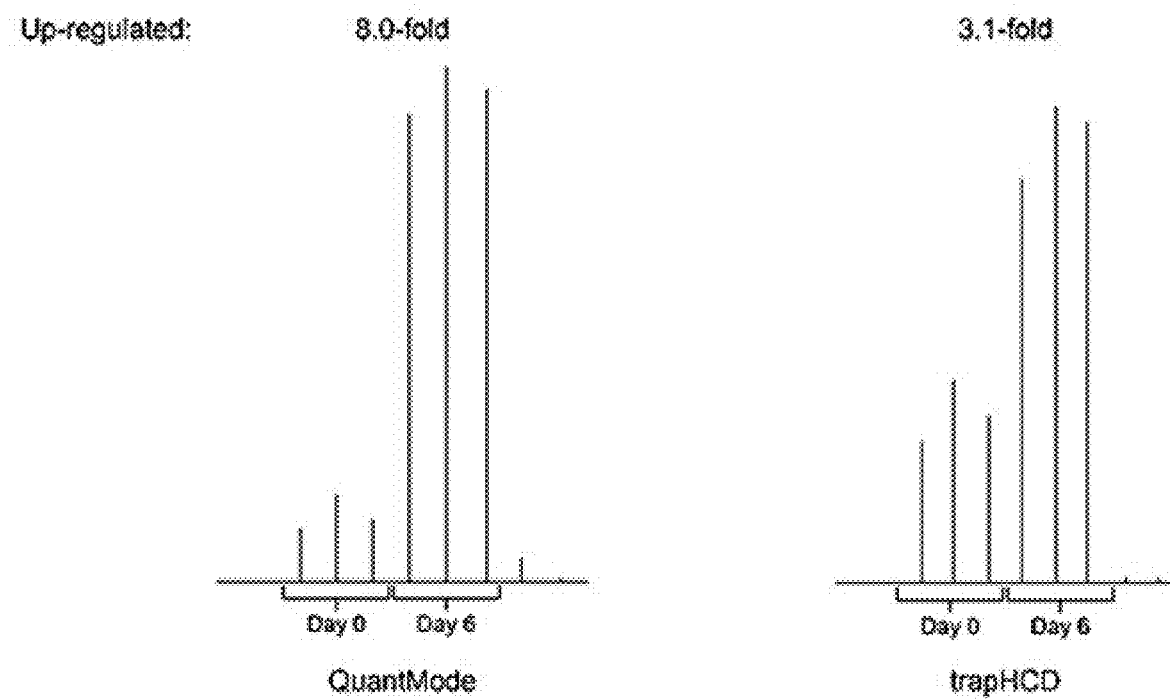
FIG. 29 provides spectra for two proteins discovered during a six day time course. The results from the low-res QuantMode experiment indicated an 8.0 fold difference in amount of the protein from day zero to day 6, while the trapHCD experiment only indicated a 3.1 fold increase in the protein.

FIG. 29 illustrates this point by presenting typical $MS^2$ data obtained for two proteins discovered during the course of both experiments. The levels of both proteins significantly change over the six day time course; however, the differences in protein levels are significantly more pronounced in QuantMode analysis. This suggests that these proteins may change more dynamically in the differentiation process than would have been thought given only fHCD data. By purifying the precursor population prior to fragmentation, the QuantMode scan function generates data that is significantly more accurate, and therefore more useful, for biological applications.

Although the description herein contains many specifics, these should not be construed as limiting the scope of the invention, but as merely providing illustrations of some of the embodiments of the invention.

Each reference cited herein is hereby incorporated by reference in its entirety. However, if any inconsistency arises between a cited reference and the present disclosure, the present disclosure takes precedent. Some references provided herein are incorporated by reference to provide details concerning the state of the art prior to the filing of this application, other references can be cited to provide additional or alternative device elements, additional or alternative materials, additional or alternative methods of analysis or applications of the invention. Patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, methods steps set forth in the present description. As will be obvious to one of skill in the art, methods and devices useful for the present methods can include a large number of optional composition and processing elements and steps.

One of ordinary skill in the art will appreciate that device elements, as well as materials, shapes and dimensions of device elements, as well as methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed can be resorted to by those skilled in the art, and that such modifications and variations are considered to be within the scope of this invention.

When a Markush group or other grouping is used herein, all individual members of the group and all combinations and possible subcombinations of the group are intended to be individually included in the disclosure. Every combination of components or materials described or exemplified herein can be used to practice the invention, unless otherwise stated. One of ordinary skill in the art will appreciate that methods, device elements, and materials other than those specifically exemplified can be employed in the practice of the invention without resort to undue experimentation. All art-known functional equivalents, of any such methods, device elements, and materials are intended to be included in this invention. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this invention. The invention illustratively described herein suitably can be practiced in the absence of any element or elements, limitation or limitations which is not specifically disclosed herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The term "comprising" is intended to be broader than the terms "consisting essentially of" and "consisting of", however, the term "comprising" as used herein in its broadest sense is intended to encompass the narrower terms "consisting essentially of" and "consisting of", thus the term "comprising" can be replaced with "consisting essentially of" to exclude steps that do not materially affect the basic and novel characteristics of the claims and "comprising" can be replaced with "consisting of" to exclude not recited claim elements.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed can be resorted to by those skilled in the art, and that such modifications and variations are considered to be within the scope of this invention as defined by the appended claims.

Although the description herein contains many specifics, these should not be construed as limiting the scope of the invention, but as merely providing illustrations of some of the embodiments of the invention.

What is claimed is:

1. A mass spectrometer system for analyzing an isobarically labeled analyte, the system comprising:
    an ion source for generating ions from the isobarically labeled analyte in a mixture with one or more molecules able to generate contaminant ions during mass spectrometry;
    first ion separation optics in communication with the ion source for separating ions according to their mass-to-charge ratios;
    ion reaction optics in communication with the first ion separation optics for generating mass-to-charge-manipulated ions;
    ion fragmentation optics in communication with the first ion separation optics for generating product ions;
    second ion separation optics in communication with the ion fragmentation optics for separating ions according to their mass-to-charge ratios;
    a first ion detector in communication with the second ion separation optics for detecting ions separated according to their mass-to-charge ratios;
    a controller operably connected to the first and second ion separation optics, the ion reaction optics, the first ion detector, and the ion fragmentation optics;
    wherein the controller controls the ion optics and detector so as to:
    (a) generate a first distribution of precursor ions from the mixture during $MS^1$ stage ionization;
    (b) identify a target range of mass-to-charge ratios of the first distribution of precursor ions, wherein said target range includes mass-to-charge ratios of precursor ions generated from the isobarically labeled analyte as well as contaminant ions;
    (c) via the first separation optics, isolate precursor ions from the first distribution of precursor ions, where the isolated precursor ions have mass-to-charge ratios within the identified target range, wherein precursor ions outside of the identified target range are removed from communication with the ion reaction optics;
    (d) reacting the isolated precursor ions within the identified target range to selectively change the mass-to-charge ratios of the isolated precursor ions by a known amount, thereby generating a distribution of mass-to-charge-manipulated precursor ions, wherein precursor ions outside of the identified target range are not reacted;
    (e) identify a desired range of mass-to-charge ratios of the distribution of mass-to-charge-manipulated precursor ions, wherein the desired range includes mass-to-charge ratios of precursor ions generated from the isobarically labeled analyte and manipulated by a known amount as described in step (d), and wherein the desired range does not include mass-to-charge ratios of contaminant ions manipulated as described in step (d);
    (f) via the second separation optics, separate mass-to-charge-manipulated precursor ions having a mass-to-charge ratio within the desired range from mass-to-charge-manipulated contaminant ions having a mass-to-charge ratio outside of the desired range, thereby generating isolated mass-to-charge-manipulated precursor ions having a mass-to-charge ratio within the desired range, wherein the mass-to-charge-manipulated contaminant ions are removed from communication with the ion fragmentation optics;
    (g) fragment ions corresponding to the isolated mass-to-charge-manipulated precursor ions during $MS^2$ fragmentation, thereby generating first product ions, wherein the mass-to-charge-manipulated contaminant ions are not fragmented; and
    (h) measure the mass-to-charge ratios of the first product ions, thereby generating first product ion mass spectrometry data.

2. The system of claim 1, wherein the controller further controls the ion optics and detector so as to:
    (i) generate a second distribution of precursor ions from the isobarically labeled analyte;
    (j) identify a range of mass-to-charge ratios of the second distribution of precursor ions;
    (k) fragment ions corresponding to the range of mass-to-charge ratios of the second distribution of precursor ions, thereby generating second product ions;
    (l) measure the mass-to-charge ratios of the second product ions, thereby generating second product ion mass spectrometry data; and
    (m) analyze the second product ion mass spectrometry data.

3. The system of claim 1, wherein, to selectively change the mass-to-charge ratios of the isolated precursor ions, the controller further controls the ion optics and detectors to:
    subject the first distribution of precursor ions to reaction with a predetermined species to selectively change the mass-to-charge ratios of precursor ions in the identified target range of mass-to-charge ratios, thereby generating the distribution of mass-to-charge-manipulated precursor ions, wherein the reaction with a species to selectively change the mass-to-charge ratios of the range of mass-to-charge ratios comprises a proton-transfer reaction.

4. The system of claim 1, further comprising a second ion detector in communication with the first ion separation optics for detecting ions separated according to their mass-to-charge ratios and generating first precursor ion mass spectrometry data corresponding to the first distribution of precursor ions.

5. The system of claim 1, wherein the controller controls the ion optics and detector so as to:
    (j) fragment ions corresponding to the isolated mass-to-charge-manipulated precursor ions, thereby generating first product ions;

wherein the isolated mass-to-charge-manipulated precursor ions are fragmented by beam-type collisionally activated dissociation, ultraviolet photo-dissociation, infrared photodissociation, electron transfer dissociation, electron capture dissociation, surface induced dissociation, or resonant excitation collisionally activated dissociation.

6. The system of claim 1, wherein the isobarically labeled analyte comprises proteins or peptides and the controller controls the ion optics and detectors to analyze the isobarically labeled analyte to quantify the amount of proteins or peptides in the analyte.

7. The method of claim 1, wherein the identified target range of mass-to-charge ratios of the second distribution of precursor ions does not include ions having a mass-to-charge ratio less than 200 m/z units.

\* \* \* \* \*